US008318689B2

(12) United States Patent
Harel-Bellan et al.

(10) Patent No.: US 8,318,689 B2
(45) Date of Patent: Nov. 27, 2012

(54) SIRNA-BASED CANCER TREATMENT

(75) Inventors: Annick Harel-Bellan, Paris (FR); Slimane Ait-Si-Ali, Villejuif (FR); Florence Cabon-Georget, Vitry sur Seine (FR); Anne Chauchereau, Fontenay-aux-Roses (FR); Francois Dautry, Paris (FR)

(73) Assignee: Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 12/072,803

(22) Filed: Feb. 28, 2008

(65) Prior Publication Data

US 2008/0287385 A1 Nov. 20, 2008

Related U.S. Application Data

(62) Division of application No. 10/494,800, filed as application No. PCT/FR02/03843 on Nov. 8, 2002, now Pat. No. 7,371,735.

(30) Foreign Application Priority Data

Nov. 9, 2001 (FR) ..................................... 01 14549
Apr. 10, 2002 (FR) ..................................... 02 04474

(51) Int. Cl.
*C12N 15/11* (2006.01)
*C07H 21/04* (2006.01)
*C12Q 1/68* (2006.01)
*G01N 33/574* (2006.01)

(52) U.S. Cl. ....... 514/44 A; 536/24.5; 435/6.1; 435/7.23

(58) Field of Classification Search .................. 536/24.5; 514/44
See application file for complete search history.

(56) References Cited

U.S. PATENT DOCUMENTS

| | | | | |
|---|---|---|---|---|
| 4,714,613 A * | 12/1987 | Shouval et al. | ............ | 424/149.1 |
| 5,165,923 A * | 11/1992 | Thorpe et al. | ............. | 424/179.1 |
| 5,556,956 A | 9/1996 | Roy et al. | | |
| 5,840,301 A * | 11/1998 | Rockwell et al. | .......... | 424/143.1 |
| 6,426,335 B1 * | 7/2002 | Janjic et al. | ................. | 514/44 R |
| 6,479,654 B1 * | 11/2002 | Baird et al. | .................... | 536/23.5 |
| 7,148,342 B2 * | 12/2006 | Tolentino et al. | ............ | 536/24.5 |
| 7,176,304 B2 * | 2/2007 | McSwiggen et al. | ........ | 536/24.5 |
| 7,919,473 B2 | 4/2011 | De Fougerolles et al. | | |
| 7,947,659 B2 | 5/2011 | De Fougerolles et al. | | |
| 2010/0087508 A1 | 4/2010 | Bumcrot et al. | | |
| 2010/0267806 A1 | 10/2010 | Bumcrot et al. | | |
| 2011/0224282 A1 | 9/2011 | De Fougerolles et al. | | |

FOREIGN PATENT DOCUMENTS

| | | |
|---|---|---|
| EP | 0 769 552 A1 | 4/1997 |
| EP | 2365077 A1 | 9/2011 |
| WO | WO 94/18835 A1 | 9/1994 |
| WO | WO 95/11301 A1 | 4/1995 |
| WO | WO 96/18733 A2 | 6/1996 |
| WO | WO 96/27006 A2 | 9/1996 |
| WO | WO 96/39426 A1 | 12/1996 |
| WO | WO 00/08140 A2 | 2/2000 |
| WO | WO 00/20432 A1 | 4/2000 |
| WO | WO 00/24885 A2 | 5/2000 |
| WO | WO 00/63364 A2 | 10/2000 |
| WO | WO 00/66724 A2 | 11/2000 |
| WO | WO 00/76497 A1 | 12/2000 |
| WO | WO 01/36646 A1 | 5/2001 |
| WO | WO 01/52904 A2 | 7/2001 |
| WO | WO 01/75164 A2 | 10/2001 |
| WO | WO 02/055692 A2 | 7/2002 |
| WO | WO 02/096927 A2 | 12/2002 |
| WO | WO 03/008573 A2 | 1/2003 |
| WO | WO 03/070910 A2 | 8/2003 |
| WO | WO 03/070969 A2 | 8/2003 |
| WO | WO 2004/022777 | 3/2004 |
| WO | WO 2004/042024 A2 | 5/2004 |
| WO | 2009111658 A2 | 9/2009 |
| WO | 2010105209 A1 | 9/2010 |
| WO | 2011017548 A1 | 2/2011 |
| WO | 2011034798 A1 | 3/2011 |

OTHER PUBLICATIONS

Ancellin et al., Extracellular export of sphinogosine kinase-1 enzyme, 2002, The Journal of Biological Chemistry, vol. 277, pp. 6667-6675.*
Charlie Schmidt, Negotiating the RNAi patent thicket, Mar. 2007, Nature Biotechnology, vol. 25, pp. 273-275.*
Elbashir et al., Analysis of gene function in somatic mammalian cells using small interfering RNAs, 2002, Methods, vol. 26, pp. 199-213.*
Hasan et al., VEGF antagonists, 2001, Expert Opinion in Biological Therapy, vol. 1, pp. 703-718.*
Dharmacon Research, siRNA oligonucleotides for RNAi applications Dharmacon siACE-RNAi options, Jul. 2001, Technical Bulletin #003, pp. 1-8.*
Bell et al., Oligonucleotide NX1838 inhibits VEGF165-mediated cellular responses in vitro, 1999, In Vitro Cellular & Developmental Biology—Animal, vol. 35, pp. 533-542.*
Keck et al., Vascular permeability factor, an endothelial cell mitogen related to PDGF, 1989, Science, vol. 246, pp. 1309-1312.*
Lewis et al., Efficient delivery of siRNA for inhibition of gene expression in postnatal mice, 2002, Nature Genetics, vol. 32, pp. 107-108.*
T.H. Rabbitts, "Chromosomal translocations in human cancer," Nature, vol. 372, No. 6502, Nov. 10, 1994, pp. 143-149.
Francesca Venturini et al., "Kinetic selection of HPV 16 *E6/E7*-directed antisense nucleic acids: anti-proliferative effects on HVP 16-transformed cells," *Nucleic Acids Research*, vol. 27, No. 7, Apr. 1, 1999, pp. 1585-1592.

(Continued)

*Primary Examiner* — Dana Shin

(74) *Attorney, Agent, or Firm* — Young & Thompson

(57) ABSTRACT

A double-strand oligonucleotide including two complementary oligonucleotide sequences forming a hybrid, each including at one of their 3' or 5' ends, one to five unpaired nucleotides forming single-strand ends extending beyond the hybrid, one of the oligonucleotide sequences being substantially complementary to a target sequence belonging to a DNA or RNA molecule to be specifically repressed, the target sequence belonging to a DNA or RNA molecule of a gene coding an angiogenic factor.

3 Claims, 14 Drawing Sheets

OTHER PUBLICATIONS

Gregg L. Semenza, "Hypoxia, Clonal Selection, and the Role of HIF-1 in Tumor Progression," *Critical Reviews in Biochemistry and Molecular Biology*, vol. 35, No. 2, Apr. 2000, pp. 71-103.

Jason R. Kennerdell et al., "Heritable gene silencing in *Drosophila* using double-stranded RNA," *Nature Biotechnology*, vol. 17, Jul. 2000, pp. 896-898.

Phillip A. Sharp, "RNA interference—2001," Genes & Development, vol. 15, 2001, pp. 485-490.

Sayda M. Elbashir et al., "RNA interference is mediated by 21- and 22-nucleotide RNAs," Genes & Development, vol. 15, No. 2, Jan. 15, 2001, pp. 188-200.

Sayda M. Elbashir et al., "Duplexes of 21-nucleotide RNAs mediate RNA interference in cultured mammalian cells," Nature, vol. 411, No. 6836, May 24, 2001, pp. 494-498.

Natasha J. Caplen et al., "Specific inhibition of gene expression by small double-stranded RNAs in invertebrate and vertebrate systems," PNAS, vol. 98, No. 17, Aug. 14, 2001, pp. 9742-9747.

Sayda M. Elbashir et al., "Knockdown of Mammalian Gene Expression Using Small Interfering RNAs," Biology of the Cell, vol. 93, No. 3-4, Oct. 2001, p. 259 (XP-002206454).

Sayda M. Elbashir et al., "Functional anatomy of siRNAs for mediating efficient RNAi in *Drosophila melanogaster* embryo lysate," The EMBO Journal, vol. 20, No. 23, Dec. 3, 2001, pp. 6877-6888.

Futami Takashi et al., "Induction of apoptosis in HeLa cells with siRNA expression vector targeted against bcl-2," Nucleic Acids Research, Supplement (2001) 2002, No. 2, pp. 251-252 (XP-002264267).

Torgeir Holen et al., "Positional effects of short interfering RNAs targeting the human coagulation trigger Tissue Factor," *Nucleic Acids Research*, vol. 30, No. 8, 2002, pp. 1757-1766.

Thomas Tuschl et al., "Small Interfering RNAs: A Revolutionary Tool for the Analysis of Gene Function and Gene Therapy," Molecular Interventions, vol. 2, Issue 3, Jun. 2002, pp. 158-167.

Joanna B. Opalinska et al., "Nucleic-Acid Therapeutics: Basic Principles and Recent Applications," Natur Reviews/Drug Discovery, vol. 1, Jul. 2002, pp. 503-514.

Ming Jiang et al., "Selective silencing of viral gene expression in HPV-positive human cervical carcinoma cells treated with siRNA, a primer of RNA interference," Oncogene, vol. 21, No. 39, Sep. 5, 2002, pp. 6041-6048.

Luis Alfonso Martinez et al., "Synthetic small inhibiting RNAs: Efficient tools to inactivate oncogenic mutations and restore p53 pathways," PNAS, vol. 99, No. 23, Nov. 12, 2002, pp. 14849-14854.

Udit N. Verma et al., "Small Interfering RNAs Directed against β-Catenin Inhibit the in Vitro and in Vivo Growth of Colon Cancer Cells," Clinical Cancer Research, vol. 9, Apr. 2003, pp. 1291-1300.

Stéphanie Filleur et al., "SiRNA-mediated Inhibition of Vascular Endothelial Growth Factor Severely Limits Tumor Resistance to Antiangiogenic Thrombospondin-1 and Slows Tumor Vascularization and Growth," Cancer Research, vol. 63, No. 14, Jul. 15, 2003, pp. 3919-3922.

Anastasia Khvorova et al., "Functional siRNAs and miRNAs Exhibit Strand Bias," Cell, vol. 115, Oct. 17, 2003, pp. 209-216.

Mark S. Duxbury et al., "EphA2: a determinant of malignant cellular behavior and a potential therapeutic target in pancreatic adenocarcinoma," Oncogene, vol. 23, 2004, pp. 1448-1456.

Mark S. Duxbury et al., "RNA interference: A mammalian SID-1 homologue enhances siRNA uptake and gene silencing efficacy in human cells," BBRC, vol. 331, 2005, pp. 459-463.

Definition of "prevent," Merriam-Webster Online Dictionary, http://m-2.com/dictionary/prevent, Nov. 24, 2006, p. 1 of 1.

Janicek et al. "p53 Interference and Growth Inhibition in p53-Mutant and Overexpressing Endometrial Cancer Cell Lines", 1977, vol. 66, pp. 94-102, *Gynecologic Oncology*.

Hirota et al., "p53 Antisenses Oligonucicotide Inhibits Growth of Human Colon Tumor and Normal Cell Lines", 1996, vol. 87, No. 7, pp. 735-742, *Jpn. J.Cancer Res.*

Gambacorli-Passeerini et al., "Blood", 1996, vol. 88, pp. 1411-1417.

Debabrata Mukhopadhyay et al., "Multiple regulatory pathways of vascular permeability factor/vascular endothelial growth factor (VPF/VEGF) expression in tumors", Seminars in Cancer Biology 14 (2004) 123-130.

Julia Glade-Bender et al., "VEGF blocking therapy in the treatment of cancer", Expert Opin. Biol. Ther. (2003) 3 (2):263-276, Ashley Publications.

Judith H. Harmey et al., "Vascular endothelial growth factor (VEGF), a survival factor for tumour cells: implications for anti-angiogenic therapy", BioEssays 24:280-283, 2002 Wiley Periodicals, Inc.

Summary of 18 studies found with search of: vegf / Closed Studies / received from Jan. 1, 1990 to Sep. 11, 2011, http://clinicaltrials.gov.

"Combination Chemotherapy With or Without Bevacizumab in Treating Patients With Metastatic Colorectal Cancer", National Cancer Institute (NCI), ClinicalTrials.gov Identifier NCT00012272, 2009.

"Bevacizumab, Cytarabine, and Mitoxantrone on Treating Patients With Hematologic Cancers", University of Maryland, ClinicalTrials.gov Identifier NCT00015951, 2009.

"Bevacizumab to Treat Kaposi's Sarcoma in HIV-Positive and HIV-Negative Patients", National Institutes of Health Clinical Center (CC), ClinicalTrials.gov Identifier NCT00055237, 2011.

"Bevacizumab to Treat Inflammatory Breast Cancer or Locally Advanced Breast Cancer", National Institutes of Health Clinical Center (CC), ClinicalTrials.gov Identifier NCT00016549, 2011.

"Study of Combined RHUMAB VEGF and Capecitabine-Based Chemoradiation for Patients With Locally Advanced Pancreatic Cancer", M.D. Anderson Cancer Center, ClinicalTrials.gov Identifier NCT00047710, 2009.

"Bevacizumab and Erlotinib in Treating Patients With Recurrent or Metastatic Head and Neck Cancer", National Cancer Institute (NCI), ClinicalTrials.gov Identifier NCT00055913, 2010.

"Efficacy and Safety Study of rhuMAb VEGF to Treat Metastatic Renal Cell Carcinoma", Genentech, ClinicalTrials.gov Identifier NCT00061178, 2005.

"Efficacy Study of ZD6474 to Treat Multiple Myeloma Cancer", AstraZeneca, ClinicalTrials.gov Identifier NCT00047788, 2009.

"VEGF Trap in Treating Patients With Solid Tumors or Non-Hodgkin's Lymphoma", National Cancer Institute (NCI), ClinicalTrials.gov Identifier NCT00045266, 2009.

"Avastin and Tarceva for Locally Advanced or Metastatic Non-Squamous Non-Small-Cell Lung Cancer", M.D. Anderson Cancer Center, ClinicalTrials.gov Identifier NCT00043823, 2011.

"SU5416 and Carboplatin to Treat Ovarian Cancer", National Institutes of Health Clinical Center (CC), ClinicalTrials.gov Identifier NCT00006155, 2008.

"Monoclonal Antibody Therapy in Treating Patients With Relapsed or Refractory Solid Tumors", National Cancer Institute (NCI), ClinicalTrials.gov Identifier NCT00005061, 2009.

\* cited by examiner

Fig. 5 A

```
1   atggaggagc cgcagtcaga tcctagcgtc gagcccctc tgagtcagga aacattttca
61  gacctatgga aactacttcc tgaaaacaac gttctgtccc cctgccgtc ccaagcaatg
121 gatgatttga tgctgtcccc ggacgatatt gaacaatggt tcactgaaga cccaggtcca
181 gatgaagctc ccagaatgcc agaggctgct cccccgtgg ccctgcacc agcagctcct
241 acaccggcgg ccctgcacc agcccctcc tggcccctgt catcttctgt cccttcccag
301 aaaacctacc agggcagcta cggtttccgt ctgggcttct tgcattctgg gacagccaag
361 tctgtgactt gcacgtactc cctgcctc aacaagatgt ttgccaact ggcaagacc
421 tgcctgtgc agctgtgggt tgattccaca ccccgccg gcacccgcgt ccgcgccatg
481 gccatctaca gcagtcaca gcacatgacg gaggttgtga ggcgtgccc ccaccatgag
541 cgctgctcag atagcgatgg tctggcccct cctcagcatc ttatccgagt ggaaggaaat
601 ttgcgtgtgg agtatttgga tgacagaaac actttcgac atagtgtggt ggtgccctat
661 gagccgcctg aggttggctc tgactgtacc accatccact acaactacat gtgtaacagt
721 tcctgcatgg ggggcatgaa ccggaggccc atcctcacca tcatcacact ggaagactcc
781 agtggtaatc tactgggacg gaacagcttt gaggtgcgtg tttgtgcctg tcctgggaga
841 gaccggcgca cagaggaaga gaatctccgc aagaaagggg agcctcacca cgagctgccc
901 ccagggagca ctaagcgagc actgcccaac aacaccagct ctctccca gccaaagaag
961 aaaccactgg atggagaata tttcaccctt cagatccgtg ggcgtgagcg cttcgagatg
1021 ttccgagagc tgaatgaggc cttggaactc aaggatgccc aggctgggaa ggagccaggg
1081 gggagcaggg ctcactccag ccacctgaag tccaaaaagg gtcagtctac ctcccgccat
1141 aaaaaactca tgttcaagac agaagggcct gactcagact ga
```

SEQ ID NO: 1

Fig. 6 A

```
   1 actacaataa ttcatgtata aaactaaggg cgtaaccgaa atcggttgaa ccgaaaccgg
  61 ttagtataaa agcagacatt ttatgcacca aaagagaact gcaatgtttc aggacccaca
 121 ggagcgaccc agaaagttac cacagttatg cacagagctg caaacaacta tacatgatat
 181 aatattagaa tgtgtgtact gcaagcaaca gttactgcga cgtgaggtat atgactttgc
 241 ttttcgggat ttatgcatag tatatagaga tgggaatcca tatgctgtat gtgataaatg
 301 tttaaagttt tattctaaaa ttagtgagta tagacattat tgttatagtt tgtatggaac
 361 aacattagaa cagcaataca acaaaccgtt gtgtgatttg ttaattaggt gtattaactg
 421 tcaaaagcca ctgtgtcctg aagaaaaagc aagacatctg gacaaaaagc aagattcca
 481 taatataagg ggtcggtgga ccggtcgatg tatgtcttgt tgcagatcat caagaacacg
 541 tagagaaacc cagctgtaat catgcatgga gatacaccta cattgcatga atatatgtta
 601 gatttgcaac cagagacaac tgatctctac tgttatgagc aattaaatga cagctcagag
 661 gagcaggatg aaatagatgg tccagctgga caagcagaac cggacagagc tcattacaat
 721 attgtaacct tttgttgcaa gtgtgactct acgcttcggt tgtgcgtaca aagcacacac
 781 gtagacattc gtacttt gga agacctgtta atgggcacac taggaattgt gtgcccatc
 841 tgttctcaga aaccateatc tacccatggct gatcctgcag gtaccaatgg ggaagagggt
 901 acggatgta atggatggtt ttatgtagag gctgtagtgg aaaaaaaaac aggggatgct
 961 atatcagatg acgagaacga aaatgacagt gatacaggtg aagatttggt agatttata
1021 gtaaatgata atgattattt aacacagyca gaaacagaga cagcacatgc gttgtttact
1081 gcacaggaag caaaacaaca tagagatgca gtacaggttc taaaacgaaa gtatttggta
1141 gtccacttag tgatattgt ggatgtgtag acaataatac tagtcctaga ttaaaagcta
1201 tatgtataga aaacaaagt agagctgcaa aaggagatt atttgaaagc gaagacagcg
1261 ggtatggcaa tactgaagtg gaactcagc agatgttaca ggtcgaaggg cgccatgaga
1321 ctgaaacacc atgtagtcag tatagtggtg gaagtggggg tggttgcagt cagtacagta
1381 gtggaagtgg gggagagggt gttagtgaaa gacacactat gttagtgcag gcacttacaa
1441 atattttaaa tgtactaaaa actagtaatg caaaggcagc aatgttagca aaatttaaag
1501 agttataccgg ggtgagtttt tcagaattag taagaccatt taaaagtaat aaatcaacgt
1561 gttgcgattg gtgtcattgct gcatttggac ttacaccccag tatagctgac agtataaaaa
1621 cactattaca acaatatgt ttatatttac acattcaaag tttagcatgt tcatggggaa
1681 tggtgtgtt actattagta agatatataaat gtggaaaaaa tagagaaaca attgaaaaat
1741 tgcctgctcaa actattatgt gtgtctccaa tgtgtatgat gatagagcct ccaaaattgc
1801 gtagtacagc agcagcatta tattggtata aaacaggtat atcaaatatt agtgaagtgt
1861 atggagacac gccagaatgg atacaaagac aaacagtatt acaacatagt tttaatgatt
1921 gtacatttga attatcacag atggtacaat gggcctacga taetgacata gtagacgata
1981 gtgaaattgc atataaatat gcacaattgg cagacactaa tagtaatgca agtgcctttc
2041 taaaaagtaa ttcacaggca aaaattgtaa aggattgtgc aacaatgtgt agacattata
2101 aacgagcaga aaaaaaacaa atgagtatga gtcaatggat aaaatataga tgtgatagag
2161 tagatgatgg aggtgattgg aagcaaattg ttatgttttt aaggtatcaa ggtgtagagt
2221 ttatgtcatt tttaactgca ttaaaaagat tttt gcaagg cataactaaa aaaaattgca
2281 tattactata tggtgcagct aacacaggta aatcattatt tggtatgagt ttaatgaaat
2341 ttctgcaagg gtctgtaata tgttttgtaa attctaaaag ccattttgg ttacaaccat
2401 tagcagatgc caaaatagt atgttagatg atgctacagt gcctgttg aactacatag
2461 atgacaattt aagaaatgca ttggatggaa atttagttc tatgatgta aagcatagac
2521 cattggtaca actaaaatgc cctcccatat taattacatc tacacattaat gctggtacag
2581 attctaggtg gcttattta cataatagat tgtggtggtt tacattcct aatgagtttc
2641 catttgacga aaacggaaat ccagtgtatg agttacatga taagaactgg aaatccttt
2701 tctcaaggac gtgtccaga ttaagtttgc acgaggacga ggacaaggaa aacgatggag
2761 actctttgcc aacgtttaaa tgtgtgtcag gacaaaatac taacacatta tgaaaatgat
2821 agtacagacc tacgtgacca tatagactat tggaaacaca tgcgcctaga atgtgctatt
2881 tattacaagg ccagagaaat gggatttaaa catattaacc accaagtggt gccaacactg
2941 gctgtatcaa agaataaagc attacaagca attgaactgc aactaacgct agaaacaata
3001 tataactcac aatatagtaa tgaaaagtgg acattacagg acgttagcct tgttagtgtat
3061 ttaactgcac caacaggatg tataaaaaaa catggatata cagtggaagt gcagtttgat
3121 ggagacatat gcaatacaat gcattataca aactggacac atatatatat ttgtgaagaa
3181 gcatcagtaa ctgtggtaga gggtcaagtt gctattatg gtttatatta tgttcatgaa
3241 ggaatacgaa catattttgt gcagtttaaa gatgatgcag aaaaatatag taaaataaa
3301 gtatgggaag ttcatgcggg tgtcaggta atattatgtc ctacatctgt gtttagcagc
3361 aacgaagtat cctctcctga aattattagg cagcacttgg ccaaccaacc cgcgcgcgaca
3421 cataccaaag ccgtcgcctt gggcacgga gaaacagaga gactatcca gcgacaaga
3481 tcagagccag acacccgaaa ccctgccac accactaagt tgttgcacag agatcagtg
3541 gacagtgctc caatcctcac tgcatttaaa gctcacaca aggacggat taactgtaat
3601 agtaacacta cacccatagt acatttaaaa ggtgatgcta atactttaaaa atgtttaaga
3661 tatagattta aaagcattg tacattgtat actgcagtgt cgtctacatg gcattggaca
3721 ggacataatg taaaacataa aagtgcattt gttacacttta catatgatga tgaatggaca
3781 cgtgaccaat tttgtctca agttaaaata ccaaaaacta ttcaagtgtc tactggattt
3841 atgtctatat gacaaatctt gatactgcat ccacaacatt actggcgtgc ttttttgcttt
3901 gctttgtgtg cttttgtgtg tctgcctatt aatacgtccg ctgcttttgt ctgtgtctac
3961 atacacatca ttaataatat tggtattact attgtggata acagcagcct ctgcgtttag
```

SEQ ID NO: 2 (PART 1)

Fig. 6 A (continued)

```
4021 gtgttttatt gtatatatta tatttgttta tattcatta ttttaatac atacacatgc
4081 acgcttttta attacataat gtatatgtac ataatgtaat tgttacatat aattgttgta
4141 taccataact tactatttt tcttttat tttcatatat aatttttt tttgtttgtt
4201 tgtttgtttt ttaataaact gttattactt aacaatgcga cacaaacgtt ctgcaaaacg
4261 cacaaaacgt gcatcggcta cccaacttta taaaacatgc aaacaggcag gtacatgtcc
4321 tcgcacatt ataccttaagg ttgaagcaa gaacaaatat tacaatatgg
4381 aagtatgggt gtatttttg gtgggttagg aattggaaca gggtcgggta caggcggacg
4441 cactgggtat attccattgg gaacaaggcc tccacagct acagatacac ttgctcctgt
4501 aagaccccct ttaacagtag atcctgtggg ccttctgat cttctatag tttctttagt
4561 ggaagaaact agttttattg atgctggtgc accaacatct gtaccttcca ttcccccaga
4621 tgtatcagga tttagtatta ctacttcaac tgataccaca cctgctatat tagatattaa
4681 taatactgtt actactgtta ctacacataa taatcccact ttcactgacc catctgtatt
4741 gcagcctcca acacctgcag aaactggagg gcattttaca ctttcatcat ccactattag
4801 tacacataat tatgaagaaa ttcctatgga tacatttatt gttagcacaa acctaacac
4861 agtaactagt agcacacca taccagggtc tcgcccagtg gcacgcctag gattatatag
4921 tcgcacaaca caacaggtta aagttgtaga cctgctttt gtaaccactc ccactaaact
4981 tattacatat gataatcctg catatgaagg tatagatgtg gataatacat tatattttc
5041 tagtaatgat aatagtatta atatagctcc agatcctgac ttttggata tagttgcttt
5101 acataggcca gcattaacct ctaggcgtac tggcattagg tacagtagaa ttggtaataa
5161 acaaacacta cgtactcgta gtggaaaatc tataggtgct aaggtacatt attattatga
5221 tttaagtact attgatcctg cagaagaaat agaattacaa actataacac cttctacata
5281 tactaccact tcacatgcag cctcactac ttctattaat aatgattat atgatattta
5341 tgcagatgac tttattacag atacttctac aacccggta ccatctgtac cctctacatc
5401 tttatcaggt tatattcctg caaatacaaac aattccttt ggtggtgcat acaatattcc
5461 ttagtatca ggtcctgata taccccattaa tatacctcctt cattaattcc
5521 tatagttcca gggtctccac aatatacaat tattgctgat gcaggtgact tttatttaca
5581 tcctagttat tacatgttac gaaaacgacg taaacgttta ccatatttt tttcagatgt
5641 ctcttggct gcctagtgag gccactgtct acttgcctcc tgtcccagta tctaaggttg
5701 taagcacgga tgaatatgtt gcacgcacaa acatatatta tcatgcagga acatccagac
5761 tacttgcagt tggacatccc tatttccta ttaaaaaacc taacaataac aaaatattag
5821 ttcctaaagt atcaggatta caatacaggg tatttagaat acatttacct gacccccaata
5881 agtttggttt tcctgacacc tcatttttata atccagatac acagcggctg gtttgggcct
5941 gtgtaggtgt tgaggtaggt cgtggtcagc cattagtgt gggcattagt ggccatcctt
6001 tattaaataa attggatgac acagaaaatg ctagtgctta tgcagcaaat gcaggtgtgg
6061 ataatagaga atgtatatct atggattaca aacaaacaca attgtgttta attggttgca
6121 aaccacctat agggaacac tgggcaaaag gatcccatg taccaatgtt gcagtaaatc
6181 caggtgattg tccaccatta gagttaataa acacagttat tcaggatggt gatatggtc
6241 atactggctt tggtgctatg gactttacta cattacaggc taacaaaagt gaagttccac
6301 tggatatttg tacatctatt tgcaaatatc cagattatat taaaatggtg tcagaaccat
6361 atgggacag cttatttttt tatttacgaa gggaacaaat gttttgttaga catttattta
6421 ataggctgg tactgttggt gaaaatgtac cagacgattc atacattaaa ggctctgggt
6481 ctactgcaaa tttagccagt tcaaattatt ttcctacaac tagtggttct atggttacct
6541 ctgatgccca aatatcaat aaacttatt ggttacaacg agcacagggc cacaataatg
6601 gcattgttg gggtaaccaa ctatttgtta ctgttgtttga tactacacgc agtacaaata
6661 tgtcattatg tgctgccata tctacttcag aaactacata taaaaatact aacttaagg
6721 agtacctacg acatggggag gaatatgatt tacagtttat ttttcaactg tgcaaaataa
6781 ccttaactgc agacgttatg acatacatac attctatgaa ttccactatt tggaggact
6841 ggaatttgg tctacaacct cccccaggag gcacactaga agatacttat aggtttgtaa
6901 cccaggcaat tgctgtcaa aaacatacac ctccagcacc taaagaagat gatccctta
6961 aaaaatacac tttttgggaa gtaaatttaa aggaaagtt ttctgcagca ctagatccagt
7021 ttccttttagg acgcaaattt ttactacaag caggattgaa ggccaaacca aaatttacat
7081 taggaaaacg aaaagctaca cccaccacct catctacctc tacaactgct aaacgcaaaa
7141 aagtaagct gtaagtattg tatgtatgt gtgttttgt gtatgttt
7201 tgtatgtt gtatgtgtt gtaaatatta agttgtatgt gtgttgtat gtatggtata
7261 ataaacacgt gtgtatgtgt ttttaaatgc ttgtgtaact attgtgcat gcaacataaa
7321 taaacttatt gttcaacac ctactaattg tgttgggtt attcattgta tataaactat
7381 attttgtaca tcctgttttt gttttatata tactatattt tgtagcgcca ggcccattt
7441 gtagcttcaa ccgaattcgg ttgcatgctt tttggcacaa aatgtgtttt tttaaatagt
7501 tctatgtcag caatatggt ttaaacttgt acgttcctg cttgccatgc gtgccaaatc
7561 cctgttttcc tgacctgcac tgcttgcaa ccattccatt gttttttaga ctgactatg
7621 tgcaactact gaatcactat gtacattgtg tcatataaaa taaatcacta tgcgccacg
7681 cctatacatac cgctgttagg cacatatttt tggcttgttt taactaacat aattgcatat
7741 ttggcataaa gtttaaactt ctaaggccaa ctaaatgtca ccctagttca tacatgaact
7801 gtgcaaaggt tagtcataca ttgttcattt gtaaactgc acatgggtgt gtgcaaacg
7861 atttttgggtt acacatttac aagcaactta tataataata ctaa
```

SEQ ID NO: 2 (PART 2)

SIRNA-BASED CANCER TREATMENT

RELATED APPLICATIONS

This is a divisional of U.S. Ser. No. 10/494,800, filed May 6, 2004, which is a §371 of International Application No. PCT/FR02/03843, with an international filing date of Nov. 8, 2002 (WO 2003/040366, published May 15, 2003), which claims priority of French Patent Application Nos. FR 01/14549, filed Nov. 9, 2001, and FR 02/04474, filed Apr. 10, 2002.

TECHNICAL FIELD

This disclosure relates to the field of the genetic investigation and treatment of human pathologies, especially cancers and infectious diseases.

BACKGROUND

Known in the prior art are antisense oligonucleotide techniques making it possible to specifically inhibit a gene in mammal cells. These techniques are based on the introduction into cells a short oligonucleotide of DNA that is complementary to the target gene. This oligonucleotide induces the degradation of the messenger RNA (mRNA) transcribed by the target gene. Another antisense technique comprises introducing into a cell a DNA oligonucleotide which forms a triple strand with the target gene. The formation of this triple strand represses the gene by either blocking access for activating proteins, or in more sophisticated approaches, by inducing degradation of the gene. None of these approaches appear to be based on a cellular mechanism existing in the cells of mammals, and they are not very effective. In fact, the clinical use of antisense has been reduced to a few rare cases, and it was believed that there was no possible use for oligonucleotides forming triple strands.

Interference RNA which is also designated "RNA'inh" or "RNAi" or cosuppression, has been demonstrated in plants. It was observed in plants that the introduction of a long double-strand RNA corresponding to a gene induced the specific and effective repression of the target gene. The mechanism of this interference comprises the degradation of the double-strand RNA into short oligonucleotide duplexes of 20 to 22 nucleotides.

The "RNA'inh" approach, more generally referred to according to the invention as inhibitory oligonucleotides or RNAi, is based on a cellular mechanism whose importance is underlined by its high degree of conservation since this mechanism is conserved throughout the plant and animal kingdoms and species, and has been demonstrated not only in plants but also in the worm *Caenorhabditis elegans* and yeasts, and mammals—humans and mice.

SUMMARY

We provide a double-strand oligonucleotide including two complementary oligonucleotide sequences forming a hybrid, each including at one of their 3' or 5' ends, one to five unpaired nucleotides forming single-strand ends extending beyond the hybrid, one of the oligonucleotide sequences being substantially complementary to a target sequence belonging to a DNA or RNA molecule to be specifically repressed, the target sequence belonging to a DNA or RNA molecule of a gene coding an angiogenic factor.

We also provide a pharmaceutical composition including as active agent at least one oligonucleotide.

We further provide a method for preventing or treating a disease resulting from expression of VEGF gene including administering the pharmaceutical composition.

We still further provide a method for preventing or treating a disease linked to hypervascularization including administering the pharmaceutical composition.

We further yet provide a method for preventing or treating a disease linked to tumoral angiogenesis including administering the pharmaceutical composition.

BRIEF DESCRIPTION OF THE DRAWINGS

FIG. 2A represents the immunodetection of VEGF in the cJ4 or LNCaP cells transfected by the control siRNA or a siRNA directed against VEGF;

FIG. 2B represents the quantification using ELISA of VEGF in conditioned medium of cj4 cells transfected by the control siRNA or the siRNA VEGF as a function of time after transfection;

FIG. 2C represents the growth curve in nude mice of tumors stemming from the subcutaneous injection of $10^6$ cells of cJ4 that is not transfected, transfected by the control siRNA or the siRNA VEGF;

FIG. 2D represents the appearance of the tumors on day 7 after injection of the cells; and FIG. 2E represents the immunodetection of VEGF in tumors stemming from the injection of cJ4 cells transfected with the control siRNA or the siRNA VEGF after 12 days of development in vivo.

FIG. 4A represents the detection by immunoblot of the expression of the androgen receptor 48 h after transfection of the LNCaP cells by a control siRNA or a siRNA directed against the androgen receptor (AR);

FIG. 4B represents the measurement of the activity of a reporter 4×ARE luciferase to R1881 in various clones of the line LNCaP not transfected, or transfected by control siRNA or by siRNA AR;

FIG. 4C represents the comparison of the response to R1881 of LNCaP cells that were not transfected (100%), and LNCaP cells transfected by a control siRNA, a siRNA directed against the androgen receptor (AR) or a siRNA recognizing specifically a punctiform mutation present in the androgen receptor of the line LNCaP;

FIG. 4D represents the growth in nude mice of tumors resulting from the subcutaneous injection of LNCaP cells transfected by a control siRNA or by a siRNA directed against the androgen receptor;

FIG. 4E represents the growth of LNCaP tumors in mice having received on the $40^{th}$ day after implantation of the cells an intravenous injection in the tail vein of 2 μg of siRNA directed against VEGF or of control siRNA; and FIG. 4F represents the growth of LNCaP tumors in mice having received on the 34th and 40th days after implantation of the tumor cells an intraperitoneal injection of 2 µg of siRNA directed against the androgen receptor or control siRNA.

FIG. 5A to FIG. 5K show the inhibition of the expression of wild or mutant forms of p53 by siRNAs and the functional consequences of these inhibitions:

FIG. 5A represents a nucleic acid sequence encoding the human p53 protein (SEQ ID NO: 1);

FIG. 5B represents the specific, dose-dependent inhibition by the siRNAs of the expression of wild or mutant forms of p53 transfected in cells not initially expressing it;

FIG. 5C represents the specific inhibition by siRNAs of the simultaneous or not simultaneous expression of wild or mutant forms of p53 transfected in cells not initially expressing it;

FIG. 5D represents the inhibition of the expression of wild endogenous p53 or a mutant form of 53 transfected by siRNA;

FIG. 5E represents the effect of the inhibition of p53 by siRNAs on the resistance to genotoxic stress;

FIG. 5J shows the inhibition by the siRNAs specific of the dependent transfection of the wild or mutant forms of p53; and FIG. 5K shows the inhibition of the expression of one of the target genes of p53, p21, inhibitory protein of cellular proliferation, by the coexpression of mutant forms of p53 and the restoration of this expression by treatment of the cells with a siRNA inhibiting the synthesis of the mutant form of p53.

FIG. 6A represents the nucleic acid sequence of papilloma virus type 16 (HPV 16) genome and the nucleic acid sequences contained therein encoding HPV proteins;

FIG. 6B represents the effect of inhibition by siRNAs specific of the expression of protein E6 of HPV in cells that express this virus, on the expression of p53 and p21; and FIGS. 6C and 6D represent the effect of the inhibition of the expression of the protein E6 of HPV on the cell cycle.

FIGS. 7A and 7B represent the effect of siRNAs DNA/RNA hybrids on the expression of the GFP expression by transfection of the cells;

FIG. 7C compares the effect of RNA/RNA, DNA/RNA and RNA/DNA siRNAs at constant dose on the inhibition of the transcription induced by the androgen receptor; and FIGS. 7D and 7E represent the effects of a substitution of RNA bases by DNA bases in the siRNA sequence inhibiting the synthesis of p53.

DETAILED DESCRIPTION

Figure 1:
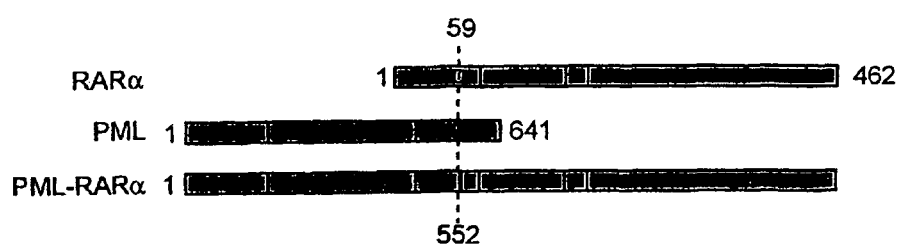
FIG. 1A is a schematic representation of the proteins RARα, PML and the associated fusion protein, PML-RARα.
FIG. 1B represents the results of transfections with an siRNA directed against PML-RARα.
Figure 1:
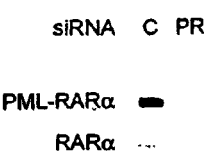

We demonstrate that the approach described in more detail herein is much more effective for specifically repressing genes as compared to the techniques employed in the prior art. Moreover, this approach can combine the advantages of antisense and the antigene properties. In one aspect, we have found that in plants cosuppression was effected at the post-transcriptional level on mature RNA and also at the transcriptional level, thus on the gene itself. In another aspect, the repression is transmitted from generation to generation and thus enables repression of a gene in a prolonged definitive manner.

Thus, the disclosure has as one aspect a double-strand oligonucleotide to be used in an interference RNA (RNAi) process, that is comprised of two complementary oligonucleotide sequences each comprising at one of their 3' or 5' ends, one to five unpaired nucleotides forming single-strand ends extending beyond the hybrid, one of said oligonucleotide sequences being substantially complementary to a target sequence belonging to a target DNA or RNA molecule which it is desired to repress specifically. This DNA or RNA can be of any type, it can be, e.g., messenger or ribosomal RNA or in one aspect the DNA of a gene.

Each of the two complementary oligonucleotide sequences advantageously comprises the same 3' or 5' end with five unpaired nucleotides forming single-strand ends extending beyond the hybrid.

In one embodiment, the two oligonucleotide sequences are advantageously substantially the same size.

Because of the base-pairing law, we designate distinctions by oligonucleotide wherein one or the other of the double-strand oligonucleotide sequences that is complementary to a target sequence belonging to a DNA or RNA molecule that is specifically repressed, can be either a single or double strand.

The oligonucleotides can be of a ribonucleotide, deoxyribonucleotide or mixed nature. In a preferred embodiment the complementary oligonucleotide of the target sequence, also designated antisense strain, is comprised primarily of a ribonucleotide. The sense strain can be of a ribonucleotide, deoxyribonucleotide or mixed nature. Examples of oligonucleotides of the invention of type RNA/RNA or DNA/RNA are given in the experimental part below.

In one preferred embodiment, the RNA/RNA hybrids are more stable than the DNA/DNA or DNA/RNA hybrids and much more stable than the single-strand nucleic acids used in the antisense strategies.

The term oligonucleotide is also understood to mean a polynucleotide of 2 to 100, more generally of 5 to 50, nucleotides of the ribonucleotide, deoxyribonucleotide or mixed type.

The part of the oligonucleotide sequence that is hybridized and complementary to the target sequence preferably is of a size comprised between 15 and 25 nucleotides, most preferably from 20 to 23 nucleotides.

The double-strand oligonucleotides comprise, preferably at the 3' end of each strand, from 1 to 5 nucleotides, preferably from 2 to 3 nucleotides, and most preferably 2 nucleotides extending beyond the hybrid. These nucleotides extending beyond the hybrid can be complementary to or not complementary to the target sequence. Thus, in a particular form of implementation of the invention, the nucleotides extending beyond the hybrid are any nucleotides, e.g., thymines.

It is possible to represent a double-strand oligonucleotide in the following manner, wherein each hyphen corresponds to a nucleotide and wherein each strand comprises at its 3' end two thymines extending beyond the hybrid:

5' - - - TT3'
3'TT - - - 5'.

The sequence of the oligonucleotides is substantially complementary to a target sequence belonging to a DNA or messenger RNA molecule of a gene which it is desired to repress specifically. Although preference is given to oligonucleotides perfectly complementary to the target sequence, the term "substantially complementary" is understood to refer to the fact that the oligonucleotide sequences can comprise several nucleotides mutated in relation to the target sequence as long as the repressive properties of the targeted gene are not changed. Thus, an oligonucleotide sequence can comprise from 1 to 3 mutated nucleotides.

These mutated nucleotides can thus be those extending beyond the hybrid or nucleotides within the oligonucleotide sequence.

In one aspect, an oligonucleotide can be a perfect hybrid or contain one or more mismatches within the double strand. Nevertheless, it is preferable that part of the oligonucleotide sequence, which is hybridized, be perfectly complementary to the target sequence whereas the nucleotides extending beyond the hybrid can be of any type and especially thymines.

The term "perfectly complementary" is understood to mean that the oligonucleotide is complementary to a sequence that belongs to a DNA or RNA of a mutated gene. The oligonucleotides can thereby enable discrimination between the sequence of the wild gene and the mutated gene present a particular value both in the analysis of the genes as well as in the therapeutic uses of the oligonucleotides.

The oligonucleotides are generally comprised of natural nucleotide bases (A, T, G, C, U) but they can also be comprised of modified nucleotides or nucleotides bearing reactive groups or bridging agents or intercalating agents that can react with the target sequence complementary to the oligonucleotide.

The oligonucleotides can be prepared by the conventional methods for the chemical or biological synthesis of oligonucleotides.

We also provide oligonucleotides coupled to substances promoting or enabling their penetration, targeting, or addressing into cells. These substances can for example include lipids, proteins, polypeptides, peptides or any other natural or synthetic substance. In fact, the oligonucleotides are intended to be internalized in the cells and, advantageously in certain cases, into the nucleus of cells where they interact with nucleic acid molecules of nucleic acids bearing the oligonucleotide target sequence. Similarly, it can be of value to promote their penetration into a particular tissue such as a tumor, bone, etc.

The oligonucleotides are useful for repressing in an effective and specific manner a gene or a set of genes, thus allowing for the treatment of numerous human pathologies. They can also be used as a research tool for the investigation and the comprehension of the gene function. We thus achieve pharmaceutical compositions comprising an oligonucleotide or a set of different nucleotides and the use of these oligonucleotides, alone or coupled to transport substances, such as a drug.

The oligonucleotides can be employed in ex vivo applications, e.g., during grafting. Thus, the oligonucleotides can be transfected into the cells, especially tumor cells, which will then be injected or they can be injected into tissues. For example, the oligonucleotides can be injected into already developed tumors via the local, systemic or aerosol route, etc. with vectorization agents.

The oligonucleotides will be used at adequate concentrations in relation to the application and the form of administration employed with suitable pharmaceutical excipients. Depending on the nature of the oligonucleotides (DNA/RNA or RNA/RNA), different doses could be used in order to obtain the desired biological effect.

The oligonucleotides are also useful as diagnostic tools making it possible to establish in vitro the genetic profile of a patient on the basis of a cell sample from the patient. The implementation of the oligonucleotides in such an analysis method makes it possible to know or to anticipate the response of the cancerous cells of this patient and to establish a personalized treatment or to adjust the treatment of a patient.

The oligonucleotides present multiple advantages compared to the conventional chemotherapeutic agents:

The RNA-RNA hybrids are more stable than the DNA-DNA or DNA-RNA hybrids and much more stable than the single-strand nucleic acids used in the antisense strategies.

Since they constitute natural compounds, there is no fear of any immunological reactions or drug-related intolerance.

The transfection experiments performed in the framework of the invention show a better penetration of the RNAi into the tumor cells than that obtained with plasmids. This point is essential in the case of tumor cells which are generally very difficult to transfect.

The experiments involving systemic injection of siRNAs in vivo show a very good penetration of these molecules into the tissues.

It is easy to mix multiple RNAi with each other in order to take as targets multiple cellular genes at the same time.

In one embodiment, the oligonucleotides and the compositions that contain them are useful for the treatment or prevention of infectious or viral diseases, such as AIDS, and the nonconventional infectious diseases, BSE and Creutzfeldt-Jakob disease. In one preferred embodiment, the oligonucleotides are suitable for treating the viral diseases at the origin of cancers. The table below presents examples of viruses implicated in cancerous pathologies in humans.

TABLE 1

| Virus | Type of associated human cancer |
| --- | --- |
| Hepatitis B virus (HBV) | Carcinoma of the liver |
| Epstein-Barr virus (EBV) | Burkitt's lymphoma, nasopharyngeal cancer, Hodgkins' disease, non-Hodgkins lymphoma, gastric cancer, breast cancer |
| Human herpes virus 8 or HHV-8/KSHV | Kaposi's sarcoma (KS), primary effusion lymphoma (PEL), multicentric Castleman's disease (MCD) |
| HPV | Neck of the uterus, head, neck, skin, nasopharynx |
| Lymphocyte T virus (HTLV) | Type T leukemia |
| Hepatitis C virus (HCV) | Carcinoma of the liver |

The oligonucleotides and the compositions containing them are also useful for the treatment or prevention of diseases linked to hypervascularization such as age-linked macular degeneration, tumoral angiogenesis, diabetic retinopathies, psoriasis and rheumatoid arthritis.

The research studies performed showed that these oligonucleotides are suitable for repressing harmful genes implicated in canceration and thus most particularly useful for the treatment or prevention of cancers and oncologic diseases in general.

An ideal anticancer treatment should lead to the death of the tumor cell while avoiding resistance phenomena. Cell death can be obtained by:

Inhibition of cellular division, blocking the cell cycle,
Induction of the apoptosis of the tumor cells,
Induction of senescence,
Induction of necrosis, Induction of differentiation. In this case, the treatment causes the cell to return to a non-cancerous state.

Thus, we provide an oligonucleotide or a set of different oligonucleotides each containing an oligonucleotide sequence complementary to a target sequence belonging to a molecule of DNA or messenger DNA of a gene whose repression induces apoptosis, or senescence or necrosis or the differentiation of the tumor cells or prevents their division or more than one of these phenomena.

Induction of apoptosis of tumor cells is based on the fact that the function of numerous cellular genes (e.g., members of the family BCL2, BCL XL) is to protect the cells from apoptosis. The loss of expression of these genes induced by RNAi enables passage into apoptosis.

Cell death can also be induced by the loss of adhesion of the cells to the matrix (anoikis). This effect can be obtained by disturbing the balance between proteases and protease inhibitors in the tumors and their stromal environment. This disturbance can also diminish the capacities of tumor cells to invade healthy tissues and metastasize. The siRNAs can thus be used to prevent the synthesis of proteins of the families of the matrix metalloproteases (MMP), membranous matrix metalloproteases, their inhibitors (TIMPs) as well as activators of the protease inhibitors such as, PAI-1, and the proteases themselves such as, urokinase.

Induction of senescence is based on the fact that normal cells can only divide a limited number of times. This number is programmed, for example circa 50 divisions for embryonic fibroblasts. Senesence can also be measured by the length of the telomeres, which get shorter as the cellular divisions advance. Below a certain size, the telomeres are no longer functional and the cell, incapable of division, enters into senescence. However, in germinal cells, this length is maintained constant by the action of an enzyme, telomerase. Telomerase is re-expressed in numerous cancers which enables the tumor cells to multiply indefinitely. A RNAi blocking the expression of telomerase would be without consequence on normal somatic cells and would lead tumor cells into senescence.

Blocking cell division also leads cells to senescence. Blockage can be obtained by inhibiting the essential cellular receptors. Depending on the nature of the cell, these receptors can belong to the class of receptors known as the growth factors (notably, EGF, SST2, PDGF, FGF), whether or not they are mutated, or to the nuclear receptors of hormones (notably, androgens, estrogens, glucocorticoids).

The hormone receptors are frequently mutated in cancers and pertains, in this case, to the use of oligonucleotides recognizing the mutated forms of these receptors, which do not inhibit the synthesis of the wild forms. This makes it possible, for example, in the case of prostate carcinomas that have become resistant by mutation of the androgen receptor, to treat patients via the systemic route with siRNAs that block the synthesis of the mutated receptor without inducing the castration effects linked to the inhibition of the wild forms of the receptor in other organs. In fact, the Applicants' present an example using oligonucleotides recognizing mutated forms of the receptor.

The cell cycle can also be stopped by inhibiting the synthesis of proteins indispensable for its unfolding such as, for example, cyclins, cyclin-dependent kinases, DNA-replication enzymes, transcription factors such as E2F.

Induction of necrosis results from the requirement of the tumor cells for oxygen and nutriments. A tumor initially provides for its development from the preexisting vessels of the host. Beyond 1 to 2 mm in diameter, the cells located at the center of the tumor are in hypoxia. This hypoxia, via the intermediary of a proline hydroxylase, leads to the stabilization of the transcription factor Hif1α, whose sequence, SEQ ID NO. 59, is presented in the attachment, which by attaching itself on the HRE sequences in the promoters of its target genes triggers the hypoxic reaction. This reaction leads to the activation of about a hundred genes enabling activation, notably of the pathway of anaerobic glycolysis, which is the stress response, and angiogenesis. This latter mechanism activates the VEGF gene, whose sequence, SEQ ID NO. 60, is presented in the attachment, which is the principal tumoral angiogenic factor.

The oligonucleotides block, for example, the expression of the transcription factor Hif1α or, for example, that of VEGF making the tumor cells incapable of mounting a hypoxic or angiogenic response. Angiogenesis is a mechanism that is normally repressed in the adult with the exception of the menstrual cycle (uterus ovaries). The inhibition of this mechanism therefore has few consequences for normal tissues.

We also provide an oligonucleotide of which one of the oligonucleotide sequences is substantially complementary to a target sequence belonging to a molecule of DNA or messenger RNA of the gene coding:

the transcription factor Hif1α;
one or more isoforms of VEGF A or a member of the family of this growth factor.

In certain cancers, the tumoral phenotype results from or is maintained by the expression of a protein normally absent from normal cells. This protein can result from the present or prior expression of a viral genome in the cell such as that of the papilloma virus (HPV) or the hepatitis B virus. This protein can also result from the mutation (punctiform, deletion, insertion) of a normal cellular gene. In this case, it is frequent that the mutated protein thereby produced possesses negative transdominant properties in relation to the normal protein. The specificity of the siRNA enables inhibition of the synthesis of the mutant protein without blocking the synthesis of the wild proteins. Two examples relating to the mutated form of the protein p53 and the androgen receptor are reported in the experimental section below.

The research studies performed demonstrate that these oligonucleotides are particularly suitable in one embodiment for repressing harmful genes implicated in canceration and more particularly those genes leading to the formation of fusion proteins in cancerous cells, such as the fusion protein PML-RAR alpha.

Thus in one embodiment, we provide an oligonucleotides whose sequence is complementary to a target sequence belonging to a gene resulting from a chromosomal translocation so as to inhibit the effects of the fusion protein expressed by this gene. Thus, the target sequence corresponds to the sequence of the junction of the fusion protein.

Table 2 is a nonexhaustive list of the fusion proteins representing therapeutic or diagnostic targets for the oligonucleotides.

TABLE 2

| Disease | Fusion protein | Chromosomal translocation | References |
|---|---|---|---|
| APL (acute promyelocytic leukaemia) | PML-RARalpha | t(15; 17)(q22; q21) | De The et al. Cell 1991, 66: 675 |
| | PLZF-RARalpha | t(11; 17)(q23; q21) | Chen Z et al. EMBO J 1993, 12: 1161 |
| | NPM-RARalpha | t(5; 17)(q32; q12) | Redner RL et al. Blood 1996, 87: 882 |
| | NuMA-RARalpha | t(5; 17)(q13; q21) | Wells RA et al. Leukemia 1996, 10: 735 |
| | STAT5beta/RARalpha | | Arnould C et al. Hum. Mol. Genet. 1999, 8: 1741 |
| ALL (acute lymphoblastic leukaemia) | TEL-AML1 | t(12; 21)(p13; q22) | |
| | BCR/ABL | t(9; 22)(q34; q11) | |
| | MLL/AF4 | t(4; 11)(q21; q23) | Domer PH et al. Proc Natl Acad Sci USA 1993, 90: 7884-8 |
| | ALL-translocation | t(12; 21)(q12; q22) | |
| | CALM/AF10 | t(10; 11)(p12-p13; q14-q21) | Dreyling MH et al. Proc Natl Acad Sci USA 1996, 93: 4804 |
| | ALL1/AF4 | t(4; 11) | Janssen JW et al. Blood 1994, 84: 3835 |
| | E2A/HLF | t(17; 19)(q22; p13) | Hunger SP et al. Genes Dev 1992, 6: 1608 |
| AML (acute myeloid leukemia) | TLS/FUS-ERG | t(16; 21)(p11; q22) AML(M7) | Ichikawa H et al. Cancer Res 1994, 54: 2865 |
| | MLL-AF10 | t(10; 11)(p12-p13; q23) | Borkhardt A et al. Leukemia 1995, 9: 1796 |
| | MLL-AB11 | t(10; 11) | Shibuya et al. Genes Chromosomes Cancer 2001, 32: 1 |
| | HLXB9-ETV6 | t(7; 12)(q36; p13) | Beverloo et al. Cancer Res 2001, 61: 5374 |
| | MLL-ELL | t(11; 19)(q23; p13.1) | Rubnitz JE et al. Blood 1996, 87: 4804 |
| | CBFbeta/MYH11 | inv[16] | Tobal K et al. Br J Haematol 1995, 91: 104 |
| | AML1-MTG8 | t(8; 21) | Miyoshi et al. EMBO J 1993, 12: 2715 |
| | TEL-TRKC | t(12; 15)(p13; q25) | Eguch et al. Blood, 1999, 93: 1355 |
| | AML1/ETO | t(8; 21) | Kusec R et al. Leukemia, 1994, 8: 735 |
| | CALM/AF10 | t(10; 11)(p12-p13; q14-q21) | Dreyling MH et al. Proc Natl Acad Sci USA 1996, 93: 4804 |
| | ETV6-BTL | t(4; 12)(q11-q12; p13) | Cools et al. Blood 1999, 94: 1820 |
| | CBFbeta-SMMHC | inv(16)(p13; q22) | Wijmenga C et al. Proc Natl Acad Sci USA 1996, 93: 1630 |
| | FUS/ERG | t(16; 21)(p11; q22) | Panagopoulos I et al. Genes Chromosomes Cancer, 1994, 11: 256 |
| | DEK/CAN | t(6; 9)(p23; q34) | on Lindern M et al. Mol Cell Biol, 1992, 12: 1687 |
| | MLL-AF9 | t(9; 11)(p22; q23) | Super HJ et al. Blood, 1995, 85: 855 |
| | MLL-ENL | (11q23) | Schreiner SA et al. Leukemia 1999, 13: 1525 |
| | MLL-AF4 | t(4; 11)(q21; q23) | Domer PH et al. Proc Natl Acad Sci USA 1993, 90: 7884 |
| | MLL-AF6 | t(6; 11)(q27; 23) | Tanabe S et al. Genes Chromosomes Cancer 1996, 15: 206 |
| | MLL-AF17 | t(11; 17)(q23; q21) | Prasad R et al. Proc Natl Acad Sci USA 1994, 91: 8107 |
| | MLL-AFX | t(X; 11)(q13; q23) | Borkhardt A et al. Oncogene 1997, 14: 195 |
| | MLL-AF1p | | So CW et al. Leukemia 2000, 14: 594 |
| | MLL-AF1q | t(1; 11)(q21; q23) | Busson-Le Coniat M et al. Leukemia 1999, 13: 302 |
| | MLL self | | So CW et al. Cancer Res 1997, 57: 117 |
| | MLL-CBP | t(11; 16)(q23; p13) | Taki T et al. Blood 1997, 89: 3945 |
| | AML1-ETO | t(8; 21) | Erickson P et al. Blood 1992, 80: 1825 |
| MDS/AML (myelodysplasia/acute myeloid leukemia) | NPM-MLF1 | t(3; 5)(q25.1; q34) | Yoneda-Kato N et al. Oncogene 1996, 12: 265 |
| CML (chronic myelogenous leukemia) | Bcr-Abl/p210 | | Ben-Neriah Y et al. Science 1986, 233: 212 |
| | AML1-MDS1-EVI1 (AME) | t(3; 21)(q26; q22) | Fears S et al. Proc Natl Acad Sci USA 1996, 93: 1642 |
| BpALL (cell acute lymphoblastic leukemia) | TEL-AML1 | t(12; 21)(p13; q22) | Golub TR et al. Proc Natl Acad Sci USA 1995, 92: 4917 |
| MPD (myeloproliferative disease) | TEL-JAK2 | t(9; 12)(p24; q13) | Lacronique et al. Science 1997, 278: 1309 |
| | TEL-PDGFbetaR | t(5; 12)(q33; p13) | Jousset C et al. EMBO J, 1997, 16: 69 |
| | TEL-TRKC | t(12; 15)(p13; q25) | Eguch et al. Blood, 1999, 93: 1355 |
| CMML (chronic myelomonocytic leukemia) | involving PDGFbetaR | t(5; 17)(q33; p13) | Magnusson et al. Blood 2001 98: 2518 |
| | HIP1/PDGFbetaR | t(5; 7)(q33; q11.2) | Ross TS et al. Blood 1998, 91: 4419 |
| | TEL/PDGFbetaR | t(5; 12)(q33; p13) | Tomasson MH et al. Blood, 1999, 93: 1707 |
| MALT (gastric mucosa-associated lymphoid tissue lymphoma) | API2-MALT1 | t(11; 18)(q21; q21) | Motegi M et al. Am J Pathol 2000, 156: 807 |
| ALCL (anaplastic large cell lymphoma) | NPM-ALK | t(2; 5)(p23; q35) | Waggott W et al. Br J Haematol 1995, 89: 905 |
| | SU-DHL-1 | t(2; 5) | Siminovitch KA et al. Blood 1986, 67: 391 |
| | ATIC-ALK | inv(2)(p23q35) | Colleoni GW et al. Am J Pathol 2000, 156: 781 |
| | ALK-related translocation | t(2; 17)(p23; q25) | Maes et al. Am J Pathol 2001, 158: 2185 |
| MPD (myeloproliferative disease) | NUP98-HOXA9 | t(7; 11)(p15; p15) | Nakamura T et al. Nat Genet 1996, 12: 154 |
| APP (amyloid precursor protein) in sporadic Alzheimer's disease (AD) or Down's syndrome | APP + 1 (38-kDa) | | Hersberger et al. J Neurochem 2001 76(5): 1308-14 |
| primary pleural monophasic synovial sarcomas (SS) | SYT-SSX1 | t(X; 18)(p11.2; q11.2) | Crew AJ et al. EMBO J 1995, 14: 2333 |
| | SYT-SSX2 | t(X; 18)(p11.2; q11.2) | Crew AJ et al. EMBO J 1995, 14: 2333 |
| Dermatofibrosarcoma protuberans (DP) | COL1A1/PDGFB rearrangement | t(17; 22) | O'Brien KP et al. Genes Chromosomes Cancer 1998, 23: 187 |
| ARMS (pediatric alveolar rhabdomyosarcoma) | EWS-FLII | | Athale et al. J Pediatr Hematol Oncol 2001, 23: 99 |
| | EWS-ERG | t(11; 22)(q24; q12) | Sorensen PH et al. Nat Genet 1994, 6: 146 |
| | PAX3-FKHR | t(2; 13)(q35; q14) | Fredericks WJ et al. Mol Cell Biol 1995, 15: 1522 |

TABLE 2-continued

| Disease | Fusion protein | Chromosomal translocatian | References |
|---|---|---|---|
| ESFT (Ewing sarcoma family of tumors) | PAX7-FKHR | t(1; 13)(p36; q14) | Barr FG et al. Hum Mol Genet 1996, 5: 15 |
| | EWS-WTI | t(11: 22)(p13: q12) | Benjamin et al. Med Pediatr Oncol 1996 27(5): 434-9 |
| DSRCT (desmoplastic small round cell tumors) | EWS/FI-1 | t(11-22)(q24; q12) | Fidelia-Lambert et al. Hum Pathol 1999, 30: 78 |
| MM (multiple myeloma) | IGH-MMSET | t(4; 14)(p16.3; q32) | Malgeri et al. Cancer Res 2000 60: 4058 |
| MPD (stem cell myeloproliferative disorder) | FGFR1-CEP110 | t(8; 9)(p12; q33) | Guasch et al. Blood 2000 95: 1788 |
| Ewing sarcoma (ES)-peripheral primitive neuroectodermal tumor (pPNET) | EWS-FEV | t(2; 22)(q13; q22, t(3; 18)(p21; q23) | Llombart-Bosch et al. Diagn Mol Pathol 2000, 9: 137 |
| | EWS-FLI1 | t(11; 22; 14)(q24; q12; q11) | Bonin G et al. Cancer Res 1993, 53: 3655 |
| | EWS-ERG | t(21; 22)(q22; q12) | Sorensen PH et al. Nat Genet. 1994, 6: 146 |
| | ETV6/CBFA2 | t(12; 21)(p12; q22) | Fears S et al. Genes Chromosomes Cancer 1996, 17: 127 |
| MLS (myxoid liposarcomas) | FUS/CHOP | t(12; 16)(q13; p11) | Rabbitts TH et al. Nat Genet 1993, 4: 175 |
| | EWS/CHOP | t(12; 22; 20)(q13; q12; q11) | Zinszner H et al. Genes Dev 1994, 8: 2513 |

Targeting the junction between two genes with an oligonucleotide, for example, the two genes pml and rarα, makes it possible to attain specific inhibition of the fusion protein without affecting the biological role of the natural proteins which can be coded by the second allele. This form of implementation thus encompasses all of the fusion proteins implicated in carcinogenesis, particularly the leukemias. Further, the reciprocal forms as well as all of the variants of the fusion proteins cited in the attachment also constitute targets. In one embodiment, we provide for the use of oligonucleotides, as described above, for the preparation of a pharmaceutical composition intended for the treatment of diseases resulting from the expression of a fusion protein, and in particular for the treatment of cancers.

The present anticancer therapies target the cancerous cells, by different approaches that are employed in isolation or combined with each other (chemotherapy, surgery, radiotherapy, immunotherapy). The therapeutic failures are massively due to either the cells not having been reached by the treatment or, primarily, by cells that are mutated in response to the treatment. The capacity for mutation is greatly facilitated by the genetic instability of the tumor cells. The inhibition of tumor vascularization, depriving the cells of oxygen and nutriments, has in the past several years opened new therapeutic perspectives in cancer research. This strategy, which is complementary to the previously mentioned methods, targets the normal endothelial cell of the host, which is genetically stable and theoretically not likely to mutate. Numerous clinical trials directed at inhibiting tumoral angiogenesis via different approaches are underway worldwide. However, the initial reported results appear to be rather disappointing.

We demonstrated that tumors are capable of compensating for the effects of angiogenesis inhibitors by selecting subpopulations of cells secreting strong concentrations of pro angiogenic factors.

Tumors are not comprised of homogeneous cells with regard to their genetic expression. This is attested to by a very large number of studies in which immunolabeling was performed for a large variety of antigens in the tumors. Macroscopically, a tumor is frequently composed of regions that are highly vascularized alongside zones of necrosis or avascular regions.

This tumor heterogeneity promotes the ability of tumors to escape from the applied treatments, no matter what their nature. The greater the diversity of the genetic expression in a tumor, the greater the probability that there exists at least one cell capable of resisting an antitumor agent. It therefore appears to be essential to combine different strategies in order to first reduce the tumoral heterogeneity and avoid the escape phenomena.

We also provide siRNAs that are inhibit the expression of genes responsible for the inactivation of p53 and their use in the treatment of cancers. p53 is the product of a tumor-suppressor gene or anti-oncogene, mutated in more than 50% of the tumors in humans. p53 is thus considered to be a guardian of the genome. It is activated in the cells in the case of genotoxic stress and participates in various processes including the induction of the programmed death process.

In 74% of the cases of monoallelic mutation, the inactivation of p53 is due to a punctiform mutation leading to the expression of protein that is mutated but of normal size. It is generally considered that the mutated version forms heteromers with the product of the wild allele on which it acts as a negative transdominant that blocks its activity. The mutant form also appears to have an oncogenous activity in itself. Thus, the mutated forms of p53 are capable of activating the gene MDR, which facilitates the resistance of the cancerous cells to chemotherapy. Moreover, the expression of mutants of p53 is associated with a stronger tumoral angiogenesis, probably because the mutant forms of p53 are no longer capable of stimulating the transcription of the gene of thrombospondin, one of the most powerful repressors of angiogenesis, and activate VEGF and bFGF, two powerful activators of angiogenesis. Moreover, the cells in which a mutated form of p53 is expressed lose various levels of regulation. In particular, they are no longer capable of initiating a programmed death process which constitutes one of the major protection processes against tumorigenesis. The restoration of wild type p53 activity in cultured tumor cells leads to the restoration of this cellular response. Thus, inhibiting the expression of the mutated forms of p53 represents a potentially powerful tool in anticancer therapy.

At present, there is no effective means for restoring p53 activity in human cancer cells. With regard to the cancers in which both alleles are inactivated, attempts to restore the p53 activity by gene therapy are envisaged. These approaches are complicated by the use of viral vectors that at present do not appear to be very effective.

Furthermore, it has been observed specifically in cervical cancers linked to infection by the HPV virus of the cells of the neck of the uterus that p53 can be inactivated by the overexpression of a viral protein. In fact, this virus codes for a protein, the protein E6, which inactivates p53. In this type of cancer, it is the inhibition of the protein E6 which could restore a wild p53 activity.

We provide new means enabling activation of p53 by inhibiting the expression of the genes responsible for its inactivation. The research studies performed demonstrated that it was possible to repress in a very effective and very specific manner the expression of a mutant form of p53.

We provide oligonucleotides presenting a sequence complementary to a specific polynucleotide sequence of the gene of the mutated p53. Thus, these are oligonucleotides whose sequence bear a mutation in relation to the sequence of wild p53. The sequence of the wild gene of p53 is shown in the attached sequence listings as SEQ ID NO. 1. The different mutations that can intervene in the sequence of p53 are indicated in Table 3.

TABLE 3

| Codon | Event | Codon | Event | Codon | Event | Codon | Event | Codon | Event |
|---|---|---|---|---|---|---|---|---|---|
| 248 | G->A | 129 | C->A | 189 | C->G | 217 | Stop at 219 | 202 | Ins |
| 248 | C->T | 281 | A->G | 290 | G->T | 239 | Stop at 259 | 247 | Ins |
| 282 | C->T | 293 | Fr. | 136 | Stop at 169 | 187 | G->C | 171 | Ins |
| 175 | G->A | 157 | DEL | 201 | Stop at 208 | 273 | Stop at 343 | 203 | Ins |
| 196 | C->T | 161 | C->A | 275 | Stop at 344 | 182 | C->T | 290 | Stop at 303 |
| 213 | G->A | 195 | A->T | 132 | Stop at 148 | 263 | Stop at 344 | 233 | del |
| 234 | T->C | 197 | G->C | 176 | Stop at 180 | 307 | Stop at 344 | 210 | Stop at 244 |
| 237 | T->G | 342 | Fr. | 191 | del | 261 | Stop at 344 | 201 | G->A |
| 244 | G->T | 135 | G->C | 218 | G->A | 285 | Stop at 344 | 92 | Ins |
| 256 | A->G | 145 | T->A | 234 | T->A | 159 | G->A | 44 | Fr. |
| 259 | A->G | 276 | G->C | 136 | C->A | 168 | C->T | 109 | ins |
| 260 | T->G | 173 | G->T | 245 | G->C/G->A | 230 | C->T | 279 | G->A/G->A |
| 245 | G->T | 270 | T->G | 126 | Stop at 148 | 228 | A->C | 168 | Stop at 170 |
| 278 | C->T | 158 | G->C | 259 | G->C | 230 | C->A | 153 | Stop at 178 |
| 134 | T->A | 152 | Fr. | 171 | G->C | 287 | Stop at 300 | 247 | C->A |
| 194 | C->T | 132 | G->T | 197 | T->A | 269 | Stop at 343 | 272 | Stop at 305 |
| 273 | G->A | 288 | A->C | 236 | T->G | 227 | Stop at 227 | 137 | Stop at 169 |
| 309 | C->T | 247 | A->T | 239 | C->A | 231 | Stop at 238 | 148 | Stop at 180 |
| 274 | T->A | 273 | G->C | 288 | A->T | 275 | G->C | 157 | Stop at 180 |
| 156 | G->C | 283 | G->C | 161 | Fr. | 142 | T->C | 191 | Stop at 208 |
| 245 | G->A | 109 | Fr. | 164 | Fr. | 312 | C->G | 243 | Stop at 260 |
| 193 | A->G | 174 | G->C | 142 | Stop at 148 | 282 | C->G/G->C | 251 | C->A |
| 229 | T->A | 300 | C->G | 240 | A->C | 235 | Stop at 244 | 242 | C->A |
| 237 | G->A | 205 | A->G | 137 | T->C | 156 | Stop at 179 | 244 | C->A |
| 277 | G->T | 224 | G->T | 100 | G->A | 207 | A->G | 239 | C->G |
| 194 | T->G | 168 | A->T | 106 | C->G | 179 | Stop at 246 | 142 | T->A |
| 242 | G->C | 167 | Fr. | 215 | A->G | 210 | Stop at 214 | 248 | C->A |
| 246 | G->C | 136 | C->G | 246 | Fr. | 315 | T->C | 177 | Stop at 246 |
| 68 | G->T | 164 | A->C | 117 | G->A | 229 | Stop at 229 | 296 | Fr. |
| 147 | T->A | 179 | C->G | 271 | Stop at 344 | 167 | A->C | 303 | C->T |
| 151 | C->A | 187 | G->T | 324 | T->G | 256 | Stop at 343 | 140 | C->A |
| 209 | A->T | 201 | Stop at 246 | 346 | Fr. | 176 | Stop at 176 | 268 | C->T |
| 213 | C->T | 213 | C->A | 174 | Stop at 246 | 309 | Stop at 336 | 254 | A->C |
| 214 | A->G | 238 | G->T | 170 | Stop at 177 | 270 | Stop at 344 | 291 | G->A |
| 248 | G->T | 113 | T->G/C->T | 234 | T->G | 129 | G->A | 139 | Stop at 148 |
| 266 | G->T | 143 | G->T | 354 | A->G | 46 | Stop at 50 | 251 | A->G |
| 273 | C->T | 160 | G->T | 259 | Stop at 344 | 160 | T->G | 221 | Stop at 224 |
| 273 | G->T | 198 | G->T | 319 | Stop at 344 | 56 | A->T | 237 | A->T/G->T |
| 282 | C->G | 203 | G->T | 332 | Ins | 74 | Stop at 144 | 234 | Stop at 234 |
| 334 | G->T | 238 | T->A | 340 | Ins | 118 | A->G | 215 | T->A |
| 342 | C->T | 272 | G->C | 177 | del | 257 | del | 191 | T->A |
| 132 | A->C | 276 | Ins | 179 | T->A | 192 | G->T | 290 | C->A |
| 249 | G->C | 277 | T->G | 190 | Stop at 246 | 294 | G->T/G->C | 60 | A->T |
| 280 | G->A | 302 | G->T | 254 | Ins | 240 | del | 93 | C->A |
| 285 | G->A | 131 | C->G | 194 | C->A | 306 | G->T | 143 | T->C/G->C |
| 241 | C->T | 168 | A->G | 172 | T->A | 175 | C->G/G->A | 319 | G->T |
| 249 | G->T | 258 | G->T | 173 | G->T/T->G | 246 | Stop at 261 | 110 | Stop at 122 |
| 158 | G->A | 278 | C->A | 261 | T->C | 279 | Stop at 305 | 190 | T->G |
| 163 | T->C | 285 | G->C | 266 | A->G | 146 | T->G/G->T | 192 | C->G |
| 176 | G->A | 287 | G->A | 199 | Fr. | 154 | Stop at 169 | 126 | T->G/A->G |
| 206 | Fr. | 294 | Fr. | 236 | C->G | 132 | del | 273 | Stop at 305 |
| 234 | A->G | 236 | Fr. | 168 | C->G | 175 | Stop at 175 | 266 | Stop at 344 |
| 238 | G->A | 301 | Ins | 201 | G->C | 152 | Stop at 165 | 64 | Stop at 122 |
| 254 | A->G/T->A | 228 | A->G | 203 | Stop at 208 | 260 | Stop at 262 | 103 | C->A |
| 287 | G->T | 175 | Fr. | 250 | C->A/C->G | 194 | Stop at 246 | 343 | A->G |
| 143 | Fr. | 282 | G->T | 283 | G->T | 170 | C->A | 317 | Stop at 344 |
| 205 | A->T | 152 | Stop at 180 | 256 | C->A | 213 | C->G | 125 | Stop at 148 |
| 262 | Fr. | 177 | C->G | 245 | C->T | 213 | A->C | 239 | A->G/C->T |
| 171 | G->T | 216 | T->A | 342 | G->C | 232 | A->G | 119 | Fr. |
| 126 | C->G | 232 | T->G | 243 | G->A | 294 | G->C | 162 | T->G/C->G |
| 138 | Fr. | 275 | Stop at 305 | 296 | A->G | 240 | T->A | 12 | C->A/C->G |
| 223 | C->T | 216 | G->T | 68 | G->C | 223 | C->G | 247 | C->G |
| 274 | G->T | 137 | Fr. | 102 | C->T | 171 | A->C | 190 | T->A |
| 218 | Fr. | 251 | T->G | 104 | G->C | 328 | T->G | 240 | T->C |
| 246 | A->G | 252 | Ins | 117 | G->C | 150 | C->T | 315 | C->T |
| 250 | Fr. | 254 | T->A | 175 | Stop at 246 | 252 | C->A | 313 | C->T |
| 143 | T->C | 49 | G->C | 138 | Stop at 169 | 256 | Stop at 342 | 42 | G->T |

TABLE 3-continued

| Codon | Event | Codon | Event | Codon | Event | Codon | Event | Codon | Event |
|---|---|---|---|---|---|---|---|---|---|
| 173 | G->A | 53 | G->T | 215 | T->G | 200 | Stop at 246 | 73 | G->T |
| 242 | G->T | 60 | C->T | 247 | Stop at 262 | 239 | del | 231 | C->A |
| 190 | Fr. | 202 | G->T | 104 | C->T | 215 | A->T | 172 | Stop at 173 |
| 246 | T->C | 204 | A->G | 297 | A->C | 147 | Stop at 169 | 211 | Stop at 214 |
| 157 | G->T | 265 | T->A | 252 | T->C | 276 | G->A | 150 | Stop at 180 |
| 239 | Fr. | 135 | T->C | 276 | C->T | 210 | A->C | 145 | C->A |
| 240 | A->T | 147 | G->A | 349 | A->C | 182 | T->C | 335 | C->G |
| 238 | T->C | 153 | C->T | 173 | G->A/T-> | 161 | G->A/C->T | 285 | G->A/A->G |
| 35 | Stop at 42 | 170 | G->T | | G/G->T | 83 | C->A | 85 | Stop at 122 |
| 47 | C->T | 260 | C->T | 225 | G->C | 304 | Stop at 344 | 98 | C->T |
| 89 | Fr. | 255 | Stop at 263 | 250 | del | 225 | ins | 113 | C->T |
| 102 | Fr. | 139 | G->C | 224 | A->G | 314 | Stop at 344 | 87 | Stop at 148 |
| 141 | C->G | 234 | A->C | 166 | T->A | 301 | A->G | 97 | C->T |
| 144 | C->T | 152 | C->A | 156 | C->A | 224 | G->A | 217 | Stop at 246 |
| 146 | G->A | 170 | C->T | 291 | A->G | 112 | C->G | 226 | G->T |
| 158 | G->T | 175 | G->C | 305 | A->G | 163 | C->A | 278 | T->A |
| 161 | G->A | 240 | A->G | 306 | A->T | 299 | T->A | 145 | C->T |
| 164 | G->T | 259 | G->T | 296 | C->T | 251 | del | 133 | Stop at 148 |
| 165 | Ins | 87 | Fr. | 267 | del | 162 | Stop at 180 | 136 | A->C |
| 176 | C->G | 142 | Fr. | 151 | Stop at 169 | 44 | G->T | 239 | A->T/C->A |
| 191 | Fr. | 175 | C->G | 228 | Stop at 238 | 177 | C->A/C->T | 245 | G->A/G->A |
| 215 | G->T | 126 | A->G | 165 | Stop at 180 | 236 | A->C | 252 | T->A |
| 217 | G->T | 128 | T->G | 176 | C->A | 243 | T->C | 244 | G->A/C->A |
| 220 | A->G | 128 | C->T | 192 | A->G | 137 | G->A | 299 | Stop at 305 |
| 224 | G->C | 134 | T->C | 167 | Ins | 218 | G->C | 305 | A->T/G->A |
| 242 | C->G | 172 | Fr. | 166 | T->C | 277 | G->C | 310 | A->C |
| 259 | A->T | 237 | T->A | 120 | A->G | 54 | Fr. | 322 | C->G |
| 267 | G->C | 193 | A->C | 150 | C->A | 40 | Ins | 323 | Stop at 344 |
| 291 | A->T | 213 | Fr. | 155 | A->C | 156 | Stop at 166 | 315 | C->G |
| 298 | G->T | 246 | G->A | 203 | Stop at 246 | 168 | C->G/A->T | 308 | G->C |
| 182 | C->A | 235 | Fr. | 221 | A->G | 249 | G->T/G->T | 323 | T->G |
| 233 | Stop at 239 | 329 | Fr. | 50 | Stop at 109 | 158 | C->A | 201 | T->A |
| | | 155 | A->G | 191 | Stop at 243 | 209 | G->T | 190 | T->C |
| 173 | T->C | 7 | G->C | 205 | T->C | 184 | Stop at 207 | 278 | T->C |
| 251 | A->C | 56 | G->T | 210 | Stop at 246 | 146 | G->T | 305 | G->C |
| 219 | Fr. | 104 | C->T | 110 | C->G | 250 | C->A | 176 | del |
| 280 | A->T | 245 | G->A/G->A | 166 | C->A | 74 | Stop at 122 | 217 | T->G |
| 126 | T->A | 317 | C->T | 269 | G->T | 225 | del | 174 | A->C |
| 132 | G->C | 125 | G->A | 155 | Stop at 179 | 253 | C->A | 289 | C->G |
| 181 | C->T | 214 | Fr. | 155 | Stop at 169 | 269 | INS | 234 | C->G |
| 184 | G->T | 248 | G->C | 156 | Stop at 169 | 184 | T->C | 232 | A->C |
| 220 | T->C | 307 | Ins | 162 | C->T | 304 | T->G | 317 | A->T |
| 266 | G->A | 152 | G->T | 196 | A->G | 204 | A->C | 132 | Fr. |
| 279 | G->A | 178 | C->G | 213 | Stop at 246 | 66 | Stop at 145 | 299 | Fr. |
| 305 | Ins | 253 | C->T | 214 | C->T | 259 | Stop at 263 | 158 | C->G/G->T |
| 220 | A->C | 270 | T->C | 269 | C->T | 263 | Stop at 271 | 142 | Stop at 169 |
| 284 | A->C | 281 | C->A | 287 | A->G | 280 | Stop at 344 | 203 | Stop at 207 |
| 280 | G->C | 216 | Fr. | 313 | C->G | 237 | Stop at 246 | 248 | G->C/G->C |
| 172 | Stop at 231 | 131 | Fr. | 108 | Stop at 144 | 289 | C->A | 256 | A->C |
| | | 141 | Ins | 321 | A->G | 315 | Stop at 344 | 262 | Stop at 343 |
| 174 | Stop at 176 | 140 | Fr. | 244 | C->T | 312 | C->T | 301 | Stop at 343 |
| | | 163 | T->A | 198 | Stop at 246 | 145 | C->G | 335 | G->A |
| 224 | Ins | 178 | A->C | 135 | Ins | 169 | G->T | 179 | Fr. |
| 251 | Stop at 344 | 186 | G->T | 187 | Stop at 246 | 184 | G->A | 341 | Stop at 344 |
| | | 208 | A->T | 264 | del | 364 | G->A | 103 | C->G |
| 261 | del | 255 | Fr. | 52 | C->T | 144 | del | 159 | Stop at 179 |
| 181 | G->A | 307 | G->A | 141 | G->C | 146 | Stop at 169 | 189 | Stop at 246 |
| 265 | C->T | 130 | T->G | 167 | A->G | 190 | C->A | 274 | Stop at 304 |
| 272 | T->C | 356 | G->T | 84 | C->T | 249 | A->C | 149 | Fr. |
| 136 | C->T | 43 | T->C | 122 | Stop at 169 | 214 | T->A | 183 | Stop at 183 |
| 281 | G->T | 159 | G->C | 140 | A->T | 204 | G->A | 227 | Stop at 245 |
| 316 | C->T | 280 | Ins | 153 | Ins | 242 | G->A/C->G | 292 | Stop at 343 |
| 130 | C->G | 327 | Fr. | 173 | Fr. | 208 | Stop at 241 | 178 | A->G |
| 234 | C->A | 87 | C->A | 186 | Fr. | 158 | Stop at 180 | 251 | Stop at 343 |
| 368 | Fr. | 156 | G->T | 152 | C->G | 217 | Stop at 221 | 252 | Stop at 263 |
| 301 | Fr. | 158 | C->G | 171 | A->G | 262 | Stop at 344 | 64 | Fr. |
| 148 | Fr. | 161 | G->T | 180 | G->T | 239 | Stop at 246 | 89 | Stop at 122 |
| 176 | G->T | 173 | Stop at 180 | 202 | G->A | 205 | Stop at 246 | 108 | Stop at 122 |
| 152 | C->T | 199 | G->T | 227 | T->G | 214 | T->C | 110 | Ins |
| 248 | C->G | 144 | Fr. | 298 | G->A | 297 | ins | 124 | Stop at 124 |
| 255 | T->G | 233 | Fr. | 303 | G->A | 268 | Fr. | 285 | del |
| 271 | Fr. | 275 | T->G | 261 | Ins | 256 | A->T | 342 | del |
| 274 | Fr. | 162 | T->G | 276 | C->G | 223 | C->A | 313 | A->T |
| 225 | G->A | 178 | Fr. | 305 | Fr. | 26 | Stop at 43 | 217 | T->A |
| 176 | T->A | 256 | Fr. | 117 | Stop at 122 | 186 | A->T | 167 | Stop at 169 |
| 135 | Fr. | 225 | Fr. | 155 | Stop at 177 | 214 | Stop at 246 | 278 | C->T/T->C |
| 135 | C->G | 148 | T->A | 277 | T->A | 245 | C->A | 290 | Stop at 304 |
| 151 | C->T | 187 | G->A | 298 | A->C | 287 | G->C | 173 | Stop at 173 |

TABLE 3-continued

| Codon | Event | Codon | Event | Codon | Event | Codon | Event | Codon | Event |
|---|---|---|---|---|---|---|---|---|---|
| 159 | C->T | 250 | C->A/C->A | 141 | C->T | 96 | C->T | 259 | C->T |
| 179 | A->G | 254 | T->G | 115 | T->C | 164 | Stop at 166 | 288 | T->A |
| 306 | C->T | 257 | T->C | 119 | G->A | 255 | Ins | 207 | T->A |
| 174 | G->A | 275 | T->C | 120 | Fr. | 275 | del | 197 | Stop at 208 |
| 208 | Fr. | 216 | G->T/G->T | 127 | T->A | 284 | ins | 214 | A->T |
| 126 | Fr. | 149 | T->C | 133 | Fr. | 161 | G->C | 127 | C->G |
| 173 | del | 240 | G->T | 144 | A->T | 246 | A->T/G->T | 337 | G->C |
| 192 | C->T | 65 | A->T | 187 | T->C | 199 | G->C | 102 | Stop at 122 |
| 209 | Fr. | 125 | C->T | 205 | T->A | 195 | Stop at 246 | 187 | Stop at 202 |
| 216 | T->G | 166 | C->T | 209 | A->G | 275 | Fr. | 100 | A->G |
| 258 | G->A | 242 | C->T | 237 | A->T | 283 | Stop at 305 | 140 | Stop at 143 |
| 282 | G->C | 263 | A->C | 337 | G->T | 233 | ins | 176 | Stop at 179 |
| 308 | Fr. | 139 | G->T | 342 | G->A | 127 | Stop at 169 | 235 | Ins |
| 332 | Fr. | 165 | A->T | 377 | C->A | 138 | G->A | 250 | Stop at 262 |
| 173 | T->G | 241 | T->G | 93 | C->T | 208 | A->T/C->T | 284 | Stop at 305 |
| 249 | Fr. | 255 | T->A | 202 | C->T | 106 | del | 132 | G->A |
| 275 | G->A | 265 | Fr. | 199 | Stop at 246 | 245 | G->C/G->T | 129 | C->T |
| 294 | G->T | 279 | Fr. | 252 | C->T | 212 | Stop at 246 | 210 | C->T |
| 316 | Fr. | 241 | C->T | 254 | C->T | 133 | G->A | 232 | C->T |
| 159 | C->A | 151 | C->G | 262 | G->A | 124 | T->C | 257 | C->T |
| 118 | Ins | 156 | Fr. | 263 | A->G | 51 | Stop at 122 | 164 | Stop at 169 |
| 277 | G->A | 170 | A->T | 274 | Stop at 344 | 170 | G->A | 249 | del |
| 244 | G->C | 204 | G->T | 293 | Stop at 344 | 150 | del | 187 | Fr. |
| 264 | Fr. | 249 | A->G | 156 | C->G | 85 | Stop at 143 | 210 | Fr. |
| 278 | C->T/C->T | 280 | G->T | 157 | Stop at 169 | 195 | T->A | 207 | T->C |
| 177 | C->T | 281 | A->C | 92 | C->T | 314 | Stop at 338 | 226 | G->C |
| 179 | C->T | 94 | T->A | 201 | T->A | 307 | Stop at 340 | 168 | C->G/C->G |
| 281 | C->T | 153 | C->A | 202 | Stop at 246 | 67 | Stop at 122 | 185 | A->G |
| 141 | G->A | 172 | T->C | 222 | C->T | 255 | Stop at 344 | 198 | Stop at 208 |
| 283 | Stop at 344 | 173 | T->A | 223 | Stop at 246 | 163 | del | 208 | G->C |
| 136 | Stop at 148 | 296 | C->G | 264 | Stop at 344 | 191 | Stop at 246 | 331 | A->C |
| 286 | G->A | 284 | A->G | 273 | C->A/G->A | 255 | Stop at 257 | 320 | Stop at 336 |
| 109 | C->A | 135 | G->T | 316 | C->A | 262 | Stop at 263 | 331 | A->C/G->A |
| 164 | A->G | 31 | G->A | 271 | Ins | 264 | C->A | 338 | T->A |
| 238 | G->C | 72 | Fr. | 129 | Fr. | 348 | G->T | 280 | Fr. |
| 110 | G->T | 91 | G->A | 192 | Ins | 232 | Stop at 246 | 290 | Fr. |
| 113 | T->G | 110 | Fr. | 307 | G->T | 170 | ins | 297 | Fr. |
| 162 | C->G | 154 | Fr. | 220 | T->A | 114 | T->A | 297 | C->G |
| 183 | C->G | 158 | Fr. | 285 | A->G | 343 | G->T | 136 | Stop at 164 |
| 287 | Stop at 344 | 167 | C->T | 226 | G->A | 26 | Stop at 36 | 149 | Stop at 180 |
| 152 | G->A | 178 | Stop at 180 | 137 | Ins | 137 | G->T | 221 | Stop at 246 |
| 138 | C->T | 195 | Stop at 208 | 259 | Ins | 145 | G->C | 228 | ins |
| 278 | C->G | 197 | G->A | 234 | Fr. | 146 | T->C | 243 | Stop at 340 |
| 236 | T->C | 199 | G->A | 135 | del | 286 | A->T | 292 | Stop at 304 |
| 237 | A->G | 227 | Ins | 102 | Stop at 116 | 296 | A->T | 328 | del |
| 289 | T->A | 248 | G->T/G->T | 324 | G->A/A->G | 164 | G->A | 338 | Stop at 346 |
| 237 | G->T | 265 | T->C/G->T | 27 | Fr. | 148 | T->G | 243 | A->C |
| 136 | Ins | 272 | T->A | 162 | del | 274 | del | 348 | T->A |
| 99 | Stop at 147 | 274 | T->G | 277 | Ins | 211 | Stop at 215 | 304 | C->T |
| 134 | Stop at 169 | 349 | Fr. | 135 | T->G | 239 | A->T | 228 | G->T |
| 242 | T->C | 203 | Fr. | 69 | C->G | 313 | ins | 370 | A->C |
| 193 | C->T | 205 | T->G | 242 | T->G | 327 | T->G | 149 | C->T/C->T |
| 188 | Fr. | 205 | A->C | 157 | G->A | 211 | C->A | 158 | C->T/G->A |
| 152 | Stop at 169 | 246 | A->T | 198 | G->C | 246 | Stop at 246 | 240 | G->A |
| 57 | Fr. | 282 | Stop at 305 | 157 | T->G | 163 | C->T | 258 | Stop at 263 |
| 281 | C->G | 133 | A->C | 279 | G->C | 252 | del | 317 | C->A |
| 260 | Stop at 263 | 162 | A->T | 134 | Ins | 129 | del | 262 | T->A |
| 132 | A->T | 174 | A->T | 239 | Stop at 263 | 215 | G->C | 263 | A->T |
| 249 | Stop at 263 | 253 | C->G | 168 | Stop at 169 | 253 | A->C | 163 | T->G |
| 167 | G->T | 131 | A->G | 134 | Fr. | 274 | Ins | 312 | Fr. |
| 17 | A->T | 137 | T->A | 253 | A->T | 154 | C->A | 301 | C->A |
| 24 | A->T | 141 | Fr. | 254 | A->T | 183 | C->T | 226 | G->A/G->A |
| 175 | C->T | 157 | T->A | 247 | A->G | 225 | T->A | 200 | A->C/A->C |
| 358 | G->A | 157 | Fr. | 235 | A->T | 149 | ins | 207 | G->C |
| 175 | Ins | 176 | Ins | 176 | Stop at 243 | 171 | Fr. | 226 | Stop at 227 |
| 115 | C->T | 240 | Fr. | 163 | Stop at 169 | 287 | A->T | 266 | |
| 103 | Fr. | 274 | T->C | 248 | Stop at 344 | 133 | G->T | 113 | del |
| 237 | Fr. | 46 | Fr. | 289 | Stop at 304 | 137 | C->A | 226 | Fr. |
| 250 | C->T | 112 | Fr. | 163 | Fr. | 148 | G->T | 94 | C->A |
| 365 | A->G | 295 | C->T | 207 | Fr. | 246 | A->C | 127 | Fr. |
| | | 193 | T->A | 251 | A->T | 251 | T->C | 133 | Stop at 145 |
| | | 221 | G->T | 112 | Stop at 120 | 273 | T->C | 153 | Stop at 180 |
| | | 227 | Fr. | 120 | Stop at 122 | 297 | C->A | 75 | C->T |
| | | 241 | C->A | 231 | C->T | 192 | G->A | 116 | Stop at 122 |
| | | 281 | G->A | 212 | Stop at 214 | 244 | C->G | 184 | del |
| | | 316 | Ins | 179 | A->C | 221 | Stop at 222 | 106 | Stop at 122 |
| | | 344 | Fr. | 174 | G->T | 243 | T->A | 69 | Stop at 147 |
| | | 145 | T->G | 232 | del | 308 | C->G | 298 | Stop at 344 |

TABLE 3-continued

| Codon | Event | Codon | Event | Codon | Event | Codon | Event | Codon | Event |
|---|---|---|---|---|---|---|---|---|---|
| 271 | G->A | 145 | T->C | 173 | Stop at 195 | 189 | C->A | 182 | ins |
| 320 | G->C | 194 | T->C | 273 | Stop at 344 | 239 |  | 133 | del |
| 349 | G->T | 162 | A->G | 143 | T->A | 142 | C->G | 163 | Stop at 168 |
| 126 | del | 315 | Ins | 161 | C->T | 295 | C->A | 174 | del |
| 36 | G->A | 203 | T->A | 72 | Stop at 120 | 156 | Stop at 168 | 330 | T->G |
| 76 | Fr. | 273 | Ins | 265 | del | 213 | Stop at 245 | 125 | C->G |
| 241 | C->G | 62 | G->T | 214 | Stop at 214 | 243 | Stop at 244 | 258 | Stop at 344 |
| 281 | G->C | 71 | Fr. | 107 | Stop at 147 | 289 | C->T | 330 | Stop at 335 |
| 244 | G->A | 128 | Fr. | 317 | Ins | 211 | del | 113 | T->C |
| 218 | T->G | 203 | T->C | 165 | C->A | 220 | Stop at 244 | 265 | T->G |
| 256 | Stop at 344 | 254 | C->G | 99 | Stop at 122 | 229 | T->G | 126 | T->C |
|  |  | 282 | Fr. | 36 | C->T | 253 | del | 214 | Stop at 218 |
| 280 | A->C/G->C | 258 | G->C | 245 | Ins | 302 | Stop at 303 | 284 | C->T |
| 258 | A->G | 217 | Fr. | 76 | C->T | 208 | A->G | 96 | ins |
| 270 | T->A | 139 | A->C | 160 | T->A | 212 | Stop at 244 | 62 | Stop at 121 |
| 176 | T->G | 215 | A->C | 165 | A->C | 129 | Stop at 145 | 285 | A->C |
| 171 | Stop at 231 | 243 | Ins | 269 | Fr. | 190 | del | 358 | G->T |
|  |  | 295 | Fr. | 245 | G->T/C->A | 216 | Stop at 221 | 122 | G->A |
| 251 | Stop at 263 | 285 | A->T | 208 | G->A | 275 | Stop at 304 | 69 | Stop at 122 |
|  |  | 170 | Stop at 179 | 236 | C->T | 150 | ins | 155 | C->T/C->G |
| 337 | C->T | 208 | Stop at 246 | 294 | G->A | 188 | C->G | 245 | G->A/C->G |
| 266 | G->C | 209 | Stop at 214 | 251 | Fr. | 220 | Ins | 181 | C->G |
| 203 | G->C | 240 | Stop at 263 | 215 | Ins | 292 | A->C | 185 | Ins |
| 241 | Stop at 252 | 141 | G->T | 154 | C->T | 305 | G->T | 52 | Stop at 56 |
|  |  | 151 | Fr. | 293 | G->C | 48 | A->T/C->T | 112 | Stop at 122 |
| 193 | A->T | 182 | Stop at 246 | 161 | C->G | 154 | C->G | 165 | Stop at 169 |
| 255 | A->G | 140 | A->G | 56 | G->A | 150 | Fr. | 323 | del |
| 194 | C->G | 142 | C->T | 139 | G->A | 329 | C->A | 67 | C->G |
| 342 | Stop at 342 | 169 | T->A | 222 | G->C | 80 | C->T | 148 | A->T |
|  |  | 170 | A->G | 302 | Stop at 344 | 243 | T->G | 230 | Stop at 246 |
| 55 | Ins | 271 | A->G | 144 | Stop at 169 | 104 | Stop at 148 | 95 | Stop at 148 |
| 257 | C->G | 331 | C->T | 166 | T->G | 117 | Stop at 148 | 276 | Stop at 286 |
| 282 | ins | 194 | Stop at 245 | 149 | T->A | 138 | C->A | 249 | Stop at 342 |
| 245 | G->C | 113 | T->G/T->G | 204 | del | 248 | C->T/G->C | 208 | del |
| 209 | ins | 165 | C->T | 127 | C->A | 167 | G->A | 163 | Stop at 163 |
| 239 | ins | 176 | Stop at 246 | 289 | T->C | 214 | C->G | 213 | A->G |
| 179 | T->G | 207 | T->G | 261 | A->G | 272 | Fr. | 282 | Stop at 304 |
| 314 | C->T | 297 | C->T | 269 | A->G | 186 | A->G | 295 | Stop at 344 |
| 155 | C->T | 141 | T->G | 128 | Stop at 169 | 147 | Ins | 160 | del |
| 249 | Stop at 344 | 181 | G->C | 159 | Stop at 169 | 261 | T->G | 233 | A->T |
|  |  | 229 | Fr. | 204 | Ins | 240 | T->G | 186 | T->C |
| 116 | C->G | 276 | Fr. | 242 | Stop at 242 | 288 | Fr. | 243 | T->C/G->A |
| 163 | A->G | 149 | Stop at 169 | 237 | del | 286 | A->G/A->T | 142 | C->A |
| 173 | G->C | 193 | C->G | 284 | Stop at 304 | 126 | Stop at 169 | 144 | G->T |
| 255 | C->T | 293 | Stop at 304 | 331 | G->T | 182 | Fr. | 231 | Fr. |
| 255 | C->G | 147 | Fr. | 130 | T->A | 298 | Fr. | 254 | Fr. |
| 218 | T->C | 286 | G->T | 39 | C->T | 220 | T->G | 266 | ins |
| 301 | Stop at 344 | 287 | Stop at 303 | 352 | G->C | 269 | G->A | 258 | A->C |
|  |  | 293 | G->A | 209 | Stop at 246 | 232 | Fr. | 239 | Stop at 261 |
| 271 | A->T | 295 | T->C | 90 | C->T | 131 | del | 262 | G->C/G->C |
| 286 | A->G | 215 | Fr. | 111 | G->A | 261 | Fr. | 296 | Stop at 334 |
| 294 | A->G | 333 | Fr. | 119 | C->T | 111 | T->A | 284 | del |
| 264 | C->T | 28 | A->C | 141 | T->C | 285 | Fr. | 150 | A->C |
| 235 | A->G | 67 | C->T | 202 | T->C | 266 | G->A/A->T | 225 | G->T |
| 249 | A->T | 288 | A->G | 326 | A->G | 162 | Stop at 169 | 247 | Fr. |
| 216 | G->A | 276 | del | 36 | G->T | 208 | Ins | 322 | C->T |
| 215 | G->A | 292 | Fr. | 68 | A->G | 250 | Ins | 85 | Stop at 117 |
| 272 | G->A | 189 | C->T | 117 | G->T | 130 | Stop at 169 | 86 | ins |
| 267 | Stop at 344 | 210 | A->G | 145 | G->T | 289 | Fr. | 189 | Fr. |
|  |  | 217 | T->C | 215 | G->A/T->A | 198 | Fr. | 315 | Fr. |
| 242 | G->A | 135 | Stop at 169 | 325 | G->A | 302 | Fr. | 169 | Stop at 180 |
| 195 | T->C | 165 | A->G | 112 | G->A | 137 | C->T | 245 | G->T/G->T |
| 172 | G->T | 234 | del | 308 | G->A | 191 | Ins | 175 | C->A/G->C/C->G |
| 239 | A->G | 218 | del | 63 | C->T | 186 | G->A |  |  |
| 262 | G->T | 100 | C->T | 104 | A->T | 237 | ins | 71 | C->T |
| 255 | T->C | 169 | G->A | 212 | T->C | 230 | A->G | 72 | Stop at 148 |
| 286 | A->C | 158 | Stop at 179 | 217 | G->A | 184 | A->G | 98 | T->A |
| 283 | G->A | 143 | Stop at 169 | 328 | T->C | 157 | ins | 287 | Stop at 304 |
| 190 | C->T | 200 | Ins | 45 | C->T | 95 | T->A/T->G | 162 | A->G/C->T |
| 154 | G->A | 185 | Stop at 246 | 299 | G->C | 314 | Fr. | 130 | T->C |
| 272 | Stop at 344 | 11 | G->A | 111 | T->G | 306 | A->G | 215 | Stop at 243 |
|  |  | 217 | G->C | 127 | T->C | 45 | C->A | 204 | Stop at 207 |
| 143 | G->A | 72 | Stop at 122 | 162 | Ins | 100 | C->T | 315 | Stop at 336 |
| 271 | A->C | 105 | G->T | 360 | G->T | 162 | Fr. | 33 | Stop at 43 |
| 133 | T->A | 221 | G->A | 257 | Ins | 319 | Fr. | 41 | Stop at 43 |
| 174 | Fr. | 253 | A->G | 341 | T->G | 113 | Fr. | 80 | Stop at 120 |
| 132 | A->G | 300 | Stop at 344 | 242 | Stop at 246 | 126 | C->A | 96 | Stop at 147 |
| 252 | Fr. | 250 | Stop at 342 | 262 | del | 196 | Stop at 246 | 207 | Stop at 212 |

TABLE 3-continued

| Codon | Event | Codon | Event | Codon | Event | Codon | Event | Codon | Event |
|---|---|---|---|---|---|---|---|---|---|
| 330 | T->A | 135 | T->A | 257 | T->G | 175 | G->A/C->G | 215 | Stop at 245 |
| 179 | C->A | 159 | C->T/C->T | 229 | T->C | 182 | T->G | 224 | Stop at 246 |
| 309 | C->G | 249 | G->A | 196 | G->A | 190 | C->G | 260 | del |
| 212 | ins | 198 | A->G | 200 | A->G | 141 | Stop at 148 | 276 | Stop at 339 |
| 175 | G->T | 238 | T->G | 278 | Stop at 344 | 166 | Stop at 180 | 290 | Stop at 339 |
| 153 | C->G | 243 | A->T | 144 | G->C | 345 | Stop at 369 | 300 | Stop at 343 |
| 145 | C->G/G->T | 259 | G->A | 158 | Stop at 169 | 192 | C->A | 51 | Stop at 121 |
| 277 | Fr. | 268 | A->G | 252 | Stop at 344 | 65 | Fr. | 301 | Stop at 303 |
| 275 | G->T | 287 | Fr. | 241 | Stop at 261 | 185 | G->T | 236 | A->C/C->G |
| 110 | C->T | 302 | G->A | 282 | C->T/G->A | 181 | C->A | 83 | C->T |
| 232 | T->A | 189 | G->C | 276 | G->T | 190 | Stop at 208 | 237 | T->C |
| 151 | C->A/C->T | 212 | Fr. | 196 | C->A | 155 | C->G | 156 | ins |
| 218 | G->T | 51 | G->T | 193 | T->C | 242 | G->T/C->T | 128 | C->G |
| 139 | A->G | 160 | G->C | 160 | A->C | 269 | A->T | 243 | T->G/G->C |
| 250 | C->G | 207 | Ins | 243 | A->G | 283 | Fr. | 133 | A->G |
| 280 | A->C | 147 | T->G | 206 | Stop at 246 | 189 | G->A | 125 | C->A |
| 127 | C->T | 177 | Fr. | 194 | T->A | 244 | G->A/G->C | 62 | A->G |
| 176 | G->C | 121 | Fr. | 212 | T->A | 138 | Stop at 148 | 54 | C->T |
| 274 | G->C | 147 | T->G | 169 | A->G | 188 | Stop at 208 | 84 | C->G |
| 246 | T->G | 160 | A->G | 183 | T->C | 246 | del | 202 | G->C/T->G |
| 229 | Stop at 238 | 230 | Fr. | 77 | C->G | 180 | G->C | 319 | A->C |
| | | 237 | A->C | 188 | Ins | 175 | del | 138 | C->G |
| 247 | A->C | 47 | Stop at 121 | 158 | G->T/C->T | 290 | Stop at 301 | 229 | T->A/G->A |
| 290 | G->A | 78 | Fr. | 194 | Stop at 207 | 271 | del | 101 | Stop at 122 |
| 219 | Stop at 246 | 81 | Stop at 122 | 253 | Ins | 156 | Stop at 180 | 278 | Stop at 304 |
| | | 108 | Stop at 146 | 360 | Stop at 369 | 69 | C->A | 339 | Fr. |
| 88 | Stop at 122 | 110 | G->C | 191 | C->G | 112 | C->A | 303 | G->T |
| | | 156 | C->T | 141 | T->A | 193 | C->A | 247 | Stop at 344 |
| 254 | T->C | 217 | del | 303 | A->T | 222 | Fr. | 299 | Ins |
| 283 | C->G | 242 | T->A | 49 | Ins | 228 | Stop at 245 | 293 | del |
| 299 | G->A | 245 | Stop at 340 | 62 | Stop at 141 | 145 | del | 247 | Stop at 343 |
| 346 | G->A | 251 | Ins | 103 | del | 148 | Stop at 167 | 5 | C->T |
| 116 | T->C | 91 | G->T | 105 | del | 140 | Stop at 168 | 123 | C->T |
| 150 | A->G | 136 | A->G | 121 | del | 171 | Stop at 180 | 126 | C->T |
| 95 | T->C | 146 | G->C | 124 | Ins | 304 | Fr. | 320 | G->A |
| 54 | T->A | 164 | A->T | 124 | Stop at 167 | 159 | ins | 356 | G->A |
| 256 | C->T | 194 | Fr. | 338 | Stop at 343 | 261 | G->A | 379 | G->A |
| 309 | C->A | 255 | A->T | 336 | G->T | 304 | A->G | 154 | Stop at 180 |
| 109 | T->C | 339 | Ins | 124 | C->G | 222 | G->T | 164 | G->C |
| 265 | T->C | 35 | G->T | 284 | A->T | 291 | G->C | 75 | C->G |
| 139 | Stop at 169 | 213 | G->T | 144 | G->A | 147 | T->A/T->A | 163 | Stop at 165 |
| | | 261 | Stop at 263 | 227 | C->T | 216 | G->C | 238 | Stop at 244 |
| 154 | G->T | 299 | T->C | 208 | G->T | 91 | Ins | 8 | C->T |
| 179 | A->T | 204 | A->T | 228 | G->A | 311 | A->C | 15 | A->C |
| 255 | del | 47 | Fr. | 196 | G->T | 334 | Stop at 344 | 61 | A->G |
| 342 | Stop at 344 | 178 | C->A | 195 | C->G | 211 | T->C | 72 | C->T |
| | | 257 | G->A | 272 | T->G | 197 | G->T | 102 | ins |
| 11 | G->C | 341 | C->T | 53 | G->C | 202 | C->A | 104 | G->T |
| 121 | Stop at 122 | 290 | C->T | 290 | C->G | 219 | C->A | 106 | A->G |
| | | 169 | T->C | 292 | A->T/A->T | 228 | G->C | 365 | C->T |
| 34 | ins | 233 | C->T | 245 | Stop at 246 | 163 | A->C | 10 | C->T |
| 53 | G->A | 198 | A->G | 188 | Stop at 246 | 271 | G->C/A->G | 21 | C->T |
| 144 | A->C | 200 | Fr. | 288 | Stop at 344 | 238 | Fr. | 361 | G->A |
| 280 | A->G | 228 | C->G | 176 | Fr. | 206 | T->A | 364 | C->T |
| 326 | G->T | 236 | C->A | 148 | Stop at 179 | 52 | del | 385 | T->C |
| 332 | Stop at 344 | 245 | G->T/C->T | 161 | Stop at 169 | 94 | Stop at 122 | 307 | A->G |
| | | 249 | Ins | 211 | Stop at 246 | 236 | Stop at 236 | 161 | G->T/C->T |
| 256 | Ins | 251 | T->A | 244 | Stop at 246 | 107 | C->A | 241 | Stop at 263 |
| 283 | C->T | 258 | Fr. | 247 | del | 106 | Fr. | 327 | Stop at 335 |
| 232 | T->C | 278 | Ins | 260 | Stop at 344 | 69 | Fr. | 157 | T->C |
| 184 | Fr. | 279 | Ins | 216 | T->C | 204 | Fr. | 132 | Stop at 169 |
| 273 | C->G | 296 | A->C | 231 | A->T | 305 | A->C/G->T | 221 | A->C |
| 133 | T->C | 255 | Stop at 343 | 208 | C->A | 269 | Stop at 344 | 184 | G->C |
| 272 | G->T | 290 | Stop at 344 | 301 | C->G | 230 | Stop at 238 | 157 | Stop at 179 |
| 293 | G->T | 137 | Stop at 145 | 208 | C->G | 227 | Stop at 228 | 289 | Stop at 305 |
| 267 | G->A | 155 | Fr. | 237 | G->C | 363 | G->A | 105 | G->C |
| 325 | G->T | 206 | Ins | 243 | G->C | 253 | Fr. | 215 | Stop at 221 |
| 71 | Ins | 242 | Ins | 159 | G->T | 250 | Stop at 344 | 179 | Stop at 180 |
| 120 | A->T | 300 | Fr. | 33 | Ins | 259 | C->A | 128 | Stop at 148 |
| 151 | Ins | 191 | T->C | 192 | del | 167 | del | 256 | Stop at 263 |
| 307 | Fr. | 191 | C->A | 312 | C->A | 173 | Stop at 246 | 131 | Stop at 169 |
| 108 | Fr. | 246 | T->A | 321 | Stop at 344 | 313 | Fr. | 143 | Stop at 167 |
| 257 | T->A | 258 | A->T | 283 | C->G/C->G | 346 | Ins | 158 | C->T/G->T |
| 257 | Stop at 344 | 143 | Ins | 285 | G->T | 293 | Ins | 207 | A->T |
| | | 159 | Fr. | 283 | C->A | 224 | A->T | 245 | Stop at 262 |
| 138 | G->T | 165 | Stop at 178 | 216 | del | 158 | Stop at 167 | 258 | Stop at 291 |
| 155 | C->A | 168 | Ins | 318 | C->T | 154 | Stop at 167 | 266 | Stop at 271 |
| 167 | C->A | 169 | del | 119 | G->C/C-> | 283 | Stop at 304 | 284 | Stop at 344 |

TABLE 3-continued

| Codon | Event | Codon | Event | Codon | Event | Codon | Event | Codon | Event |
|---|---|---|---|---|---|---|---|---|---|
| 174 | A->G | 195 | T->G | | G/C->G | 284 | C->A | 285 | ins |
| 181 | G->T | 191 | C->T | 344 | T->G | 176 | G->T/C->T | 290 | ins |
| 241 | T->A | 152 | Ins | 216 | Stop at 246 | 47 | C->T/C->T | 294 | Stop at 344 |
| 305 | A->T | 168 | A->C | 240 | G->C | 151 | C->T/C->T | 308 | Stop at 344 |
| 273 | C->A | 209 | G->C | 306 | Stop at 344 | 88 | C->T/C->T | 49 | Stop at 50 |
| 219 | C->T | 209 | G->A | 210 | A->T | 71 | C->A | 254 | Stop at 260 |
| 251 | C->G | 214 | T->G | 198 | A->T | 162 | T->C | 301 | Stop at 305 |
| 233 | C->G | 166 | Fr. | 273 | Fr. | 180 | A->G | 311 | Stop at 344 |
| 215 | Stop at 246 | 265 | Stop at 344 | 138 | del | 150 | Stop at 163 | 320 | Stop at 344 |
| 216 | Ins | 163 | C->G | 171 | Stop at 173 | 218 | Stop at 219 | 324 | Stop at 344 |
| 344 | T->C | 182 | T->A | 174 | Ins | 218 | ins | 244 | Stop at 263 |
| 213 | G->C | 211 | Ins | 209 | A->C | 228 | C->A | 265 | C->A |
| 82 | C->T | 236 | T->A | 208 | Stop at 215 | 248 | Fr. | 222 | Stop at 246 |
| 151 | del | 267 | C->T | 285 | Stop at 304 | 282 | G->A/G->T | 296 | C->A |
| 180 | G->A | 148 | G->A | 286 | G->C | 61 | A->T | 205 | ins |
| 337 | G->A | 133 | Stop at 169 | 130 | C->A | 75 | T->C | 77 | Fr. |
| 281 | A->T | 174 | Stop at 179 | 201 | Fr. | 76 | G->A | 86 | C->T |
| 133 | T->G | 239 | A->C | 330 | Stop at 344 | 295 | C->G | 112 | C->T |
| 236 | del | 244 | Fr. | 131 | Stop at 148 | 340 | G->A | 320 | ins |
| 306 | G->C | 271 | G->T | 236 | Stop at 239 | 144 | A->G | 125 | G->T |
| 227 | T->A | 278 | Fr. | 236 | Ins | 126 | T->G | 266 | Fr. |
| 138 | G->C | 171 | G->A | 238 | del | 234 | T->C/C->G | 135 | Stop at 148 |
| 178 | Stop at 246 | 229 | G->A | 313 | Stop at 334 | 165 | Fr. | 316 | Stop at 336 |
| 213 | C->T/A->G | 161 | C->G/C->A | 240 | Stop at 262 | 101 | A->T | 234 | T->A/C->A |
| 191 | Stop at 207 | 168 | C->A | 266 | del | 254 | Stop at 344 | 233 | C->T/A->C |
| 236 | A->G | 241 | T->C | 276 | Stop at 344 | 217 | G->A/G->A | 206 | T->A/G->T |
| 196 | G->C | 154 | Ins | 150 | Stop at 169 | 169 | Fr. | 226 | C->A |
| 156 | G->A | 177 | C->T/C->T | 222 | C->A | 167 | A->T | 302 | G->C |
| 339 | G->T | 202 | G->C | 218 | T->A | 148 | A->C | 260 | C->G |
| 166 | C->G | 250 | C->T/C->G | 228 | C->T | 155 | Stop at 180 | 220 | A->G/T->A |
| 184 | Stop at 246 | 261 | A->T | 141 | C->A | 195 | del | 233 | Stop at 246 |
| 279 | Stop at 344 | 303 | A->C | 221 | G->C | 248 | del | 325 | G->C |
| 140 | C->T | 182 | G->A | 226 | C->T | 275 | T->A | 185 | A->T |
| 282 | C->A | 177 | C->A | 215 | T->C | 230 | Stop at 239 | 186 | Stop at 208 |
| 162 | T->A | 271 | G->C | 85 | C->T | 303 | Stop at 344 | 184 | Stop at 185 |
| 251 | C->T | 292 | A->T | 89 | C->T | 279 | del | 187 | Stop at 208 |
| 241 | Stop at 246 | 300 | C->T | 101 | A->G | 153 | Fr. | 234 | C->T |
| 248 | G->A/G->A | 319 | A->T | 132 | A->T/A->G | 235 | A->C | 235 | Stop at 239 |
| 362 | Stop at 369 | 195 | Fr. | 160 | G->A | 82 | Stop at 145 | 141 | Stop at 169 |
| 81 | C->T | 269 | G->C | 196 | Fr. | 275 | ins | 264 | T->C |
| 224 | G->A/G->A | 172 | T->G | 46 | C->T | 82 | ins | 76 | A->T |
| 197 | T->G | 35 | G->C | 122 | G->T | 273 | T->G | 96 | T->C |
| 301 | C->T | 90 | Fr. | 108 | G->A | 276 | Stop at 305 | 308 | C->A |
| 157 | G->C | 135 | C->A | 103 | C->T | 254 | A->G | 96 | C->G |
| 282 | C->A | 131 | A->T | 281 | G->C/A->G/C->G | 225 | T->G | 206 | G->A |
| 276 | C->A | 155 | del | | | 246 | G->T | 241 | Ins |
| 250 | C->T/C->T | 228 | Stop at 239 | 105 | C->T | 111 | T->G |
| 279 | G->T | 292 | Stop at 305 | 273 | C->T/G->A | 93 | G->A | 238 | C->T |
| 219 | C->T/C->T | 387 | del | 140 | Stop at 148 | 254 | C->A | 347 | C->G |
| 152 | C->T/C->T | 231 | A->G | 270 | Stop at 337 | 294 | Ins | 154 | G->T/C->T |
| 157 | C->T | 268 | A->C | 190 | Stop at 195 | 139 | Fr. | 212 | T->G |
| 158 | C->T | 179 | T->C | 275 | Stop at 341 | 356 | G->C | 260 | C->A |
| 222 | C->T/C->T | 232 | A->T | 143 | Stop at 148 | 182 | G->C | 123 | Stop at 148 |
| 195 | C->T | 134 | T->G | 107 | C->G | 73 | Stop at 122 | 146 | T->G |
| 291 | G->T | 274 | G->A | 194 | Stop at 206 | 76 | C->G | 73 | T->A |
| 192 | A->T | 243 | Stop at 246 | 271 | Stop at 343 | 150 | Stop at 165 | 165 | G->T |
| 333 | G->A | 131 | A->C | 254 | del | 214 | Stop at 220 | 313 | G->A |
| 369 | del | | | 255 | Stop at 262 | | | 130 | ins |
| 203 | G->A | | | 322 | A->C | | | 133 | A->T |
| 232 | C->G | | | 323 | Stop at 340 | | | 289 | Ins |
| 188 | G->A | | | | | | | | |
| 224 | Fr. | | | | | | | | |
| 199 | A->G | | | | | | | | |
| 277 | T->C | | | | | | | | |
| 176 | T->C | | | | | | | | |
| 227 | T->C | | | | | | | | |
| 327 | T->C | | | | | | | | |
| 247 | C->T | | | | | | | | |
| 135 | C->T | | | | | | | | |
| 211 | C->T | | | | | | | | |
| 149 | C->T | | | | | | | | |

TABLE 3-continued

| Codon | Event |
|---|---|
| 142 | C->T/C->T |
| 138 | C->T/C->T |
| 178 | C->T |
| 241 | C->T/C->T |
| 130 | C->T |
| 127 | C->T/C->T |
| 135 | G->A |
| 211 | A->G |
| 286 | Fr. |
| 168 | Fr. |
| 175 | C->A |
| 381 | Fr. |
| 263 | Fr. |
| 292 | A->G |

The mutations observed most frequently in cancerous pathologies are presented in Table 4 below.

TABLE 4

| Position | Wild p53 | |
|---|---|---|
| | | SEQ ID NO. 1 |
| R273H | GAGGTGCGTGTTTGTGC | SEQ ID NO. 61 |
| R248Q | gcaTgaaccggaggcccaT | SEQ ID NO. 62 |
| R248W | gcaTgaaccggaggcccaT | SEQ ID NO. 63 |
| R249S | gcaTgaaccggaggcccaT | SEQ ID NO. 64 |
| G245S | CTGCATGGGCGGCATGAAC | SEQ ID NO. 65 |
| R282W | TGGGAGAGACCGGCGCACA | SEQ ID NO. 66 |
| R175H | TGTGAGGCACTGCCCCCAC | SEQ ID NO. 67 |
| C242S | TAACAGTTCCTGCATGGGCG | SEQ ID NO. 68 |
| Postion | Mutated p53 | |
| R273H | GAGGTGCATGTTTGTGC | SEQ ID NO. 69 |
| R248Q | gcaTgaacCAgaggcccaT | SEQ ID NO. 70 |
| R248W | GCATGAACTGGAGGCCAT | SEQ ID NO. 71 |
| R249S | gcaTgaaccggagTcccaT | SEQ ID NO. 72 |
| G245S | CTGCATGGGCAGAGCATGAAC | SEQ ID NO. 73 |
| R282W | TGGGAGAGACTGGCGCACA | SEQ ID NO. 74 |
| R175H | TGTGAGGCGCTGCCCCCAC | SEQ ID NO. 75 |
| C242S | TAACAGTTCCTCCATGGGCG | SEQ ID NO. 76 |

Thus, the oligonucleotides may be complementary to a target sequence belonging to the mutated gene of p53 carrying at least one of the mutations presented in Table 3, and most particularly at least one of the mutations of Table 4 above.

These oligonucleotides are capable of discriminating in an effective manner between the wild form and the mutated form of p3. The strategy is to block the expression of the mutated form to reactivate the wild form and induce in the cells a programmed death process for which the wild form is indispensable and/or to block any other process induced by the wild form of p53. Moreover, this discrimination capacity of the oligonucleotides of the invention makes it possible to not touch the cancerous cells and to spare the normal cells, which do not express this mutated form of p53.

We also provide for the treatment or prevention of diseases induced by an inactivation of protein p53 particularly the cancers resulting from the expression of mutated p53 and the cancers resulting from the expression of inhibitory genes of p53. We invention also provide for the prevention of the appearance of cancers in subjects expressing a mutated form of p53 as in the case of Li-Fraumeni cancer syndrome.

p53 can be inactivated via many distinct mechanisms. For example, in the majority of cervical cancers p53 is inactivated by E6, a protein coded by the human papilloma virus. E6 leads to the ubiquitinylation of p53 which leads to its degradation by the proteasome. In this case, the expression of p53 can be restored by inhibition of the expression of the protein E6. The aspects of this invention also relates to oligonucleotides presenting a sequence complementary to a specific polynucleotide sequence of the gene of the protein E6 of HPV. The sequence of the gene of the protein E6 of HPV is given in FIG. 6A as well as in the attached sequence listings as SEQ ID NO. 2.

As previously indicated, one strategy has as its goal to block using RNAi the expression of the androgen receptor in carcinomas. The sequence of the androgen receptor is given in the attached sequence listings as SEQ ID NO. 77. In order to treat carcinomas before they became resistant or to treat those that had become resistant by amplification of the receptor without mutation, siRNA homologous to a region for which no mutation had been described in the data banks of mutations of the androgen receptors (indicated as siRNA AR) were used. In order to treat specifically the prostate carcinomas that had become androgen resistant by mutation, a sequencing of the mRNA coding for the receptor was performed in the patient's cells in order to devise a specific sequence of the mutation, making it possible to treat the patient without consequence for the normal cells. An example is presented for the use of siRNA recognizing specifically the mutation of the androgen receptor present in the cell line LNCaP (siRNA LNCaP). Consequently, one aspect relates to oligonucleotides substantially complementary to a target sequence belonging to a DNA or messenger RNA molecule coding the mutated or nonmutated androgen receptor. For example, the androgen receptor bearing at least one of the mutations presented in Table 5. These oligonucleotides are specific to the androgen receptor and are useful for treating or preventing androgen-dependent diseases, such as, e.g., prostate cancer.

TABLE 5

| Acces-sion # | Phenotype | Pathogenicity Mutation type | Exon Domain | CpG prov-en | hot spot | Position Change Amino acid Base | Amino acid Base | Exon 1 tracts Poly Gln # | Poly Gly # | Androgen Binding Bmax | Kd | k | Ther-mo-labile | Comments | Sex of rearing | External Genitalia | Family history | Reference |
|---|---|---|---|---|---|---|---|---|---|---|---|---|---|---|---|---|---|---|
| 0001 | PAIS | Substitute | 1 Nterm | * | | 002 4 | Glu⇒Lys GAA⇒AAA | | | | | high | | 20-50% reduction in mutant protein | Male | Ambiguous | pos | Choong et al; J Clin Invest. 98: 1423-1431, 1996 |
| 0002 | CAIS | Insertion | 1 Nterm | | | 051 | Gly⇒0 GGC⇒+C | | | zero | | | | 1 nt insertion causing frameshift & stop in Codon 180 | Female | Normal | pos | Bruggenwirth et al; J Steroid Biochem Mol Biol 58: 569-675, 1996 |
| 0003 | Prostate cancer | Substitute | 1 Nterm | | | 054 523 | Leu⇒Ser TTG⇒TCG | | | | | | | Also Phe891Leu (TTT to CTT) mut. Somatic mutation | Male | Normal | | Tilley et al; Clinical Cancer Res. 2: 277-285, 1996 |
| 0004 | Laryngeal cancer | Deletion | 1 Nterm | | | 057 | ⇑ | | | | | | | 30 nt. deletion | Male | Normal | | Urushibata et al: 10th. Int. Cong. Endocrinol Abstr. P3-706, 1996 |
| 0005 | Prostate cancer | Substitute | 1 Nterm | | | 057 532 | Leu⇒Gln CTG⇒CAG | | | | | | | Somatic mutation | Male | Normal | | Tilley et al; Clinical Cancer Res. 2: 277-285, 1996 |
| 0411 | Mental Retard. | Deletion | 1 Nterm | | | 058 | ⇑ | 8 | | normal | normal | | | 3 affected siblings - normal CAG = 23 | Male | Normal | pos | Kooy et al; Am J Med Genet. 85: 389-393, 1999 |
| 0006 | Kennedy Syndrome | Insertion | 1 Nterm | | | 058-078 | ⇑ | >40 | | | | | | Expansion of polyglutamine repeat | Male | Normal | | LaSpada et al: Nature 352: 77, 1991 |
| 0007 | Prostate cancer | Deletion | 1 Nterm | | | 058-078 | ⇑ | 18 | | | | | | Contraction of poly Gln repeats (24 to 18) Somatic mutation | Male | Normal | | Schoenberg et al; Bioch. & Biophys Res Comm 198: 74-80 1994 |
| 0324 | Prostate cancer | Deletion | 1 Nterm | | | 058-078 | ⇑ | 22 | | | | | | Deletion of 1polyGln repeat (23-22) Somatic mutation | Male | Normal | | Watanabe et al; Jpn J Clin Oncol 27: 389-393, 1997 |
| 0325 | Prostate cancer | Insertion | 1 Nterm | | | 058-078 | ⇑ | 22 | | | | | | Insertion of 1polyGln repeat (21-22) in 2 diff patients. Som mut | Male | Normal | | Watanabe et al; Jpn J Clin Oncol 27: 389-393, 1997 |
| 0495 | Prostate cancer | Deletion | 1 Nterm | | | 058-078 | ⇑ | 18 | | | | | | Contraction of poly Gln repeats (20 to 18) Somatic mutation | Male | Normal | | Wallin et al; J Pathology 189: 559-653, 1999 |
| 0008 | CAIS | Substitute | 1 Nterm | * | | 060 540 | Gln⇒Stop CAG⇒TAG | | | low | | high | | Normal upregulation. | Female | Normal | neg | Zoppi et al; J Clin Inv 19: 1105, 1993 |
| 0409 | CAIS | Insertion or deletion | 1 Nterm | | | 060 542 | Gln⇒Gln CAG⇒CAAG | | | | | | | either 1nt. insert or 2nt. del. -frameshift & stop in codon 80 | Female | Normal | pos | Zhu et al; J Clin Endocrinol & metab 84: 1590-1594, 1999 |
| 0009 | Prostate cancer | Substitute | 1 Nterm | | | 064 550 | Gln⇒Arg CAG⇒CGG | | | | | | | Also Leu830Pro (CTT to CCT) mut. Somatic mutation | Male | Normal | | Tilley et al; Clinical Cancer Res. 2: 277-285, 1996 |
| 0416 | CAIS | Insertion | 1 Nterm | | | 085 617 | Gln⇒Gln CAG⇒CAAG | 25 | | zero | | | | 1nt. insertion causing frameshift and stop in codon 91 | Female | Normal | | Gottlieb et al; Hum Mutat. 14: 527-539, 1999 |
| 0529 | CWR22R | Substitute | 1 | | | 91 | Glu⇒Asp | 27 | 19 | | | | | AR indep. + Leu57Gln | Male | Normal | | Chelnski et al. The |

TABLE 5-continued

| Acces-sion # | Phenotype | Mutation type | Pathogenicity Exon Domain | Pathogenicity prov-en | CpG | hot spot | Amino acid Base | Position Change Amino Base | Exon 1 tracts Poly Gln # | Exon 1 tracts Poly Gly # | Androgen Binding Bmax | Androgen Binding Kd | Androgen Binding k | Ther-mo-labile | Comments | Sex of rearing | External Genitalia | Family history | Reference |
|---|---|---|---|---|---|---|---|---|---|---|---|---|---|---|---|---|---|---|---|
| | Prost. CA Cell line | | Nterm | | | | 635 | ⇒ | | | | | | | & His 874Tyr mut. + Duplication of exon 3 | | | | Prostate 47: 66-75, 2001 |
| 0417 | CAIS | Deletion | 1 Nterm | | | | 102 668 | Pro⇒Pro CCAC⇒CCG | 12 | 25 | zero | | | | 1 nt. deletion causing frameshift and stop in codon 172 | Female | Normal | neg | Gottlieb et al; Hum Mutat. 14: 527-539, 1999 |
| 0010 | Prostate cancer | Substitute | 1 Nterm | | | | 112 698 | Gln⇒His CAG⇒CAT | | | | | | | AlsoTrp798Stop (TGG to TGA) mut. Somatic mutation | Male | Normal | | Tilley et al; Clinical Cancer Res. 2: 277-285, 1996 |
| 0418 | CAIS | Substitute | 1 Nterm | | | | 113 699 | Gln⇒Stop CAA⇒TAA | 25 | 27 | | | | | | Female | Normal | | Gottlieb et al; Hum Mutat. 14: 527-539, 1999 |
| 0417 | CAIS | Deletion | 1 Nterm | | | | 125 738 | Pro⇒Pro CCAC⇒CCG | 23 | 24 | zero | | | | 1nt. deletion causing frameshift and stop at codon 172 | Female | Normal | | Gottlieb et al; Hum Mutat. 14: 527-539, 1999 |
| 0011 | CAIS | Deletion | 1 Nterm | | | | 127 743 | Arg⇒Arg AGAA⇒AGG | | | zero | | | | 1 nt deletion causing frameshift & stop in Codon 172 | Female | Normal | neg | Batch et al; Hum Mol Genet 1: 497, 1992 |
| 0436 | CAIS | Deletion | 1 Nterm | | | | 127 743 | Arg⇒Arg AGAA⇒AGG | | | | | | | 1 nt deletion causing frameshift & stop in Codon 172 | Female | Normal | | Ahmed et al; J Clin Endocrinol & Metab 85: 658-665, 2000 |
| 0012 | CAIS | Deletion | 1 Nterm | | | | 140 | ⇒ | | | | | | | Deletion of Codons 140-148 Stop in Codon 154 | Female | Normal | | Hiort et al; Am J Med Genet. 63: 218-222, 1996 |
| 0516 | CAIS | Substitute | 1 Nterm | | | | 153 819 | Glu⇒Stop GAG⇒TAG | | | low | normal | | | | Female | Normal | | Copelli et al; Asian J Androl 1: 73-77, 1999 |
| 0523 | CAIS | Substitute | 1 Nterm | | | | 153 819 | Glu⇒Stop GAG⇒TAG | | | | | | | | Female | Normal | | Gacobini et al. Hum Genet. 108; 176, 2001 |
| 0013 | CAIS | Substitute | 1 Nterm | | | | 172 876 | Leu⇒Stop TTA⇒TGA | | | | | | | | Female | Normal | | Hiort et al; Am J Med Genet. 63: 218-222, 1996 |
| 0316 | PAIS | Substitute | 1 Nterm | | | | 172 876 | Leu⇒Stop TTA⇒TGA | 26 | 24 | zero | | | | Somatic mosaic mut. causes partial virulization | Female | Ambiguous | | Holterhus et al; J Clin Endocrinol. 82: 3584-3589, 1997 |
| 0420 | CAIS | Substitute | 1 Nterm | | | | 172 876 | Leu⇒Stop TTA⇒TGA | | | | | | | | Female | Normal | neg | Gottlieb et al; Hum Mutat. 14: 527-539, 1999 |
| 0014 | Prostate cancer | Substitute | 1 Nterm | | | | 180 911 | Lys⇒Arg AAA⇒AGA | | | | | | | Somatic mutation | Male | Normal | | Tilley et al; Clinical Cancer Res. 2: 277-285, 1996 |
| 0319 | CAIS | Substitute | 1 Nterm | | | | 194 943 | Gln⇒Arg CAA⇒CGA | | | | | | | Also 1 nt deletion in Codon 597 causing stop | Female | Normal | | Komori et al; J Obstetrics & Gynocol. 23: 277-81, 1997 |
| 0551 | Prostate cancer | Substitute | 1 Nterm | | | | 198 955 | Glu⇒Gly GAA⇒GGA | | | | | | | Treated with bicalutamide - somatic mutation | Male | Normal | | Taplin et al; 37th meeting ASCO 20: Abstr, 1738 2001 |
| 0015 | CAIS | Insertion | 1 | | | | 202 | Glu⇒0 | | | zero | | | | 4 nt insertion causing | Female | Normal | neg | Batch et al; Hum Mol |

TABLE 5-continued

| Accession # | Phenotype | Mutation type | Pathogenicity Exon Domain | Pathogenicity proven | CpG hot spot | Position Change Amino acid Base | Position Change Amino acid Base | Position Change Amino acid Base | Exon 1 tracts Poly Gln # | Exon 1 tracts Poly Gly # | Androgen Binding Bmax | Androgen Binding Kd | Androgen Binding k | Thermolabile | Comments | Sex of rearing | External Genitalia | Family history | Reference |
|---|---|---|---|---|---|---|---|---|---|---|---|---|---|---|---|---|---|---|---|
| | | | Nterm | | | | | ⇒ | | | | | | | frameshift & stop in Codon 232 | | | | Genet 1: 497, 1992 |
| 0549 | Prostate cancer | Substitute | 1 Nterm | | | 202 968 | Glu⇒Glu | GAA⇒GAG | | | | | | | Treated with bicalutamide - silent mutation- somat. mut. | Male | Normal | | Taplin et al; 37th meeting ASCO 20: Abstr, 1738 2001 |
| 0395 | Normal | Substitute | 1 Nterm | | | 205 977 | Ser⇒Arg | AGC⇒AGG | | | | | | | Homosexual individual | Male | Normal | | Macke et al; Am J Human Genetics 53: 844-852, 1993 |
| 0437 | CAIS | Deletion | 1 Nterm | | | 208 985 | Arg⇒Lys | AAGA⇒AAG | | | zero | | | | Frameshift & stop in codon 232 ? | Female | Normal | | Ahmed et al; J Clin Endocrinol & Metab 85: 658-665, 2000 |
| 0376 | MAIS | Substitute | 1 Nterm | | | 210 992 | Arg⇒Arg | AGG⇒AGA | | | | | | | | Male | Normal | | Wang et al; Clinical Genetics 54: 185-192, 1998 |
| 0328 | Normal | Substitute | 1 Nterm | | | 211 995 | Glu⇒Glu | GAG⇒GAA | | | | | | | Silent mutation - polymorphism detected in 8% popul. | Male | Normal | | Batch et al; Hum Mol Genet 1: 497, 1992 |
| 0329 | Normal | Substitute | 1 Nterm | | | 211 995 | Glu⇒Glu | GAG⇒GAA | | | | | | | Silent mut. polymorph -detected in 14% of X chromosomes | Male | Normal | | Hiort et al; Eur J Pediatr 153: 317-321, 1994 |
| 0330 | Normal | Substitute | 1 Nterm | | | 211 995 | Glu⇒Glu | GAG⇒GAA | | | | | | | Silent mutation polymorphism | Male | Normal | | Lu et al; Clinical Genetics 49: 323-324. 1996 |
| 0377 | Normal | Substitute | 1 Nterm | | | 211 995 | Glu⇒Glu | GAG⇒GAA | | | | | | | Silent mutation polymorphism | Male | Normal | | Wang et al; Clinical Genetics 54: 185-192, 1998 |
| 0396 | Normal | Substitute | 1 Nterm | | | 211 995 | Glu⇒Glu | GAG⇒GAA | | | | | | | Silent mut. polymorph detected in 10% of X chromosomes | Male | Normal | | Macke et al; Am J Human Genetics 53: 844-852, 1993 |
| 0378 | MAIS | Substitute | 1 Nterm | | | 211 995 | Glu⇒Glu | GAG⇒GAA | | | | | | | Silent mutation polymorphism - 4 patients with infertility | Male | Normal | | Wang et al; Clinical Genetics 54: 185-192, 1998 |
| 0421 | CAIS | Substitute | 1 Nterm | | | 211 995 | Glu⇒Glu | GAG⇒GAA | 22 | | v low | | | | Silent mutation - negligible level of mRNA & hAR | Female | Normal | | Gottlieb et al; Hum Mutat. 14: 527-539, 1999 |
| 0422 | CAIS | Substitute | 1 Nterm | | | 211 995 | Glu⇒Glu | GAG⇒GAA | 21 | 23 | normal | normal | | | Silent mutation - | Female | Normal | neg | Gottlieb et al; Hum Mutat. 14: 527-539, 1999 |
| 0423 | PAIS | Substitute | 1 Nterm | | | 211 995 | Glu⇒Glu | GAG⇒GAA | 23 | 24 | v low | | | | Silent mutation - | Male | Ambiguous | | Gottlieb et al; Hum Mutat. 14: 527-539, 1999 |
| 0424 | PAIS | Substitute | 1 Nterm | | | 211 995 | Glu⇒Glu | GAG⇒GAA | 19 | 24 | normal | high | | | Silent mutation - | Male | Ambiguous | pos | Gottlieb et al; Hum Mutat. 14: 527-539, 1999 |
| 0425 | MAIS | Substitute | 1 | | | 211 | Glu⇒Glu | GAG⇒GAA | 20 | 16 | normal | high | | | Silent mutation - | Male | Normal | | Gottlieb et al; Hum |

TABLE 5-continued

| Acces-sion # | Phenotype | Mutation type | Pathogenicity Exon Domain | Pathogenicity prov-en | Pathogenicity CpG | Pathogenicity hot spot | Position Change Amino acid Base | Position Change Amino acid Base | Position Change Amino acid Base | Exon 1 tracts Poly Gln # | Exon 1 tracts Poly Gly # | Androgen Binding Bmax | Androgen Binding Kd | Androgen Binding k | Ther-mo-labile | Comments | Sex of rearing | External Genitalia | Family history | Reference |
|---|---|---|---|---|---|---|---|---|---|---|---|---|---|---|---|---|---|---|---|---|
| | | | Nterm | | | | 995 | | GAG⇒GAA | | | | | | | | | | | |
| 0379 | MAIS | Substitute | 1 Nterm | * | | | 214 1005 | Gly⇒Arg | GGG⇒AGG | 27 | | normal | normal | norm | | severe oligospermia-20% lower transactivation | Male | Normal | | Mutat. 14: 527-539, 1999 |
| 0380 | Normal | Substitute | 1 Nterm | | | | 214 1005 | Gly⇒Arg | GGG⇒AGG | | | | | | | | Male | Normal | | Wang et al; Clinical Genetics 54: 185-192, 1998 |
| 0016 | CAIS | Insertion | 1 Nterm | | | | 215 | Ala⇒Gly | GCT⇒GGCT | | | | | | | 1 nt Insertion causing frameshift & stop in Codon 232 | Female | Normal | neg | Wang et al; Clinical Genetics 54: 185-192, 1998 |
| 0548 | Prostate cancer | Substitute | 1 Nterm | | | | 222 1026 | Asn⇒Asp | AAT⇒GAT | | | | | | | Treated with flutamide also Thr877Ala - somatic mutation | Male | Normal | | Hiort et al; Hum Mol Genet 3: 1163-1166 1994 |
| 0531 | MAIS | Substitute | 1 Nterm | * | | | 233 1061 | Asn⇒Lys | AAC⇒ | | | normal | | | * | Azospermia - transactivation 46% of wt | Male | Normal | | Taplin et al; 37th meeting ASCO 20: Abstr, 1738 2001 |
| 0350 | CAIS | Substitute | 1 Nterm | * | | | 255 1126 | Leu⇒Pro | CTG⇒CCG | | | | | | * | Also Gly820Ala mut. Extra mutation causes greater thermolability | Female | Normal | | Giwercman et al. Clin Endocrinol 54: 827-834, 2001 |
| 0017 | CAIS | Substitute | 1 Nterm | | | | 266 1149 | Met⇒Thr | ATG⇒ACG | | | | | | | Also Leu574Pro (CTG to CCC) mut. Somatic mutation | Male | Normal | | Tanaka et al: Gynocol Endocrinol 12: 75-82, 1998 |
| 0018 | Prostate cancer | Substitute | 1 Nterm | | | | 269 1167 | Pro⇒Ser | CCA⇒TCA | | | | | | | Somatic mutation | Male | Normal | | Tilley et al; Clinical Cancer Res. 2: 277-285, 1996 |
| 0019 | CAIS | Deletion | 1 Nterm | | | | 272 1178 | Gly⇒Gly | GGAA⇒GGG | | | zero | | | | 1 nt deletion causing frameshift & stop in Codon 301 | Female | Normal | | Tilley et al; Clinical Cancer Res. 2: 277-285, 1996 |
| 0556 | Prostate cancer | Substitute | 1 Nterm | | | | 296 1250 | Ser⇒Arg | AGC⇒AGA | | | | | | | Poor differentiation of CaP. Germline mutation ? | Male | Normal | | Bruggenwirth et al; J Steroid Biochem Mol Biol 58: 569-575, 1996 |
| 0550 | Prostate cancer | Substitute | 1 Nterm | | | | 334 1359 | Ser⇒Pro | TCC⇒CCC | | | | | | | Treated with flutamide somatic mutation | Male | Normal | | Yu et al; Sheng Wu Hua Xue 32: 459-462, 2000 |
| 0398 | Prostate cancer | Substitute | 1 Nterm | | | | 340 1381 | Pro⇒Leu | CCG⇒CTG | | | | | | | Somatic mutation Stage 3 tumor | Male | Normal | | Taplin et al; 37th meeting ASCO 20: Abstr, 1738 2001 |
| 0020 | CAIS | Substitute | 1 Nterm | | | | 353 1419 | Glu⇒Stop | GAG⇒TAG | 21 | 23 | low | | | | low specific binding with MB only-mRNA <20% | Female | Normal | neg | Castagnaro et al; Verh. Dtsch. Ges. Path. 77: 119-123, 1993 |
| 0021 | CAIS | Substitute | 1 Nterm | | | | 371 1474 | Gly⇒Stop | GGA⇒TGA | | | | | | | Somatic instability of polyglycine tract | Female | Normal | pos | Gottlieb et al; Hum Mutat. 14: 527-539, 1999 |
| 0338 | MAIS | Substitute | 1 Nterm | * | | | 390 1530 | Pro⇒Ser | CCG⇒TCG | | | | | | | Oligospermia | Male | Normal | | Davies et al; Clinical Endocrinology 43: 69-77, 1995 |
| | | | | | | | | | | | | | | | | | | | | Hiort et al; J Clin Endocrinol & Metab 85: |

TABLE 5-continued

| Acces-sion # | Phenotype | Mutation type | Exon Domain | Pathogenicity proven | CpG hot spot | Amino acid Base | Position Change Amino acid Base | Exon 1 tracts Poly Gln # | Exon 1 tracts Poly Gly # | Androgen Binding Bmax | Androgen Binding Kd | Androgen Binding k | Ther-mo-labile | Comments | Sex of rearing | External Genitalia | Family history | Reference |
|---|---|---|---|---|---|---|---|---|---|---|---|---|---|---|---|---|---|---|
| 0504 | MAIS | Substitute | 1 Nterm | * | | 390 1530 | Pro⇒Ser CCG ⇒ TCG | | | | | | | Oligospermia | Male | Normal | | Hiort et al; J Clin Endocrinol & Metab 85: 2810-2815, 2000 |
| 0547 | Prostate cancer | Substitute | 1 Nterm | | | 390 1531 | Pro⇒Leu CCG ⇒ CTG | | | | | | | Treated with flutamide also Asn756Asp-somatic mutation | Male | Normal | | Taplin et al; 37th meeting ASCO 20: Abstr, 1738 2001 |
| 0022 | CAIS | Substitute | 1 Nterm | | | 390 1531 | Pro⇒Arg CCG ⇒ CGG | 20 | 24 | zero | | | | + substs. Gln211Glu GAGtoGAA&Gln443 Arg(CAGtoCGG) mRNA <20% | Female | Normal | pos | Gottlieb et al; Hum Mutat. 14: 527-539, 1999 |
| 0426 | CAIS | Substitute | 1 Nterm | | | 403 1569 | Gln⇒Stop CAG ⇒ TAG | 28 | 23 | zero | | | | | Female | Normal | | Gottlieb et al; Hum Mutat. 14: 527-539, 1999 |
| 0438 | CAIS | Deletion | 1 Nterm | | | 461 1735 | Gly⇒Gly GGΔC⇒GGG | | | zero | | | | 1 nt. deletion causing frameshift | Female | Normal | | Ahmed et al; J Clin Endocrinol & Metab 85: 658-665, 2000 |
| 0410 | CAIS | Deletion | 1 Nterm | | | 473 1779 | Glu⇒Gly GAAG⇒GGC | 24 | 22 | | | | | 2 nt. del causing frameshift & stop in cod 499-mRNA 50% | Female | Normal | | Thiele et al; J Clin Endocrinol & Metab 84: 1751-1753, 1999 |
| 0427 | CAIS | Deletion | 1 Nterm | | | 473 1779 | Glu⇒Gly GAAG⇒GGC | 26 | 26 | zero | | | | 2 nt. del causing frameshift & stop in cod 499-mRNA 50% | Female | Normal | | Gottlieb et al; Hum Mutat. 14: 527-539, 1999 |
| 0024 | CAIS | Substitute | 1 Nterm | | | 480 1802 | Tyr⇒Stop TAC ⇒ TAA | 15 | 15 | zero | | | | Normal 110 KD AR produced at 25% of normal level | Female | Normal | | Gottlieb et al; Hum Mutat. 14: 527-539, 1999 |
| 0546 | CAIS | Deletion | 1 Nterm | | | 487 1821 | Gln⇒Stop CAG ⇒ TAG | | | low | | | | 5 nt. deletion causing frameshift | Female | Normal | | Boehmer et al; J Clin Endocrinol & Metab 86: 4151-4160, 2001 |
| 0439 | CAIS | Deletion | 1 Nterm | | | 488 1824 | Gly⇒0 ⇒ | | | low | low | | | | Female | Normal | | Ahmed et al; J Clin Endocrinol & Metab 85: 658-665, 2000 |
| 0440 | CAIS | Substitute | 1 Nterm | | | 491 1833 | Gly⇒Ser GGC ⇒ AGC | | | | | | | | Female | Normal | | Ahmed et al; J Clin Endocrinol & Metab 85: 658-665, 2000 |
| 0025 | CAIS | Substitute | 1 Nterm | | | 502 1867 | Trp⇒Stop TGG ⇒ TAG | | | | | | | | Female | Normal | pos | Bruggenwirth et al; J Steroid Biochem Mol Biol 58: 569-575, 1996 |
| 0339 | MAIS | Substitute | 1 Nterm | * | | 511 1895 | Val⇒Val GTG ⇒ GTA | | | | | | | Oligospermia caused by silent mutation | Male | Normal | | Hiort et al; 80th US Endo Soc Meeting, Abstr P2-38, 1998 |
| 0026 | Prostate cancer | Substitute | 1 Nterm | | | 528 1945 | Asp⇒Gly GAT ⇒ GGT | | | | | | | Somatic mutation | Male | Normal | | Tilley et al; Chemical Cancer Res. 2: 277-285, 1996 |
| 0027 | CAIS | Substitute | 1 Nterm | | | 534 1964 | Tyr⇒Stop TAC ⇒ TAG | | | zero | | | | | Female | Normal | neg | McPhaul et al; FASEB J 5: 2910-15, 1991 |
| 0028 | CAIS and | Deletion | 1-8 | | | | ⇒ | | | zero | | | | Termini not yet | Female | Normal | neg | Trifiro et al; Mol Cell |

TABLE 5-continued

| Ac-ces-sion # | Phenotype | Mutation type | Pathogenicity | | | | Position Change | | Exon 1 tracts | | Androgen Binding | | | Comments | Sex of rearing | External Genitalia | Family history | Reference |
|---|---|---|---|---|---|---|---|---|---|---|---|---|---|---|---|---|---|---|
| | | | Exon Domain | prov-en | CpG | hot spot | Amino acid Base | Amino acid Base | Poly Gln # | Poly Gly # | Bmax | Kd | Ther-mo-labile | | | | | |
| | mental retardation | | | | | | | | | | | | | defined | | | | Endocrinol 75: 37-47, 1991 |
| 0029 | CAIS | Deletion | 1-8 | | | | ⇑ | | zero | | | | | | Female | Normal | pos | Quigley et al; J Clin Endocrinol Metab 74: 927, 1992 |
| 0030 | CAIS | Deletion | 1-8 | | | | ⇑ ⇑ | | zero | | | | | | Female | Normal | pos | Hiort et al; Am J Med Genet. 63: 218-22, 1996 |
| 0435 | CAIS | Deletion | 1-8 | | | | ⇑ ⇑ ⇑ | | zero | | | | | | Female | Normal | | Ahmed et al; J Clin Endocrinol & Metab 85: 658-665, 2000 |
| 0031 | CAIS | Deletion | 2 | | | | ⇑ ⇑ | | | | | | | | Female | Normal | | Quigley et al; J Cell Biochem Suppl 16C; Abstr L323, 1992 |
| 0441 | CAIS | Duplicat | 2 | | | | ⇑ | | | | | | | Dupli-cation of exon 2 | Female Normal | | | Ahmed et al; J Clin Endocrinol & Metab 85: 658-665, 2000 |
| 0032 | PAIS | Substitute | 2 | | | | 547 2003 | Leu⇒Phe TTG⇒TTT | | | low | high | | Also has Trp741Cys (TGG to TGT) mutation | Male | Ambiguous | pos | Karl et al; 76th US Endo Soc Meeting, Abstr 1735, 1994 |
| 0357 | Prostate cancer | Deletion | 2 | | | | 547 2003 | Leu⇒Leu TTAG⇒TTC | | | | | | Frameshift - somatic mutation | Male | Normal | | Takahashi et al; Cancer Research 55: 1621-1624, 1995 |
| 0033 | MAIS | Substitute | 2 | | | | 548 2004 | Pro⇒Ser CCC⇒TCC | | | | | | Distal hypospadia, variable penetrance in family members | Male | Near-normal male | pos | Sutherland et al; J of Urology 156: 828-831, 1996 |
| 0023 | CAIS | Duplicat | 2 | | | | 2011 | ⇑ ⇑ | | | | | | Duplication of 8 nt. # 2011-2018 frameshift & stop in Codon 563 | Female | Normal | | Lumbroso et al; 10th Int Cong of Endocrinol, Abstr P1-182, 1996 |
| 0358 | Prostate cancer | Deletion | 2 | | | | 554 2023 | Pro⇒Pro CCAA⇒CCC | | | | | | Frameshift - somatic mutation | Male | Normal | | Takahashi et al; Cancer Research 55: 1621-1624, 1995 |
| 0359 | Prostate cancer | Deletion | 2 | | | | 554 2023 | Pro⇒Pro CCAA⇒CCC | | | | | | Frameshift - somatic mutation | Male | Normal | | Takahashi et al; Cancer Research 55: 1621-1624, 1995 |
| 0034 | CAIS | Substitute | 2 DBD | * | | | 559 2038 | Cys⇒Tyr TGC⇒TAC | | | normal | normal | | | Female | Normal | neg | Zoppi et al; Mol Endocrinol 6: 409, 1992 |
| 0035 | PAIS | Substitute | 2 DBD | | | | 568 2064 | Gly⇒Trp GGG⇒TGG | | | normal | normal | | | Female | Normal | | Lobaccaro et al; Clin Endocrinol, 40: 297, 1994 |
| 0036 | PAIS | Substitute | 2 DBD | | | | 568 2065 | Gly⇒Val GGG⇒GTG | | | normal | normal | | | Male | Ambiguous | | Allera et al; J Clin Endocrinol & Metab 80: 2697-2699, 1995 |
| 0037 | PAIS | Substitute | 2 | | | | 568 | Gly⇒Val | | | normal | normal | | Severe hypospadia | Male | | | Chang et al; 73rd US |

TABLE 5-continued

| Accession # | Phenotype | Mutation type | Exon Domain | Pathogenicity proven | CpG hot spot | Position Change Amino acid Base | Amino acid Base | Position Change Amino acid Base | Exon 1 tracts Poly Gln # | Exon 1 tracts Poly Gly # | Androgen Binding Bmax | Androgen Binding Kd | Androgen Binding k | Thermolabile | Comments | Sex of rearing | External Genitalia | Family history | Reference |
|---|---|---|---|---|---|---|---|---|---|---|---|---|---|---|---|---|---|---|---|
| 0545 | PAIS | Substitute | 2 DBD | | | 2065-6 | | GGG⇒GTT | 21 | | | | | | | Male | Ambiguous | | Endo Soc Meeting, Abstr 28, 1991 |
| 0558 | PAIS | Substitute | 2 DBD | | | 571 2073 | Tyr⇒His | TAT⇒CAT | | | | | | | | Male | Ambiguous | | Boehmer et al; J Clin Endocrinol & Metab 86: 4151-4160, 2001 |
| 0332 | CAIS | Substitute | 2 DBD | * | | 571 2073 | Tyr⇒His | TAT⇒CAT | | | | | | | DHT therapy effective | Female | Normal | | Foresta et al; Am J Med Genet 107: 259-260, 2002 |
| 0038 | CAIS | Substitute | 2 DBD | | | 571 2074 | Tyr⇒Cys | TAT⇒TGT | | | normal | | | | Defective DNA binding & transactivation | Female | Normal | neg | Komori et al; Arch Gynecol & Obstetrics 261: 95-100, 1998 |
| 0489 | Prostate Cancer | Substitute | 2 DBD | | | 573 2080 | Ala⇒Asp | GCT⇒GAT | | | | | | | Somatic Mutation | Male | Normal | | Bruggenwirth et al; J Steroid Biochem Mol Biol 58: 569-575, 1996 |
| 0039 | CAIS | Substitute | 2 DBD | * | | 575 2085 | Thr⇒Ala | ACA⇒GCA | | | normal | normal | | | | Female | Normal | pos | Marcelli et al; Cancer Research 60: 944-949, 2000 |
| 0040 | CAIS | Substitute | 2 DBD | | | 576 2088 | Cys⇒Arg | TGT⇒CGT | | | normal | normal | | | | Female | Normal | | Zoppi et al; Mol Endocrinol 6: 409, 1992 |
| 0407 | CAIS | Substitute | 2 DBD | | | 576 2089 | Cys⇒Phe | TGT⇒TTT | | | | | | | Lack of DNA binding - 17 members of same family | Female | Normal | | Chang et al; 73rd US Endo Soc Meeting, Abstr 28, 1991 |
| 0554 | PAIS | Substitute | 2 DBD | * | | 577 2091 | Gly⇒Arg | GGA⇒AGA | | | normal | normal | high | | Alters affinity & selectivity of AR-ARE interactions | Female | Normal | | Hooper et al; 81st US Endo Soc Meeting, Abstr P2-145, 1999 |
| 0509 | PAIS | Substitute | 2 DBD | * | | 578 2095 | Ser⇒Thr | AGC⇒ACC | | | normal | | | | partial tranactivation in COS cells | Male | Ambiguous | | Nguyen et al; Mol Endocrinol 15: 1790-1802, 2001 |
| 0041 | CAIS | Substitute | 2 DBD | | | 579 2098 | Cys⇒Tyr | TGC⇒TAC | | | normal | normal | | | | Female | Normal | | Giwercman et al; Hormone Research 53: 83-88, 2000 |
| 0042 | CAIS | Substitute | 2 DBD | * | | 579 2098 | Cys⇒Phe | TGC⇒TTC | | | | | | | Reduced transcription & DNA binding | Female | Normal | pos | Sultan et al, J Steroid Biochem & Mol Biol: 46 519, 1993 |
| 0043 | CAIS | Deletion | 2 DBD | | | 579 2099 | Cys⇒Cys | TGΔC⇒TGA | | | zero | | | | Single nt. deletion causing frameshift & stop in Codon 619 | Female | Normal | | Imasaki et al; Mol & Cell Endocrinol 120: 15-24, 1996 |
| 0487 | Prostate Cancer | Substitute | 2 DBD | | | 580 2101 | Lys⇒Arg | AAG⇒AGG | | | | | | | Somatic mutation | Male | Normal | | Imai et al, Annals of Clin Biochem, 32: 482-486, 1995 |
| 0044 | CAIS | Substitute | 2 DBD | * | | 581 2103 | Val⇒Phe | GTC⇒TTC | | | normal | normal | | | | Female | Normal | | Marcelli et al: Cancer Research 60: 944-949, 2000 |
| 0045 | CAIS | Deletion | 2 DBD | * | | 582 | Phe⇒0 | | 22 | 23 | low | normal | | | 3 nt. del - Phe 582 del | Female | Normal | neg | Lumbroso et al; Fertil Steril, 60: 814, 1993; Beitel et al; Hum Mol |

TABLE 5-continued

| Acces-sion # | Phenotype | Mutation type | Pathogenicity Exon Domain | Pathogenicity prov-en | CpG | hot spot | Position Change Amino acid Base | Position Change Amino acid Base | Exon 1 tracts Poly Gln # | Exon 1 tracts Poly Gly # | Androgen Binding Bmax | Androgen Binding Kd | Androgen Binding k | Ther-mo-labile | Comments | Sex of rearing | External Genitalia | Family history | Reference |
|---|---|---|---|---|---|---|---|---|---|---|---|---|---|---|---|---|---|---|---|
| 0442 | CAIS | Deletion | 2 DBD | | | | 2104-6 | GATCTT⇒GTC | | | | | | | 2nt. from 581, Int. 582. 581 still Val 3 nt. del - of Phe | Female | Normal | | Genet, 3: 21, 1994 |
| 0047 | PAIS | Substitute | 2 DBD | | | | 582 2106-8 | Phe⇒0 TTC⇒ | | | | | | | | Female | Ambiguous | | Ahmed et al; J Clin Endocrinol & Metab 85: 658-665, 2000 |
| 0046 | PAIS | Substitute | 2 DBD | * | | | 582 2107 | Phe⇒Ser TTC⇒TCC | | | zero | | | | | Female | Ambiguous | | Hiort et al; Hum Mol Genet 3: 1163-1166 1994 |
| 0048 | CAIS | Substitute | 2 DBD | | | | 582 2107 | Phe⇒Tyr TTC⇒TAC | | | normal | normal | | | Reduced transcription & DNA binding | Female | Normal | pos | Imasaki et al; Mol & Cell Endocrinol 120: 15-24, 1996 |
| 0049 | CAIS | Deletion | 2 DBD | | | | 585 2116 | Arg⇒Lys AGA⇒AAA ⇑ ⇑ | | | | | | | | Female | Normal | | Sultan et al; J Steroid Biochem & Mol Biol: 46 519, 1993 |
| 0050 | CAIS | Deletion | 2-8 | | * | | | ⇑ ⇑ ⇑ | | | zero | | | | Similar 2-8 deletion in 2 different families | Female | Normal | | Jakubiczka et al; Human Mutation 9: 57-61, 1997 |
| 0051 | CAIS | Deletion | 3 DBD | | | | | ⇑ ⇑ ⇑ | | | high | normal | | | Produces internally deleted protein | Female | Normal | | Quigley et al; Mol Endocrinol 6: 1103, 1992 |
| 0443 | CAIS | Deletion | 3 DBD | | | | | ⇑ ⇑ ⇑ | | | zero | | | | | Female | Normal | pos | Hiort et al: Am J Med Genet. 63: 218-22, 1996 |
| 0444 | CAIS | Deletion | 3 DBD | | | | | ⇑ ⇑ | | | | | | | | Female | Normal | | Ahmed et al; J Clin Endocrinol & Metab 85: 658-665, 2000 |
| 0488 | Prostate Cancer | Substitute | 3 DBD | | | | 586 2119 | Ala⇒Val GCC⇒GTC | | | | | | | Somatic mutation | Male | Normal | | Marcelli et al; Cancer Research 60: 944-949, 2000 |
| 0490 | Prostate Cancer | Substitute | 3 DBD | | | | 587 2121 | Ala⇒Ser GCT⇒TCT | | | | | | | Somatic mutation | Male | Normal | | Marcelli et al; Cancer Research 60: 944-949, 2000 |
| 0052 | CAIS | Substitute | 3 DBD | * | | | 590 2130 | Lys⇒Stop AAA⇒TAA | | | zero | | | | | Female | Normal | | Marcelli et al: Mol Endocrinol 4: 1105, 1990 |
| 0053 | PAIS | Substitute | 3 DBD | * | | * | 596 2148 | Ala⇒Thr GCC⇒ACC | | | normal | normal | | | Found in 2 unrelated fam. Abolishes dimerization | Male | Ambiguous | pos | Gast et al; Mol & Cell Endocrinol 111: 93-98, 1995 |
| 0434 | PAIS | Substitute | 3 DBD | | | * | 596 2148 | Ala⇒Thr GCC⇒ACC | | | normal | normal | | | Somatic mosaicism | Male | Ambiguous | | Holterhus et al; Pediatric Res 46: 684-690, 1999 |
| 0510 | PAIS | Substitute | 3 DBD | * | | * | 596 2148 | Ala⇒Thr GCC⇒ACC | | | normal | | | | partial transactivation in COS cells | Male | Ambiguous | | Giwercman et al; Hormone Research 53: 83-88, 2000 |
| 0054 | PAIS | Substitute | 3 DBD | * | | | 597 2151 | Ser⇒Gly AGC⇒GGC | | | normal | normal | | | High dissoc. rate. Also has Arg617Pro | Female | Ambiguous | | Zoppi et al; Mol Endocrinol 6: 409, 1992 |

TABLE 5-continued

| Acces-sion # | Phenotype | Mutation type | Pathogenicity Exon Domain | prov-en | CpG hot spot | Amino acid Base | Position Change Amino acid Base | Exon 1 tracts Poly Gln # | Poly Gly # | Androgen Binding Bmax | Kd | k | Ther-mo-labile | Comments | Sex of rearing | External Genitalia | Family history | Reference |
|---|---|---|---|---|---|---|---|---|---|---|---|---|---|---|---|---|---|---|
| 0390 | PAIS | Substitute | 3 DBD | | | 597 2152 | Ser⇒Thr AGC⇒ACC | | | | | | | (CGG to CCG) mut. Servere hypospadia and cryptorchidism | Male | Ambiguous | | Nordenskjold et al Urological Res. 27: 49-55, 1999 |
| 0055 | CAIS | Substitute | 3 DBD | | | 601 2164 | Cys⇒Phe TGC⇒TTC | | | | | | | | Female | Normal | pos | Baldazzi et al; Hum Mol Genet 3: 1169-70 1994 |
| 0056 | PAIS | Substitute | 3 DBD | | | 604 2172 | Asp⇒Tyr GAT⇒TAT | | | | | | | | Male | Ambiguous | | Hiort et al: Hum Mol Genet 3: 1163-1166 1994 |
| 0057 | CAIS | Substitute | 3 DBD | | * | 607 2181 | Arg⇒Stop CGA⇒TGA | | | zero | | | | | Female | Normal | | Brown et al; Eur J Pediatr (Suppl 2) 152; S62, 1993 |
| 0511 | CAIS | Substitute | 3 DBD | | * | 607 2181 | Arg⇒Stop CGA⇒TGA | | | zero | | | | | Female | Normal | | Giwercman et al; Hormone Research 53: 83-88, 2000 |
| 0058 | PAIS and breast cancer | Substitute | 3 DBD | | * | 607 2182 | Arg⇒Gln CGA⇒CAA | | | | | | | | Male | Ambiguous | pos | Wooster et al; Nat Genet 2: 132, 1992 |
| 0059 | PAIS | Substitute | 3 DBD | * | * | 607 2182 | Arg⇒Gln CGA⇒CAA | | | normal | normal | | | | Male | Ambiguous | pos | Weidemann et al; Clin Endocrinology 45: 733-739, 1996 |
| 0060 | PAIS | Substitute | 3 DBD | | * | 607 2182 | Arg⇒Gln CGA⇒CAA | | | | | | | | Female | Ambiguous | | Hiort et al; Am J Med Genet. 63: 218-222, 1996 |
| 0347 | PAIS | Substitute | 3 DBD | | * | 607 2182 | Arg⇒Gln CGA⇒CAA | | | | | | | Patient successfully treated with testosterone enanthate | Male | Ambiguous | | Weidemann et al; J Clin Endocrinol & Metab 83: 1173-1176, 1998 |
| 0393 | PAIS | Substitute | 3 DBD | | * | 607 2182 | Arg⇒Gln CGA⇒CAA | | | | | | | Germ cell tumour - in undescended testis | Female | Normal | | Chen et al; Human Reproduction 14: 664-670, 1999 |
| 0412 | CAIS | Deletion | 3 DBD | | | 608 2184 | ⇒ ⇒ | | | | | | | Mullerian ducts pres. 5 nt. del frameshift & stop in codon 619 | Female | Normal | | Chen et al; Fertility & Sterility 72: 170-173, 1999 |
| 0061 | PAIS | Substitute | 3 DBD | | | 608 2185 | Arg⇒Lys AGG⇒AAG | | | normal | normal | | | | Male | Ambiguous | | Saunders et al: Clin Endocrinol 37: 214, 1992 |
| 0062 | PAIS and breast cancer | Substitute | 3 DBD | | | 608 2185 | Arg⇒Lys AGG⇒AAG | | | normal | normal | | | | Male | Ambiguous | | Lobaccaro et al; Hum Mol Genet, 2: 1799, 1993 |
| 0322 | PAIS | Substitute | 3 DBD | | | 608 2185 | Arg⇒Lys AGG⇒AAG | | | normal | normal | | | Defective nuclear localization | Male | Ambiguous | | Tincello et al; Clinical Endocrinology 46: 497-506, 1997 |
| 0352 | PAIS | Substitute | 3 DBD | | | 608 2185 | Arg⇒Lys AGG⇒AAG | | | | | | | | Male | Ambiguous | pos | Hiort et al; J Pediatrics 132: 939-943, 1998 |
| 0481 | PAIS | Substitute | 3 | | | 608 | Arg⇒Lys | | | normal | high | | | | | | | Ahmed et al; J Clin |

TABLE 5-continued

| Ac-ces-sion # | Phenotype | Mutation type | Pathogenicity Exon Domain | Pathogenicity prov-en | Pathogenicity CpG | Pathogenicity hot spot | Amino acid Base | Position Change Amino acid Base | Exon 1 tracts Poly Gln # | Exon 1 tracts Poly Gly # | Androgen Binding Bmax | Androgen Binding Kd | Androgen Binding k | Ther-mo-labile | Comments | Sex of rearing | External Genitalia | Family history | Reference |
|---|---|---|---|---|---|---|---|---|---|---|---|---|---|---|---|---|---|---|---|
| 0063 | PAIS | Substitute | 3 DBD | * | | | 2185 | AGG⇒AAG | | | | | | | | Male | Ambiguous | | Endocrinol & Metab 85: 658-665, 2000 |
| 0496 | CAIS | Substitute | 3 DBD | | | | 610 2190 | Asn⇒Thr AAT⇒ACT | | | normal | low | | * | | Female | Normal | | Weidemann et al; Clin Endocrinology 45: 733-739, 1996 |
| 0064 | CAIS | Substitute | 3 DBD | * | | | 611 2193 | Cys⇒Tyr TGT⇒TAT | | | | | | | | Female | Normal | | Mockel et al; Geburtshi. und Frauen. 60: 232-234, 2000 |
| 0512 | CAIS | Deletion | 3 DBD | * | | | 615 2204-6 | Arg⇒0 TGATCG⇒TGT | 27 | 23 | normal | normal | | | 3 nt. del - Arg615 del, 1 nt. from 614, 2nt. 615. 614 still Cys no transactivation in COS cells | Female | Normal | pos | Beitel et al; Hum Mol Genet, 3: 21, 1994 |
| 0065 | CAIS | Substitute | 3 DBD | * | * | | 615 2205 | Arg⇒Gly CGT⇒GGT | | | | | | | | Female | Normal | | Giwercman et al; Hormone Research 53: 83-88, 2000 |
| 0066 | CAIS | Substitute | 3 DBD | * | * | | 615 2206 | Arg⇒His CGT⇒CAT | 25 | 23 | low | high | | | | Female | Normal | pos | Beitel et al; Hum Mol Genet, 3: 21, 1994 |
| 0067 | CAIS | Substitute | 3 DBD | * | * | | 615 2206 | Arg⇒His CGT⇒CAT | | | normal | normal | | | | Female | Normal | pos | Mowszowicz et al; Mol Endocrinol 7: 861-869, 1993 |
| 0068 | CAIS | Substitute | 3 DBD | * | * | | 615 2206 | Arg⇒His CGT⇒CAT | | | | | | | | Female | Normal | | Brown et al; Eur J Pediatr 152 (Suppl 2): S62, 1993 |
| 0348 | CAIS | Substitute | 3 DBD | | * | | 615 2206 | Arg⇒His CGT⇒CAT | | | | | | | | Female | Normal | | Ris-Stalpers et al; Pediatr Res 36: 227, 1994 |
| 0353 | CAIS | Substitute | 3 DBD | | * | | 615 2206 | Arg⇒His CGT⇒CAT | | | | | | | | Female | Normal | | Cabral et al; Brazilian J Mol & Biol Res. 31: 775-778, 1998 |
| 0354 | CAIS | Substitute | 3 DBD | | * | | 615 2206 | Arg⇒His CGT⇒CAT | | | | | | | | Female | Normal | | Hiort et al; J Pediatrics 132: 939-943, 1998 |
| 0069 | PAIS | Substitute | 3 DBD | | * | | 615 2206 | Arg⇒His CGT⇒CAT | | | | | | | | Male | Ambiguous | | Hiort et al; J Pediatrics 132: 939-943, 1998 |
| 0070 | PAIS | Substitute | 3 DBD | | | | 615 2206 | Arg⇒Pro CGT⇒CCT | | | | | | | | Male | Ambiguous | | Hiort et al; Am J Med Genet. 63: 218-222, 1996 |
| 0445 | CAIS | Substitute | 3 DBD | | | | 615 2206 | Arg⇒Pro CGT⇒CCT | | | normal | high | | | | Female | Normal | | Ahmed et al; J Clin Endocrinol & Metab 85: 658-665, 2000 |
| 0071 | PAIS | Substitute | 3 DBD | * | | | 616 2209 | Leu⇒Arg CTT⇒CGT | | | normal | normal | | | | Female | Ambiguous | pos | De Bellis et al; J Clin Endocrinol Metab, 78: 513, 1994 |
| 0072 | CAIS | Substitute | 3 DBD | | | | 616 2209 | Leu⇒Pro CTT⇒CCT | | | | | | | | Female | Normal | | Mebarki et al; 75th US Endo Soc Meeting, |

TABLE 5-continued

| Accession # | Phenotype | Mutation type | Exon Domain | Pathogenicity proven | CpG hot spot | Amino acid Base | Position Change Amino acid Base | Exon 1 tracts Poly Gln # | Poly Gly # | Androgen Binding Bmax | Kd | k | Ther-mo-labile | Comments | Sex of rearing | External Genitalia | Family history | Reference |
|---|---|---|---|---|---|---|---|---|---|---|---|---|---|---|---|---|---|---|
| 0073 | CAIS | Substitute | 3 DBD | * | | 616 2209 | Leu⇒Pro CTT⇒CCT | | | normal | normal | | | | Female | Normal | | Abstr 602, 1993 Lobaccaro et al; Mol Cell Endorinol, 5: 137-147, 1996 |
| 0074 | PAIS | Substitute | 3 DBD | * | | 617 2212 | Arg⇒Pro CGG⇒CCG | | | normal | normal | | | | Female | Ambiguous | pos | Marcelli et al; J Clin Invest. 87: 1123, 1991 |
| 0075 | PAIS | Substitute | 3 DBD | * | | 617 2212 | Arg⇒Pro CGG⇒CCG | | | normal | normal | high | | Mutation also at 597 | Female | Normal | | Zoppi et al; Mol Endocrinol 6: 409, 1992 |
| 0431 | Prostate cancer | Substitute | 3 DBD | * | | 619 2218 | Cys⇒Tyr TGT⇒TAT | | | low | high | | | Inactive transcription Does not bind DNA somatic mutation | Male | Normal | | Nazereth et al; Mol Endocrinol 13: 2065-2075, 1999 |
| 0491 | Prostate cancer | Substitute | 3 DBD | | | 619 2218 | Cys⇒Tyr TGT⇒TAT | | | | | | | Somatic mutation | Male | Normal | | Marcelli et al; Cancer Research 60: 944-949, 2000 |
| 0076 | CAIS | Deletion | 3-8 | | | ⇒ | ⇒ | | | | | | | | Female | Normal | | Brown et al, Eur J Pediatr (Suppl 2) 152: S62, 1993 |
| 0077 | MAIS | Deletion | 4 LBD | | | ⇒ | ⇒ | | | | | | | Azoospermia | Male | Normal | neg | Aiken et al; Am J Obs & Gyn. 165: 1891-1894, 1991 |
| 0078 | CAIS | Deletion | 4 LBD | * | | ⇒ | ⇒ | | | | | | | 13 nt deletion causing frameshift and stop at codon 783 | Female | Normal | pos | Lobaccaro et al; Mol & Cellular Endocrinology 111: 21-8, 1995 |
| 0306 | Prostate cancer | Substitute | 4 | | | 629 2248 | Arg⇒Gln CGG⇒CAG | | | | | | | 1 of 6 of hormone-independent D2 patients-somatic mut | Male | Normal | | Wang et al; Japanese J of Urology 88: 550-556 1997 |
| 0079 | Prostate cancer | Substitute | 4 | | | 630 2251 | Lys⇒Thr AAG⇒ACG | | | | | | | Also Lys717Glu mut, (AAGtoGAG) + silent mut in 701. Som mut | Male | Normal | | Tilley et al; Clinical Cancer Res. 2: 277-285, 1996 |
| 0400 | CAIS | Substitute | 4 LBD | | | 640 2280 | Gln⇒Stop CAG⇒TAG | | | zero | | | | | Female | Normal | | Yaegashi et al; Tohoku J of Exp Med 187: 263-272, 1999 |
| 0429 | CAIS | Substitute | 4 LBD | | | 640 2280 | Gln⇒Stop CAG⇒TAG | | | zero | | | | also Trp751Stop mut, (TGGtoTGA) 47XXY Muts on both X's | Female | Normal | | Uehara et al; Am J Med Genet. 86: 107-111, 1999 |
| 0080 | PAIS | Substitute | 4 LBD | | | 645 2296 | Ala⇒Asp GCT⇒GAT | | | | | | | | Male | Ambiguous | | Hiort et al; Am J Med Genet. 63: 218-222, 1996 |
| 0334 | Normal | Substitute | 4 LBD | | | 645 2296 | Ala⇒Asp GCT⇒GAT | | | | | | | | Male | Normal | | Nordenskjold et al; Human Mutation. 11: 339, 1998 |
| 0081 | Prostate cancer | Substitute | 4 LBD | | | 647 2302 | Ser⇒Asn AGC⇒AAC | | | | | | | +Gly724Asp, Leu880 Gln & Ala896Thr.mut Somatic mutations | Male | Normal | | Taplin et al; New England J Med 332: 1393-1398, 1995 |
| 0555 | PAIS | Substitute | 4 LBD | | | 653 2319 | Glu⇒Lys GAG⇒AAG | 20 | | | | | | Also in family with CAH with no | Male | Ambiguous | | Lundberg et al; J Clin Endocrinol & Metab 87: |

TABLE 5-continued

| Accession # | Phenotype | Mutation type | Pathogenicity Exon Domain | Pathogenicity prov-en | Pathogenicity CpG hot spot | Amino acid | Position Change Base | Position Change Amino acid | Exon 1 tracts Poly Gln # | Exon 1 tracts Poly Gly # | Androgen Binding Bmax | Androgen Binding Kd | Androgen Binding k | Ther-mo-labile | Comments | Sex of rearing | External Genitalia | Family history | Reference |
|---|---|---|---|---|---|---|---|---|---|---|---|---|---|---|---|---|---|---|---|
| 0517 | CAIS | Substitute | 4 LBD | | | 657 2231 | CAG⇒TAG | Gln⇒Stop | | | | | | | androgen insensitivity | Female | Normal | | Chavez et al; Clin Genet 59:: 185-188, 2001 |
| 0082 | PAIS | Substitute | 4 LBD | | | 664 2353 | ATT⇒AAT | Ile⇒Asn | 22 | 22 | low | | norm | | | Male | Normal | | Pinsky et al; Clin Inv Med 15: 456, 1992 |
| 0083 | Prostate cancer | Substitute | 4 LBD | | | 670 2371 | CAG⇒CGG | Gln⇒Arg | | | | | | | Also Ser791Pro (TCT to CCT) mut. Somatic mutation | Male | Normal | | Tilley et al; Clinical Cancer Res. 2: 277-285, 1996 |
| 0084 | PAIS | Substitute | 4 LBD | | | 671 2374 | CCC⇒CAC | Pro⇒His | | | | | | | | Male | Ambiguous | | Hiort et al; Am J Med Genet. 63: 218-222, 1996 |
| 0085 | Prostate cancer | Substitute | 4 LBD | | | 672 2377 | ATC⇒ACC | Ile⇒Thr | | | | | | | Somatic mutation | Male | Normal | | Tilley et al; Clinical Cancer Res. 2: 277-285, 1996 |
| 0086 | CAIS | Substitute | 4 LBD | | | 677 2392 | CTG⇒CCG | Leu⇒Pro | | | zero | | | | | Female | Normal | pos | Belsham et al; Human Mutation 5: 28-33, 1995 |
| 0087 | CAIS | Substitute | 4 LBD | | | 681 2403 | GAG⇒AAG | Glu⇒Lys | | | | | | | | Female | Normal | | Hiort et al; J Clin Endocrinol Metab 77: 262-266, 1993 |
| 0394 | CAIS | Substitute | 4 LBD | | | 681 2403 | GAG⇒AAG | Glu⇒Lys | | | | | | | Germ cell tumour in undescended testis | Female | Normal | | Chen et al; Human Reproduction 14: 664-670, 1999 |
| 0534 | PAIS | Substitute | 4 LBD | | | 682 2406 | CCA⇒ACA | Pro⇒Thr | | | low | | | | | Female | Ambiguous | | Chavez et al; J Hum Genet. 46: 560-565, 2001 |
| 0089 | Prostate cancer | Substitute | 4 LBD | | | 683 2410 | GGT⇒GCT | Gly⇒Ala | | | | | | | Somatic mutation - transactivation normal | Male | Normal | | Koivisto et al; Cancer Research 57: 314-319, 1997 |
| 0090 | CAIS | Substitute | 4 LBD | | | 684 2412 | GTA⇒ATA | Val⇒Ile | | | zero | | | | | Female | Normal | | Mebarki et al; 75th US Endo Soc Meeting, Abstr 602, 1993 |
| 0091 | PAIS | Substitute | 4 LBD | | | 686 2418 | TGT⇒CGT | Cys⇒Arg | | | | | | | | Male | Ambiguous | | Hiort et al; Am J Med Genet. 63: 218-222, 1996 |
| 0092 | PAIS | Substitute | 4 LBD | | | 687 2422 | GCT⇒GTT | Ala⇒Val | | | | | | | | Male | Ambiguous | | Hiort et al; Am J Med Genet. 63: 218-222, 1996 |
| 0093 | CAIS | Substitute | 4 LBD | | | 688 | GGA⇒ | Gly⇒Glu | | | zero | | | | de novo mutation | Female | Normal | neg | Hiort et al; J Pediatrics 132: 939-943, 1998 |
| 0446 | CAIS | Substitute | 4 LBD | | | 688 2424 | GGA⇒TGA | Gly⇒Stop | | | | | | | | Female | Normal | | Ahmed et al; J Clin Endocrinol & Metab 85: 658-665, 2000 |
| 0094 | PAIS | Deletion | 4 LBD | | | 690 2428-30 | ACG⇒0 | Asp⇒0 | | | | | | | | Female | Normal | | Schwartz et al; Horm Res 41: 117 Abstr 244, 1994 |
| 0095 | CAIS | Deletion | 4 | | | 692 | | Asn⇒0 | | | normal | high | | * | Three nucleotide | Female | Normal | | Batch et al; Hum Mol |

TABLE 5-continued

| Ac-ces-sion # | Phenotype | Mutation type | Pathogenicity | | | | Exon Domain | Position Change | | | Exon 1 tracts | | Androgen Binding | | | Comments | Sex of rearing | External Genitalia | Family history | Reference |
|---|---|---|---|---|---|---|---|---|---|---|---|---|---|---|---|---|---|---|---|---|
| | | | prov-en | CpG | hot spot | | | Amino acid Base | Amino acid Base | Position Change | Poly Gln # | Poly Gly # | Bmax | Kd | k | Ther-mo-labile | | | | |
| 0096 | CAIS | Substitute | * | | | 4 | LBD | 2436-8 | AAC⇒0 | AAC⇒0 | | | | | | | deletion | Female | Normal | | Genet 1: 497, 1992 |
| 0097 | CAIS | Substitute | * | | * | 4 | LBD | 695 2445 | Asp⇒His | GAC⇒CAC | | | low | | | | | Female | Normal | neg | Ris-Stalpers et at; Mol Endocrinol 5: 1562, 1991 |
| 0098 | PAIS | Substitute | | | * | 4 | LBD | 695 2445 | Asp⇒Asn | GAC⇒AAC | | | normal | normal | high | | mutation found in two unrelated families | Female | Normal | pos | Ris-Stalpers et at; Mol Endocrinol 5: 1562, 1991 |
| 0335 | CAIS | Substitute | | | | 4 | LBD | 695 2445 | Asp⇒Asn | GAC⇒AAC | 21 | | | | | | de novo mutation | Female | Ambiguous | | Hiort et al: J Pediatrics 132: 939-943, 1998 |
| 0447 | CAIS | Substitute | | | | 4 | LBD | 695 2446 | Asp⇒Val | GAC⇒GTC | | | | | | | mtuation found in two siblings | Female | Normal | pos | Dork et al; Human Mutation 11: 337-339, 1998 |
| 0448 | CAIS | Substitute | | | | 4 | LBD | 700 2460 | Leu⇒Met | TTG⇒ATG | | | | | | | | Female | Normal | | Ahmed et al; J Clin Endocrinol & Metab 85: 658-665, 2000 |
| 0518 | PAIS | Substitute | | | | 4 | LBD | 701 2463 | Leu⇒Phe | CTC⇒TTC | | | | | | | | Female | Normal | | Ahmed et al; J Clin Endocrinol & Metab 85: 658-665, 2000 |
| 0099 | Prostate cancer | Substitute | | | | 4 | LBD | 701 2463 | Leu⇒Ile | CTC⇒ATC | | | | | | | Somatic mutation | Male | Normal | | Chavez et al; Clin Genet 59:: 185-188, 2001 |
| 0326 | Prostate cancer | Substitute | | | | 4 | LBD | 701 2464 | Leu⇒His | CTC⇒CAC | | | | | | | Somatic mutation | Male | Normal | | Suzuki et al; J Steroid Biochem Molec Biol 46: 759, 1993 |
| 0408 | MDA PCa-Za | Substitute | | | | 4 | LBD | 701 2464 | Leu⇒His | CTC⇒CAC | | | normal | low | | | Som. mut. Prostate cancer cell line. Also has Thr877Ala | Male | Normal | | Watanabe et al; Jpn J Clin Oncol 27: 389-393, 1997 |
| 0100 | CAIS | Substitute | | | | 4 | LBD | 701 2464 | Leu⇒His | CTC⇒CAC | | | | | | | | Male | Normal | | Zao et al; J of Urology 162: 2192-2199, 1999 |
| 0101 | PAIS | Substitute | | | * | 4 | LBD | 702 2466 | Ser⇒Ala | TCT⇒GCT | | | zero | | | | | Female | Normal | | Pinsky et al; Clin Inv Med 15: 456, 1992 |
| 0449 | CAIS | Substitute | * | | | 4 | LBD | 703 2469 | Ser⇒Gly | AGC⇒GGC | | | low | high | | | | Male | Ambiguous | | Radnayr et al; J of Urology 158: 1553-1556, 1997 |
| 0559 | CAIS | Substitute | | | | 4 | LBD | 703 2469 | Ser⇒Gly | AGC⇒GGC | | | | | | | Sister a carrier | Female | Normal | | Ahmed et al; J Clin Endocrinol & Metab 85: 658-665, 2000 |
| 0102 | CAIS | Substitute | | | | 4 | LBD | 705 2475 | Asn⇒Tyr | AAT⇒TAT | | | zero | | | | | Female | Normal | | Sills et al; Int J Mol Med 9: 45-48, 2002 |
| 0103 | CAIS | Substitute | | | | 4 | LBD | 705 2476 | Asn⇒Ser | AAT⇒AGT | | | zero | | | | | Female | Normal | | Pinsky et al; Clin Inv Med 15: 456, 1992 |
| 0104 | CAIS | Substitute | | | | 4 | LBD | 705 2476 | Asn⇒Ser | AAT⇒AGT | | | | | | | | Female | Normal | | DeBellis et al; Mol Endocrinol 6: 1909-20, 1992 |
| | CAIS | Substitute | | | | 4 | LBD | 705 2476 | Asn⇒Ser | AAT⇒AGT | | | | | | | Mutation found in two unrelated families | Female | Normal | | Quigley et al: Endocrine Reviews 16: 271, 1995 |

TABLE 5-continued

| Accession # | Phenotype | Mutation type | Exon Domain | Pathogenicity proven | CpG | hot spot | Amino acid Base | Position Change Amino acid Base | Exon 1 tracts Poly Gln # | Poly Gly # | Bmax | Kd | k | Thermolabile | Comments | Sex of rearing | External Genitalia | Family history | Reference |
|---|---|---|---|---|---|---|---|---|---|---|---|---|---|---|---|---|---|---|---|
| 0482 | PAIS | Substitute | 4 LBD | | | | 705 2476 | Asn⇒Ser AAT⇒AGT | | | normal | high | | | | | | | Ahmed et al; J Clin Endocrinol & Metab 85: 658-665, 2000 |
| 0105 | CAIS | Substitute | 4 LBD | * | | | 707 2482 | Leu⇒Arg CTG⇒CGG | | | | | | | | Female | Normal | | Lumbroso et al; J Clin Endo & Metab 81: 1984-1988, 1996 |
| 0106 | PAIS | Substitute | 4 LBD | | | | 708 2485 | Gly⇒Ala GGA⇒GCA | | | | | | | | Male | Ambiguous | | Hiort et al: Hum Mol Genet 3: 1163-1166 1994 |
| 0314 | PAIS | Substitute | 4 LBD | | | | 708 2485 | Gly⇒Ala GGA⇒GCA | | | | | | | Severe hypospadias | Male | Ambiguous | | Albers et al; J of Pediatrics 131: 388-392, 1997 |
| 0107 | CAIS | Substitute | 4 LBD | | | | 708 2485 | Gly⇒Val GGA⇒GTA | | | zero | | | | | Male | Ambiguous | pos | Auchus et al: 77th US Endo Soc Meeting, Abstr P1-508 1995 |
| 0450 | CAIS | Substitute | 4 LBD | | | | 710 2491 | Arg⇒Thr AGA⇒ACA | | | zero | | | | | Female | Normal | | Ahmed et al; J Clin Endocrinol & Metab 85: 658-665, 2000 |
| 0525 | PAIS | Substitute | 4 LBD | * | | | 711 2493 | Gln⇒Glu CAG⇒GAG | | | v low | | | | altered AR specificity 2x increased affinity for E2. | Female | Ambiguous | pos | Lumbroso et al. 83rd US Endo Soc Meeting, Abstr P2-29, 2001 |
| 0535 | PAIS | Substitute | 4 LBD | * | | | 711 2493 | Gln⇒Glu CAG⇒GAG | | | normal | | | | | Female | Ambiguous | pos | Chavez et al; J Hum Genet. 46: 560-565, 2001 |
| 0108 | PAIS | Substitute | 4 LBD | * | | | 712 2496 | Leu⇒Phe CTT⇒GTT | | | normal | high | | | Phenotypic diversity brother of 505 & 506 Testost-induced norm. | Male | Ambiguous | pos | Hiort et al: Am J Med Genet. 63: 218-222, 1996 |
| 0505 | PAIS | Substitute | 4 LBD | * | | | 712 2496 | Leu⇒Phe CTT⇒GTT | | | normal | high | | | Phenotypic diversity brother of 108 & 506 Testost-induced norm. | Male | Ambiguous | pos | Hiort et al; J Clin Endocrinol & Metab 85: 3245-3250, 2000 |
| 0506 | PAIS | Substitute | 4 LBD | * | | | 712 2496 | Leu⇒Phe CTT⇒GTT | | | normal | high | | | Phenotypic diversity brother of 505 & 108 Testost-induced norm. | Male | Ambiguous | pos | Hiort et al; J Clin Endocrinol & Metab 85: 3245-3250, 2000 |
| 0507 | PAIS | Substitute | 4 LBD | * | | | 712 2496 | Leu⇒Phe CTT⇒GTT | | | normal | | | | Phenotypic diversity uncle of 108, 505, 506 Testost-induced norm. | Male | Ambiguous | pos | Hiort et al; J Clin Endocrinol & Metab 85: 3245-3250, 2000 |
| 0109 | Prostate cancer | Substitute | 4 LBD | * | | | 715 2507 | Val⇒Met GTG⇒ATG | | | normal | | | | Somatic mutation. Receptor showed a gain in function | Male | Normal | | Culig et al; Mol Endocrinol 7: 1541-1550 1993 |
| 0110 | Prostate cancer | Substitute | 4 LBD | | | * | 715 2507 | Val⇒Met GTG⇒ATG | | | normal | | | | Somatic mutation. Receptor showed a gain in function | Male | Normal | | Bubley et al 87th Am Assoc Cancer Res Meet Abstr. 1680, 1996 |
| 0111 | CAIS | Substitute | 4 LBD | | | | 718 2516 | Trp⇒Stop TGG⇒TGA | | | zero | | | | | Female | Normal | pos | Sai et al: Am J Hum Genet 46: 1095, 1990 |
| 0112 | Prostate cancer | Substitute | 4 LBD | | | | 720 2520 | Lys⇒Glu AAG⇒GAG | | | | | | | Somatic mutation- Bone metastases of | Male | Normal | | Kleinerman et al; J of Urology 155: 624A, |

TABLE 5-continued

| Ac-ces-sion # | Phenotype | Mutation type | Pathogenicity Exon Domain | Pathogenicity prov-en | CpG hot spot | Position Change Amino acid Base | Position Change Amino acid Base | Exon 1 tracts Poly Gln # | Exon 1 tracts Poly Gly # | Androgen Binding Bmax | Androgen Binding Kd | Androgen Binding k | Ther-mo-labile | Comments | Sex of rearing | External Genitalia | Family history | Reference |
|---|---|---|---|---|---|---|---|---|---|---|---|---|---|---|---|---|---|---|
| 0113 | Prostate cancer | Substitute | 4 LBD | | | 721 2523 | Ala⇒Thr GCC⇒ACC | | | | | | | Prostate cancer Somatic mutation in 20% of isolates in initial cloning | Male | Normal | | Taplin et al; New England J Med 332: 1393-1398, 1995 |
| 0114 | CAIS | Substitute | 4 LBD | | | 722 2526 | Leu⇒Phe TTG⇒ | | | | | | | | Female | Normal | | Hiort et al; Am J Med Genet. 63: 218-222, 1996 |
| 0451 | CAIS | Substitute | 4 LBD | | | 723 2529 | Pro⇒Ser CCT⇒TCT | | | normal | high | | | | Female | Normal | | Ahmed et al; J Clin Endocrinol & Metab 85: 658-665, 2000 |
| 0452 | CAIS | Substitute | 4 LBD | | | 724 2532 | Gly⇒Ser GGC⇒AGC | | | zero | | | | | Female | Normal | | Ahmed et al; J Clin Endocrinol & Metab 85: 658-665, 2000 |
| 0453 | CAIS | Substitute | 4 LBD | | | 724 2533 | Gly⇒Asp GGC⇒GAC | | | zero | | | | | Female | Normal | | Ahmed et al; J Clin Endocrinol & Metab 85: 658-665, 2000 |
| 0115 | CAIS | Deletion | 4-8 LBD | | | | ⇒ ⇒ | | | zero | | | | | Female | Normal | | Brown et al; Proc Natl Acad Sci 85: 8151, 1988 |
| 0116 | CAIS | Deletion | 5 LBD | | | | ⇒ ⇒ | | | zero | | | | Affected aunt deleted for exons 6 and 7 only. | Female | Normal | pos | Maclean et al; J Clin Invest, 91: 1123, 1993 |
| 0117 | CAIS | Substitute | 5 LBD | | | | Tyr⇒Arg ⇒ | | | zero | | | | | Female | Normal | | Marcelli et al; 74th US Endo Soc Meetings; Abstr. 224, 1992 |
| 0118 | PAIS | Substitute | 5 LBD | | | 725 2535 | Phe⇒Leu TTC⇒CTC | | | normal | normal | | | | Female | Normal | | Quigley et al; Endocrin Reviews 16: 271, 1995 |
| 0391 | PAIS | Substitute | 5 LBD | | | 725 2535 | Phe⇒Leu TTC⇒CTC | | | | | | | Hypospadia and cryptorchidism | Male | Ambiguous | pos | Nordenskjold et al Urological Res, 27: 49-55, 1999 |
| 0119 | Prostate cancer | Substitute | 5 LBD | * | | 726 2539 | Arg⇒Leu CGC⇒CTC | | | normal | normal | | | Germ line mutation present in offspring | Male | Normal | pos | Elo et al; J Clin Endorinol Metab, 80: 3494-3500, 1995 |
| 0508 | Prostate cancer | Substitute | 5 LBD | * | | 726 2539 | Arg⇒Leu CGC⇒CTC | | | | | | | Estimated that 2% of Finnish CAP patients have this mutation | Male | Normal | pos | Mononen et al; Cancer Res 60: 6479-6481, 2000 |
| 0120 | MAIS | Substitute | 5 LBD | | | 727 2543 | Asn⇒Lys AAC⇒AAG | | | | | | | Oligospermia | Male | Normal | | Yong et al; Lancet, 344: 826-827, 1994 |
| 0121 | PAIS | Substitute | 5 LBD | | | 728 2545 | Leu⇒Ser TTA⇒TCA | | | low | | | * | | | | | McPhaul et al; J Clin Inv, 90: 2097, 1992 |
| 0122 | Prostate Cancer | Substitute | 5 LBD | | * | 730 2550 | Val⇒Met GTG⇒ATG | | | | | | | Somatic mutation | Male | Normal | | Newmark et al; Proc Natl AcadSci 89: 6319, 1992 |
| 0123 | Prostate Cancer | Substitute | 5 LBD | | * | 730 2550 | Val⇒Met GTG⇒ATG | | | | | | | Somatic mutation | Male | Normal | | Petersiel et al; Int J Cancer 63: 544-550, 1995 |
| 0310 | CAIS | Substitute | 5 | | | 732 | Asp⇒Asn | 19 | | | | | | | Female | Normal | | Ko et al; J Reprod. |

TABLE 5-continued

| Acces-sion # | Phenotype | Mutation type | Pathogenicity | | | | Position Change | | | Exon 1 tracts | | Androgen Binding | | | Ther-mo-labile | Comments | Sex of rearing | External Genitalia | Family history | Reference |
|---|---|---|---|---|---|---|---|---|---|---|---|---|---|---|---|---|---|---|---|---|
| | | | Exon Domain | prov-en | CpG | hot spot | Amino acid Base | Amino acid Base | Position Change | Poly Gln # | Poly Gly # | Bmax | Kd | k | | | | | | |
| 0125 CAIS | CAIS | Substitute | 5 LBD | | * | | 732 2556 | Asp⇒Tyr GAC⇒AAC GAC⇒TAC | | | | | high | | | | Female | Normal | | Med 42: 424-427, 1997 Brown et al; 74th US Endo Soc Meeting, Abstr 1506, 1992 |
| 0126 CAIS | CAIS | Substitute | 5 LBD | | | | 732 2556 | Asp⇒Tyr GAC⇒TAC | | | | zero | | | | | Female | Normal | | Pinsky et al; Clin Inv Med 15: 456, 1992 |
| 0127 CAIS | CAIS | Substitute | 5 LBD | | | | 732 2556 | Asp⇒Tyr GAC⇒TAC | | | | | | | | | Female | Normal | | Ghirri and Brown; Pediatr Res 33, Abstr 95, 1993 |
| 0124 CAIS | CAIS | Substitute | 5 LBD | | | | 732 2556 | Asp⇒Asn GAC⇒AAC | | | | | high | | | | Female | Normal | | Brown et al; 74th US Endo Soc Meeting, Abstr 1506, 1992 |
| 0128 PAIS | PAIS | Substitute | 5 LBD | | | | 733 2561 | Gln⇒His CAG⇒CAT | | | | | | | | This patient was a mosaic for wt. & mut. alleles-de novo mut. | Female | Ambiguous | neg | Hiort et al; J Pediatrics 132: 939-943, 1998 |
| 0129 PAIS | PAIS | Substitute | 5 LBD | | | | 737 2571 | Ile⇒Thr ATT⇒ACT | | | | low | | | | | Female | Normal | | Quigley et al; Endocrin Reviews 16: 271, 1995 |
| 0530 CAIS | CAIS | Substitute | 5 LBD | | * | | 739 2577 | Tyr⇒Asp TAC⇒GAC | | | | zero | | | | no transactivation in COS-1 cells | Female | Normal | | Suzuki et al. Int. J Andrology 24: 183-188, 2001 |
| 0130 CAIS | CAIS | Substitute | 5 LBD | | * | | 741 2583 | Trp⇒Arg TGG⇒CGG | | | | low | | | | | Female | Normal | neg | Marcelli et al; J Clin Invest 94: 1642-1650, 1994 |
| 0360 Prostate cancer | Prostate cancer | Substitute | 5 LBD | | | | 741 2584 | Trp⇒Stop TGG⇒TAG | | | | | | | | Somatic mutation | Male | Normal | | Takahashi et al; Cancer Research 55: 1621-1624, 1995 |
| 0552 Prostate cancer | Prostate cancer | Substitute | 5 LBD | | | | 741 2584 | Trp⇒Cys TGG⇒TGG | | | | | | high | | Treated with bicalutamide - somatic mutation | Male | Normal | | Taplin et al; 37th meeting ASCO 20: Abstr. 1738 |
| 0131 PAIS | PAIS | Substitute | 5 LBD | | | | 742 2586 | MeT⇒Val ATG⇒GTG | | | | normal | high | | | | Female | Normal | | Ris-Stalpers et al; Pediatric Res. 36: 227-234, 1994 |
| 0341 PAIS | PAIS | Substitute | 5 LBD | | | | 742 2586 | MeT⇒Val ATG⇒GTG | | | | normal | normal | | * | | Male | Normal | pos | Melo et al; 80th US Endo Soc Meeting Abstr P2-44, 1998 |
| 0132 PAIS | PAIS | Substitute | 5 LBD | | | | 742 2588 | MeT⇒Ile ATG⇒ATA | | | | | | | * | | Female | Ambiguous | | Batch et al; Hum Mol Genet 1: 497, 1992 |
| 0519 CAIS | CAIS | Substitute | 5 LBD | | | | 743 2589 | Gly⇒Arg GGG⇒CGG | | | | | | | | | Female | Normal | | Chavez et al; Clin Genet 59:: 185-188, 2001 |
| 0133 PAIS | PAIS | Substitute | 5 LBD | | * | | 743 2590 | Gly⇒Val GGG⇒GTG | | | | low | | high | | Transcription only at high conc of androgen | Female | Ambiguous | | Georget et al; J Clin Endocrinol & Metab 83: 3597-3603, 1998 |
| 0134 PAIS | PAIS | Substitute | 5 LBD | | | | 743 2590 | Gly⇒Val GGG⇒GTG | | | | | | | | | Female | Normal | | Nakao et al; J Clin Endocrinol Metab 77: 103-107, 1993 |
| 0414 CAIS | CAIS | Substitute | 5 | | | | 743 | Gly⇒Val | | | | zero | | | | de novo mutation | Female | Normal | | Lobaccaro et al; J |

TABLE 5-continued

| Acces-sion # | Phenotype | Mutation type | Pathogenicity Exon Domain | Pathogenicity prov-en | CpG hot spot | Position Change Amino acid Base | Position Change Amino acid Base | Position Change Amino Base | Exon 1 tracts Poly Gln # | Exon 1 tracts Poly Gly # | Androgen Binding Bmax | Androgen Binding Kd | Androgen Binding k | Ther-mo-labile | Comments | Sex of rearing | External Genitalia | Family history | Reference |
|---|---|---|---|---|---|---|---|---|---|---|---|---|---|---|---|---|---|---|---|
| 0536 | CAIS | Substitute | 5 LBD | | | | | 2590 GGG⇒GTG | | | normal | | | | | Female | Normal | | Steroid Biochem & Mol Biol. 44: 211-216, 1993 |
| 0361 | Prostate cancer | Deletion | 5 LBD | | | 743 | Gly⇒Glu CGG⇒GAG | 2590 | | | | | | | Frameshift-somatic mut.-separate tumor in same indv. as 0362 | Male | Normal | | Chavez et al; J Hum Genet. 46: 560-56, 2001 Takahashi et al; Cancer Research 55: 1621-1624, 1995 |
| 0135 | CAIS | Substitute | 5 LBD | | | 743 | Gly⇒Gly GGAG⇒GGC | 2591 | | | | | | | | | | | Brinkmann et al; J Steroid Biochem & Mol Biol 53: 443, 1995 |
| 0362 | Prostate cancer | Substitute | 5 LBD | | | 744 | Leu⇒Phe CTC⇒TTC | 2592 | | | | | | | | | | | |
| 0136 | PAIS | Substitute | 5 LBD | | | 744 | Leu⇒Phe CTC⇒TTC | 2592 | | | | | | | Somatic mutation-separate tumor in same indv. as 0361 | Male | Normal | | Takahashi et al; Cancer Research 55: 1621-1624, 1995 |
| 0137 | PAIS | Substitute | 5 LBD | | | 745 | Met⇒Thr ATG⇒ACG | 2597 | | | zero | | | | | | | | Ris-Stalpers et al; Pediatric Res 36: 227-234, 1994 |
| 0138 | PAIS | Substitute | 5 LBD | | | 746 | Val⇒Met GTG⇒ATG | 2598 | | | | | | | | Male | Ambiguous | | Brown et al; 74th US Endo Soc Meeting, Abstr 1506, 1992 |
| 0492 | Prostate cancer | Substitute | 5 LBD | | | 746 | Val⇒Met GTG⇒ATG | 2598 | | | | | | | Also Ser865Pro; Gln867Stop and Gln919Arg; Som mut Abnormal dissociation | Male | Normal | | Hiort et al; Am J Med Genet. 63: 218-222 1996 |
| 0139 | PAIS | Substitute | 5 LBD | * | | 748 | Ala⇒Thr GCC⇒ACC | 2604 | | | low | | high | | | | | | Marcelli et al; Cancer Research 60: 944-949, 2000 |
| 0363 | Prostate cancer | Substitute | 5 LBD | | | 748 | Ala⇒Asp GCC⇒GAC | 2605 | | | | | | | Somatic mutation | Male | Normal | | Marcelli et al; J Clin Invest 94: 1642-1650, 1994 |
| 0140 | CAIS | Substitute | 5 LBD | | | 748 | Ala⇒Val GCC⇒GTC | 2605 | | | | | | | | Female | Normal | pos | Takahashi et al; Cancer Research 55: 1621-1624, 1995 |
| 0141 | CAIS | Substitute | 5 LBD | | | 749 | Met⇒Val ATG⇒GTG | 2607 | | | | | | | | Female | Normal | pos | DeBellis et al; Mol Endocrinol 6: 1909-20, 1992 |
| 0483 | PAIS | Substitute | 5 LBD | | | 749 | Met⇒Val ATG⇒GTG | 2607 | | | normal | high | | | | | | | Jakubiczka et al; Hum Genet 90: 311-2, 1992 |
| 0364 | Prostate cancer | Substitute | 5 LBD | | | 749 | Met⇒Ile ATG⇒ATA | 2609 | | | | | | | Somatic mutation | Male | Normal | | Ahmed et al; J Clin Endocrinol & Metab 85: 658-665, 2000 |
| 0365 | Prostate cancer | Substitute | 5 LBD | | | 750 | Gly⇒Ser GGC⇒AGC | 2610 | | | | | | | Somatic mutation | Male | Normal | | Takahashi et al; Cancer Research 55: 1621-1624, 1995 |
| 0142 | CAIS | Substitute | 5 | * | | 750 | Gly⇒Asp | | | | vlow | | | | Mutation found in two | Female | Normal | | Bevan et al; J Steroid |

TABLE 5-continued

| Acces- sion # | Phenotype | Mutation type | Exon Domain | Pathogenicity prov- en | CpG | hot spot | Amino acid Base | Position Change Amino acid Base | Exon 1 tracts Poly Gln # | Poly Gly # | Androgen Binding Bmax | Kd | k | Ther- mo- labile | Comments | Sex of rearing | External Genitalia | Family history | Reference |
|---|---|---|---|---|---|---|---|---|---|---|---|---|---|---|---|---|---|---|---|
| 0143 | CAIS | Substitute | 5 LBD | | | | 2611 | GGC⇒GAC | | | | | | | unrelated patients | | | | Biochem Molec. Biol 61:19-26, 1997 |
| 0144 | CAIS | Substitute | 5 LBD | | | | 750 2611 | Gly⇒Asp GGC⇒GAC | | | | | | | | Female | Normal | | Brown et al; 74th US Endo Soc Meeting Abstr 1506, 1992 |
| 0366 | Prostate cancer | Substitute | 5 LBD | | | | 751 2613 | Trp⇒Arg TGG⇒AGG | | | | | | | | Female | Normal | | Brinkmann et al; J Steroid Biochem Mol Biol 53: 443, 1995 |
| 0367 | Prostate cancer | Substitute | 5 LBD | | | | 751 2614 | Trp⇒Stop TGG⇒TAG | | | | | | | Somatic mutation | Male | Normal | | Takahashi et al; Cancer Research 55: 1621-1624, 1995 |
| 0368 | Prostate cancer | Substitute | 5 LBD | | | | 751 2614 | Trp⇒Stop TGG⇒TAG | | | | | | | Somatic mutation | Male | Normal | | Takahashi et al; Cancer Research 55: 1621-1624, 1995 |
| 0401 | CAIS | Substitute | 5 LBD | | | | 751 2615 | Trp⇒Stop TGG⇒TGA | | | | | | | Somatic mutation | Male | Normal | | Takahashi et al; Cancer Research 55: 1621-1624, 1995 |
| 0145 | CAIS | Substitute | 5 LBD | | | | 751 2615 | Trp⇒Stop TGG⇒TGA | | | zero | | | | | Female | Normal | | Yaegashi et al; Tohoku J of Exp Med 187: 263-272, 1999 |
| 0146 | CAIS | Substitute | 5 LBD | | * | | 752 2616 | Arg⇒Stop CGA⇒TGA | | | zero | | | | | Female | Normal | | Pinsky et al; Clin Inv Med 15: 456, 1992 |
| 0342 | CAIS | Substitute | 5 LBD | | * | | 752 2616 | Arg⇒Stop CGA⇒TGA | | | | | | | | Female | Normal | | Brinkmann et al; J Steroid Biochem Mol Biol 53: 443, 1995 |
| 0402 | CAIS | Substitute | 5 LBD | | * | | 752 2616 | Arg⇒Stop CGA⇒TGA | | | zero | | | | In two different families | Female | Normal | | Melo et al; 80th US Endo Soc Meeting Abstr P2-44, 1998 |
| 0147 | CAIS | Substitute | 5 LBD | | * | | 752 2616 | Arg⇒Stop CGA⇒TGA | | | zero | | | | Mutation found in two unrel. families. | Female | Normal | | Yaegashi et al; Tohoku J of Exp Med 187: 263-272, 1999 |
| 0148 | CAIS | Substitute | 5 LBD | | * | | 752 2617 | Arg⇒Gln CGA⇒CAA | | | | | | | Equivalent to tfm rat | Female | Normal | | Brown et al; 74th US Endo Soc Meeting, Abstr 1506, 1992 |
| 0333 | CAIS | Substitute | 5 LBD | | * | | 752 2617 | Arg⇒Gln CGA⇒CAA | | | | | | | Equivalent to tfm rat | Female | Normal | pos | Evans; J Endocrinol 135 Suppl, Abstr P26, 1992 |
| 0349 | CAIS | Substitute | 5 LBD | | * | | 752 2617 | Arg⇒Gln CGA⇒CAA | | | | | | | | Female | Normal | | Komori et al; Arch Gynecol & Obstetrics 261: 95-100, 1998 |
| 0497 | CAIS | Substitute | 5 LBD | | * | | 752 2617 | Arg⇒Gln CGA⇒CAA | | | | | | | Bilateral testicular tumors | Female | Normal | | Cabral et al; Brazilian J Med & Biol Res. 31: 775-758, 1998 |
| 0149 | CAIS | Substitute | 5 | | | | 754 | Phe⇒Val | | | zero | | | | | Female | Normal | | Sakai et al; International J of Urology 7: 390-392, 2000 |
| | | | | | | | | | | | | | | | | | | | Lobaccaro et al; Hum |

TABLE 5-continued

| Accession # | Phenotype | Mutation type | Exon Domain | Pathogenicity proven | CpG hot spot | Amino acid Base | Position Change Amino acid Base | Exon 1 tracts Poly Gln # | Poly Gly # | Androgen Binding Bmax | Kd | k | Thermo-labile | Comments | Sex of rearing | External Genitalia | Family history | Reference |
|---|---|---|---|---|---|---|---|---|---|---|---|---|---|---|---|---|---|---|
| 0150 | CAIS | Substitute | 5 LBD | | | 2622 | TTC⇒GTC | | | | | | | | Female | Normal | | Mol Genet 2: 1041-1043, 1993 |
| 0369 | Prostate cancer | Substitute | 5 LBD | | | 754 2622 | Phe⇒Val TTC⇒GTC | | | | | | | Somatic mutation | Male | Normal | | Hiort et al; Am J Med Genet. 63: 218-222, 1996 |
| 0151 | PAIS | Substitute | 5 LBD | | | 754 2622 | Phe⇒Leu TTC⇒CTC | | | | | | | | Male | Ambiguous | | Takahashi et al; Cancer Research 55: 1621-1624, 1995 |
| 0152 | PAIS | Substitute | 5 LBD | * | | 754 2624 | Phe⇒Leu TTC⇒TTA | | | normal | high | | * | | Male | Ambiguous | | Hiort et al: Hum Mol Genet 3: 1163-1166 1994 |
| 0370 | Prostate cancer | Substitute | 5 LBD | | | 754 2624 | Phe⇒Leu TTC⇒TTA | | | | | | | Somatic mutation | Male | Normal | | Weidemann et al; Clin Endocrinology 45: 733-739, 1996 |
| 0153 | PAIS | Substitute | 5 LBD | | | 755 2625 | Thr⇒Ala ACC⇒GCC | | | | | | | | Male | Ambiguous | | Takahashi et al; Cancer Research 55: 1621-1624, 1995 |
| 0532 | MAIS | Substitute | 5 LBD | * | | 756 2629 | Asn⇒Ser AAT⇒AGT | | | | high | | | Servere oligospermia-transactivation 38% of wt. | Male | Normal | | Hiort et al: Am J Med Genet. 63: 218-222, 1996 |
| 0300 | Prostate cancer | Substitute | 5 LBD | * | | 756 2629 | Asn⇒Ser AAT⇒AGT | | | | | | | Binds R1881 norm.-transcriptionally inactive-Som mut | Male | Normal | | Giwercman et al. Clin Endocrinol 54: 827-834, 2001 |
| 0493 | Prostate cancer | Substitute | 5 LBD | | | 757 2632 | Val⇒Ala GTC⇒GCC | | | | | | | Somatic mutation | Male | Normal | | James et al; 79th US Endo Soc Meeting, Abstr P2-484, 1997 |
| 0346 | PAIS | Substitute | 5 LBD | * | | 757 2632 | Val⇒Ala GTC⇒GCC | | | normal | | * | high | 50% reduction in transactivation in COS-7 | | | | Marcelli et al; Cancer Research 60: 944-949, 2000 |
| 0371 | Prostate cancer | Substitute | 5 LBD | | | 758 2635 | Asn⇒Thr AAC⇒ACC | | | | | | | Somatic mutation | Male | Normal | | Yong et al; Mol & Cell Endocrinol. 137: 41-50, 1998 |
| 0154 | CAIS | Substitute | 5 LBD | | | 759 2637 | Ser⇒Pro TCC⇒CCC | | | zero | | | | | Female | Normal | | Takahashi et al; Cancer Research 55: 1621-1624, 1995 |
| 0155 | CAIS | Substitute | 5 LBD | | | 759 2638 | Ser⇒Phe TCC⇒TTC | | | zero | | | | | Female | Normal | | DeBellis et al; Mol Endocrinol, 6: 1909-20, 1992 |
| 0156 | CAIS | Substitute | 5 LBD | * | | 762 2646 | Leu⇒Phe CTC⇒TTC | | | zero | | | | | Female | Normal | | Brown et al: 74th US Endo Soc Meeting, Abstr 1506, 1992 |
| 0157 | CAIS | Substitute | 5 LBD | | | 762 2646 | Leu⇒Phe CTC⇒TTC | | | | | | | | Female | Normal | | Bevan et al; J Steroid Biochem Molec. Biol 61: 19-26, 1997 |
| | | | | | | 763 2649 | Tyr⇒His TAC⇒CAC | | | | | | | | | | | Quigley et al: Endocrin. Reviews, 16: 271, 1995 |

TABLE 5-continued

| Acces-sion # | Phenotype | Mutation type | Pathogenicity Exon Domain | Pathogenicity prov-en | CpG hot spot | Amino acid Base | Position Change Amino acid | Position Change Base | Exon 1 tracts Poly Gln # | Exon 1 tracts Poly Gly # | Androgen Binding Bmax | Androgen Binding Kd | Androgen Binding k | Ther-mo-labile | Comments | Sex of rearing | External Genitalia | Family history | Reference |
|---|---|---|---|---|---|---|---|---|---|---|---|---|---|---|---|---|---|---|---|
| 0158 | PAIS | Substitute | 5 LBD | * | | 763 2650 | Tyr⇒Cys | TAC⇒TGC | 12 | | normal | high | | * | PolyGln tract short (only 12 repeats) | Male | Ambiguous | pos | McPhaul et al; J Clin Inv 87: 1413, 1991: Batch&al Arc Dis Ch 68: 453 |
| 0159 | PAIS | Substitute | 5 LBD | | | 763 2650 | Tyr⇒Cys | TAC⇒TGC | | | low | | | | | Male | Ambiguous | | Morono et al; Human Mutation 6: 152-162, 1995 |
| 0405 | PAIS | Substitute | 5 LBD | | | 763 2650 | Tyr⇒Cys | TAC⇒TGC | | | | | | | | Male | Ambiguous | | Batch et al; Arch Disease Child 68: 453, 1993 |
| 0484 | PAIS | Substitute | 5 LBD | | | 763 2650 | Tyr⇒Cys | TAC⇒TGC | | | normal | high | | | | | | | Ahmed et al; J Clin Endocrinol & Metab 85: 658-665, 2000 |
| 0485 | PAIS | Substitute | 5 LBD | | | 763 2650 | Tyr⇒Cys | TAC⇒TGC | | | normal | high | | | | | | | Ahmed et al; J Clin Endocrinol & Metab 85: 658-665, 2000 |
| 0372 | Prostate Cancer | Substitute | 5 LBD | | | 763 2650 | Tyr⇒Cys | TAC⇒TGC | | | | | | | Somatic mutation | Male | Normal | | Takahashi et al; Cancer Research 55: 1621-1624, 1995 |
| 0160 | CAIS | Substitute | 5 LBD | * | | 764 2652 | Phe⇒Leu | TTC⇒CTC | | | low | | high | | | Female | Normal | neg | Marcelli et al; J clin Invest 94: 1642-1650, 1994 |
| 0161 | CAIS | Substitute | 5 LBD | | | 764 2652 | Phe⇒Leu | TTC⇒CTC | | | zero | | | | | Female | Normal | | Ris-Stalpers et al; Pediatric Res, 36; 227-234, 1994 |
| 0162 | CAIS | Substitute | 5 LBD | | * | 764 2654 | Phe⇒Leu | TTC⇒TTG | | | low | normal | | | | Female | Normal | | Pinsky et al; Clin Inv Med, 15: 456, 1992 |
| 0163 | CAIS | Substitute | 5 LBD | * | | 765 2655 | Ala⇒Thr | GCC⇒ACC | | | zero | | | | | Female | Normal | | Bevan et al; J Steroid Biochem Molec. Biol 61: 19-26, 1997 |
| 0164 | CAIS | Substitute | 5 LBD | | * | 765 2655 | Ala⇒Thr | GCC⇒ACC | | | zero | | | | | Female | Normal | | Merkabi et al; 75th US Endo Soc Meeting Abstr 602, 1993 |
| 0165 | CAIS | Substitute | 5 LBD | | * | 765 2655 | Ala⇒Thr | GCC⇒ACC | | | | | | | | Female | Normal | | Sweet et al; Fertil Sterility 58: 703, 1992 |
| 0166 | CAIS | Substitute | 5 LBD | | * | 765 2655 | Ala⇒Thr | GCC⇒ACC | | | | | | | | Female | Normal | | Hiort et al; Am J Med Genet. 63: 218-222, 1996 |
| 0311 | CAIS | Substitute | 5 LBD | | * | 765 2655 | Ala⇒Thr | GCC⇒ACC | 27 | | | | | | | Female | Normal | | Ko et al; J Reprod. Med 42: 424-427, 1997 |
| 0382 | CAIS | Substitute | 5 LBD | | * | 765 2655 | Ala⇒Thr | GCC⇒ACC | | | | | | | | Female | Normal | | Giwereman et al; Human Genetics 103: 529-531, 1998 |
| 0454 | CAIS | Substitute | 5 LBD | | * | 765 2655 | Ala⇒Thr | GCC⇒ACC | | | | | | | | Female | Normal | | Ahmed et al; J Clin Endocrinol & Metab 85: 658-665, 2000 |
| 0455 | CAIS | Substitute | 5 | | * | 765 | Ala⇒Thr | | | | | | | | | Female | Normal | | Ahmed et al; J Clin |

TABLE 5-continued

| Ac-ces-sion # | Phenotype | Mutation type | Pathogenicity Exon Domain | prov-en | CpG | hot spot | Position Change Amino acid Base | Amino acid Base | Exon 1 tracts Poly Gln # | Poly Gly # | Bmax | Androgen Binding Kd | k | Ther-mo-labile | Comments | Sex of rearing | External Genitalia | Family history | Reference |
|---|---|---|---|---|---|---|---|---|---|---|---|---|---|---|---|---|---|---|---|
| 0456 CAIS | | Substitute | 5 LBD | | | | | GCC⇒ACC | | | | | | | | | | | Endocrinol & Metab 85: 658-665, 2000 |
| 0520 PAIS | | Substitute | 5 LBD | | * | | 765 2655 | Ala⇒Thr GCC⇒ACC | | | | | | | | Female | Normal | | Ahmed et al; J Clin Endocrinol & Metab 85: 658-665, 2000 |
| 0167 CAIS | | Substitute | 5 LBD | | | | 765 2655 | Ala⇒Ser GCC⇒TCC | | | | | | | | Female | Normal | | Chavez et al; Clin Genet 59:: 185-188, 2001 |
| 0168 CAIS | | Substitute | 5 LBD | | | | 765 2656 | Ala⇒Val GCC⇒GTC | 20 | | zero | | | | | Female | Normal | | Pinsky et al, Clin Inv Med, 15: 456, 1992 |
| 0457 CAIS | | Substitute | 5 LBD | * | | | 766 2658 | Pro⇒Ser CCT⇒TCT | | | low | high | | | | Female | Normal | pos | Marcelli et al; J Clin Invest 94: 1642-1650. 1994 |
| 0543 CAIS | | Substitute | 5 LBD | | | | 766 2658 | Pro⇒Ser CCT⇒TCT | | | | | | | | Female | Normal | | Ahmed et al; J Clin Endocrinol & Metab 85: 658-665, 2000 |
| 0169 CAIS | | Deletion | 5 LBD | | | | 766 2658 | Pro⇒Ala CCT⇒ATG | | | normal | high | | | | Female | Normal | | Boehmer et al; J Clin Endocrinol & Metab 86: 4151-4160, 2001 |
| 0388 CAIS | | Deletion | 5 LBD | | | | 766 2660 | Pro⇒Pro CCAT⇒CCG | | | | | | | Single nt. deletion causing frameshift & stop in Codon 807 | Female | Normal | pos | Baldazzi et al; Hum Mol Genet 3: 1169-1170, 1994 |
| 0458 CAIS | | Deletion | 5 LBD | | | | 766 2660 | Pro⇒Pro CCAT⇒CCG | | | | | | | Single nt. deletion causing frameshift & stop in Codon 807 | Female | Normal | | Chung et al; Molecules & Cells 8: 741-745, 1998 |
| 0459 CAIS | | Deletion | 5 LBD | | | | 766 2660 | Pro⇒Pro CCAT⇒CCG | | | | | | | Single nt. deletion causing frameshift & stop in Codon 807 | Female | Normal | | Ahmed et al; J Clin Endocrinol & Metab 85: 658-665, 2000 |
| 0561 CAIS | | Deletion | 5 LBD | | | | 766 2660 | Pro⇒Pro CCAT⇒CCG | | | | | | | Single nt. deletion causing frameshift & stop in Codon 807 | Female | Normal | | Ahmed et al; J Clin Endocrinol & Metab 85: 658-665, 2000 |
| 0170 CAIS | | Substitute | 5 LBD | | | | 766 2660 | Pro⇒Pro CCAT⇒CCG | | | v low | | | | Single nt. del framhift & stop in Codon 807 in 2 unrelated individs | Female | Normal | | Guillen et al; An Esp Pediatr 56: 341-352, 2002 |
| 0343 CAIS | | Substitute | 5 LBD | | | | 767 2663 | Asp⇒Glu GAT⇒GAG | | | | | | | | Female | Normal | | Lobaccaro et al; Pediatr Res, 33..Abstr 115, 1993 |
| 0544 PAIS | | Substitute | 5 LBD | | | | 767 2663 | Asp⇒Glu GAT⇒GAG | | | normal | high | | | | Female | Ambiguous | | Melo et al: 80th US Endo Soc Meeting Abstr P2-44, 1998 |
| 0460 CAIS | | Substitute | 5 LBD | | | | 768 2664 | Leu⇒Met CTG⇒ATG | | | | | | | | Female | Normal | | Boehmer et al; J Clin Endocrinol & Metab 86: 4151-4160, 2001 |
| 0171 PAIS | | Substitute | 5 | | | | 768 2665 | Leu⇒Pro CTG⇒CCG | | | | | | | | Female | Ambiguous | | Ahmed et al; J Clin Endocrinol & Metab 85: 658-665, 2000 |
| | | | | | | | 771 | Asn⇒His | | | | | | | | | | | Hiort et al; Hum Mol |

TABLE 5-continued

| Accession # | Phenotype | Mutation type | Pathogenicity Exon Domain | Pathogenicity proven | CpG hot spot | Amino acid Base | Position Change Amino acid | Position Change Base | Exon 1 tracts Poly Gln # | Exon 1 tracts Poly Gly # | Androgen Binding Bmax | Androgen Binding Kd | Androgen Binding k | Ther-mo-labile | Comments | Sex of rearing | External Genitalia | Family history | Reference |
|---|---|---|---|---|---|---|---|---|---|---|---|---|---|---|---|---|---|---|---|
| 0526 | PAIS | | LBD | | | 2673 | | AAT⇒CAT | | | | | | | | Female | Ambiguous | | Genet 3: 1163-1166 1994 |
| | | Substitute | 5 LBD | * | | 771 2673 | Asn⇒His | AAT⇒CAT | | | | high | | | Size & level of expression of AR normal | Female | Ambiguous | | Zhu et al; 83rd US Endo Soc Meeting, Abstr P2-34, 2001 |
| 0172 | CAIS | Substitute | 5 LBD | | | 772 2676 | Glu⇒Stop | GAG⇒TAG | | | zero | | | | | Female | Normal | | Imasaki et al; Endocrine Journal 42: 643-648 1995 |
| 0173 | PAIS | Substitute | 5 LBD | | | 772 2677 | Glu⇒Gly | GAG⇒GGG | | | low | high | | | | Female | Normal | | Tincello et al; Clinical Endocrinology 46: 497-506, 1997 |
| 0174 | PAIS | Substitute | 5 LBD | * | | 772 2677 | Glu⇒Ala | GAG⇒GCG | 25 | 23 | normal | normal | high | | | Male | Ambiguous | | Shkolny et al; J Clin Endocrinol & Metab 84: 805-810, 1999 |
| 0336 | CAIS | Substitute | 6 LBD | * | * | 774 2682 | Arg⇒Cys | CGC⇒TGC | 26 | 23 | normal | normal | | | | Female | Normal | | Prior et al; Am J Hum Genet, 51: 143, 1992 |
| 0176 | CAIS | Substitute | 6 LBD | * | * | 774 2682 | Arg⇒Cys | CGC⇒TGC | 27 | 19 | zero | | | | | Female | Normal | pos | Prior et al; Am J Hum Genet, 51: 143, 1992 |
| 0177 | CAIS | Substitute | 6 LBD | * | * | 774 2682 | Arg⇒Cys | CGC⇒TGC | | | zero | | | | | Female | Normal | | Mebarki et al; 72nd US Endo Soc Meeting, Abstr 791, 1990 |
| 0178 | CAIS | Substitute | 6 LBD | | * | 774 2682 | Arg⇒Cys | CGC⇒TGC | | | | | | | | Female | Normal | | Hiort et al; J Pediatrics 132: 939-943, 1998 |
| 0179 | CAIS | Substitute | 6 LBD | * | * | 774 2682 | Arg⇒Cys | CGC⇒TGC | | | v low | high | | | | Female | Normal | neg | Marcelli et al; J Clin Endocrinol & Metab 73: 318, 1991 |
| 0180 | CAIS | Substitute | 6 LBD | * | * | 774 2682 | Arg⇒Cys | CGC⇒TGC | | | | | | * | mosaic-de novo mutation | Female | Normal | | Jakubiczka et al; Human Mutation 9: 57-61, 1997 |
| 0331 | CAIS | Substitute | 6 LBD | | * | 774 2682 | Arg⇒Cys | CGC⇒TGC | | | | | | * | | Female | Normal | | Komori et al; Arch Gynecol & Obstetrics 261: 95-100, 1998 |
| 0175 | CAIS | Substitute | 6 LBD | * | * | 774 2682 | Arg⇒Cys | CGC⇒TGC | | | v low | | | | | Female | Normal | | Brown et al; Mol Endocrinol, 4: 1759-72, 1990 |
| 0355 | CAIS | Substitute | 6 LBD | | * | 774 2682 | Arg⇒Cys | CGC⇒TGC | | | normal | high | | | mutation found in two unrelated families | Female | Normal | neg | Hiort et al; J Pediatrics 132: 939-943, 1998 |
| 0181 | CAIS | Substitute | 6 LBD | * | * | 774 2683 | Arg⇒His | CGC⇒CAC | | | | | | | | Female | Normal | pos | Prior et al; Am J Hum Genet, 51: 143, 1992 |
| 0182 | CAIS | Substitute | 6 LBD | * | * | 774 2683 | Arg⇒His | CGC⇒CAC | | | low | normal | | | | Female | Normal | | Batch et al; Hum Mol Genet, 1: 497, 1992 |
| 0183 | CAIS | Substitute | 6 LBD | * | * | 774 2683 | Arg⇒His | CGC⇒CAC | | | v low | high | | | | Female | Normal | | DeBellis et al; Mol Endocrinol, 6: 1909-20, 1992 |
| 0184 | CAIS | Substitute | 6 LBD | * | * | 774 2683 | Arg⇒His | CGC⇒CAC | | | | | | | | Female | Normal | | Hiort et al; Am J Med Genet. 63; 218-222, 1996 |

TABLE 5-continued

| Ac-ces-sion # | Phenotype | Mutation type | Exon | Domain | Pathogenicity prov-en | CpG hot spot | Amino acid Base | Position Change Amino acid | Base | Exon 1 tracts Poly Gln # | Poly Gly # | Androgen Binding Bmax | Kd | k | Ther-mo-labile | Comments | Sex of rearing | External Genitalia | Family history | Reference |
|---|---|---|---|---|---|---|---|---|---|---|---|---|---|---|---|---|---|---|---|---|
| 0461 | CAIS | Substitute | 6 | LBD | | * | 774 2683 | Arg⇒His | CGC⇒CAC | | | zero | | | | | Female | Normal | | Ahmed et al; J Clin Endocrinol & Metab 85: 658-665, 2000 |
| 0462 | CAIS | Substitute | 6 | LBD | | * | 774 2683 | Arg⇒His | CGC⇒CAC | | | | | | | | Female | Normal | | Ahmed et al; J Clin Endocrinol & Metab 85: 658-665, 2000 |
| 0185 | PAIS | Substitute | 6 | LBD | | * | 774 2683 | Arg⇒His | CGC⇒CAC | | | | | | | | | | | Quicley et al; Endocrin Reviews 16: 271, 1995 |
| 0186 | CAIS | Substitute | 6 | LBD | | * | 779 2697 | Arg⇒Trp | CGG⇒TGG | | | | | | | | Female | Normal | | Hiort et al; Hum Mol Genet 3: 1163-1166 1994 |
| 0187 | CAIS | Substitute | 6 | LBD | * | * | 779 2697 | Arg⇒Trp | CGG⇒TGG | | | | | | | | Female | Normal | | Morono et al; Human Mutation 6: 152-162, 1995 |
| 0188 | CAIS | Substitute | 6 | LBD | | * | 779 2697 | Arg⇒Trp | CGG⇒TGG | | | | | | | | Female | Normal | | Sinnecker et al; Eur J. Pediatr. 156: 7-14, 1997 |
| 0463 | CAIS | Substitute | 6 | LBD | | * | 779 2697 | Arg⇒Trp | CGG⇒TGG | | | | | | | | Female | Normal | | Ahmed et al; J Clin Endocrinol & Metab 85: 658-665, 2000 |
| 0189 | PAIS | Substitute | 6 | LBD | * | | 780 2702 | Met⇒Ile | ATG⇒ATA | | | normal | high | | * | | Female | Ambiguous | | Bevan et al; Hum Mol Genet, 5: 265-273, 1996 |
| 0190 | PAIS | Substitute | 6 | LBD | | | 780 2702 | Met⇒Ile | ATG⇒ATA | 20 | | normal | high | high | | 1 family member - male. Rest of family females | Female/ Male | Ambiguous | pos | Pinsky et al; Clin Inv Med, 15: 456, 1992 |
| 0191 | PAIS | Substitute | 6 | LBD | | | 780 2702 | Met⇒Ile | ATG⇒ATA | | | | | | | | | | | Brinkmann et al; J Steroid Biochem & Mol Biol 53: 443, 1995 |
| 0192 | PAIS | Substitute | 6 | LBD | | | 780 2702 | Met⇒Ile | ATG⇒ATA | | | low | high | | | A brother to mutation 0305 | Male | Ambiguous | pos | Rodien et al; Endo & Metab 81: 2904-2908, 1996 |
| 0305 | CAIS | Substitute | 6 | LBD | | | 780 2702 | Met⇒Ile | ATG⇒ATA | | | | | | | 2 sisters to mutation 0192 | Female | Normal | pos | Rodien et al; Endo & Metab 81: 2904-2908, 1996 |
| 0193 | CAIS | Substitute | 6 | LBD | | | 780 2702 | Met⇒Ile | ATG⇒ATA | | 23 | | | | | | Female | Normal | | Jakubiczka et al; Human Mutation 9: 57-61, 1997 |
| 0464 | CAIS | Substitute | 6 | LBD | | | 780 2702 | Met⇒Ile | ATG⇒ATA | | | | | | | | Female | Normal | | Ahmed et al; J Clin Endocrinol & Metab 85: 658-665, 2000 |
| 0194 | Prostate cancer | Substitute | 6 | LBD | | | 782 2707 | Ser⇒Asn | AGC⇒AAC | | | | | | | Somatic mutation | Male | Normal | | Tilley et al; 2: Clinical Cancer Res. 2: 277-285, 1996 |
| 0383 | CAIS | Substitute | 6 | LBD | * | | 784 2713 | Cys⇒Tyr | TGT⇒TAT | | | zero | | | | No transactivation capacity | Female | Normal | | Giwerceman et al; Human Genetics 103: 529-531, 1998 |
| 0195 | CAIS | Substitute | 6 | LBD | | * | 786 2718 | Arg⇒Stop | CGA⇒TGA | | | zero | | | | | Female | Normal | | Pinsky et al; Clin Inv Med, 15: 456, 1992 |

TABLE 5-continued

| Ac-ces-sion # | Phenotype | Mutation type | Pathogenicity Exon Domain | Pathogenicity proven | CpG hot spot | Position Change Amino acid Base | Position Change Amino acid Base | Exon 1 tracts Poly Gln # | Exon 1 tracts Poly Gly # | Androgen Binding Bmax | Androgen Binding Kd | Androgen Binding k | Ther-mo-labile | Comments | Sex of rearing | External Genitalia | Family history | Reference |
|---|---|---|---|---|---|---|---|---|---|---|---|---|---|---|---|---|---|---|
| 0557 | CAIS | Substitute | 6 LBD | | * | 786 2718 | Arg⇒Stop CGA⇒TGA | | | | | | | | Female | Normal | | Ignaccack et al; J Appl Genet 43: 109-114, 2002 |
| 0196 | CAIS | Substitute | 6 LBD | * | | 787 2721 | Met⇒Val ATG⇒GTG | | | zero | | | | | Female | Normal | pos | Nakao et al; J Clin Endocrinol Metab, 74; 1152, 1992 |
| 0406 | MAIS | Substitute | 6 LBD | | | 788 2726 | Arg⇒Ser AGG⇒AGT | 24 | 23 | normal | normal | high | | Gynecomastic and infertility | Male | Ambiguous | pos | Lumroso et al 81st. US endo Soc Meetings Abstr. P3-288, 1999 |
| 0197 | MAIS | Substitute | 6 LBD | * | | 790 2730 | Leu⇒Phe CTC⇒TTC | | | normal | low | | * | | Male | Near-normal male | | Tsukada et al; J Clin Endorinol Metab, 79: 1202, 1994 |
| 0198 | MAIS | Substitute | 6 LBD | | | 793 2741 | Glu⇒Asp GAG⇒GAC | | | normal | normal | | | Inconsistent increases in k | Male | Normal | | Pinsky et al; Clin Inv Med, 15: 456, 1992 |
| 0397 | Normal | Substitute | 6 LBD | | | 793 2741 | Glu⇒Asp GAG⇒GAC | | | | | | | Homosexual individual | Male | Normal | | Macke et al; Am J Human Genetics 53: 844-852, 1993 |
| 0199 | CAIS | Substitute | 6 LBD | | | 794 2743 | Phe⇒Ser TTT⇒TCT | | | | | | | | Female | Normal | | Hiort et al; Am J Med Genet. 63: 218-222, 1996 |
| 0200 | CAIS | Substitute | 6 LBD | | | 794 2743 | Phe⇒Ser TTT⇒TCT | | | | | | | | Female | Normal | | Jakubiczka et al Human Mutation 9: 57-61, 1997 |
| 0201 | CAIS | Substitute | 6 LBD | * | | 796 2750 | Trp⇒Stop TGG⇒TGA | | | v low | | | | | Female | Normal | | Marcelli et al; J Clin Invest 85: 1522, 1990 |
| 0202 | PAIS | Substitute | 6 LBD | * | | 798 2754 | Gln⇒Glu CAA⇒GAA | | | normal | normal | | * | | Female | Ambiguous | | Bevan et al; Hum Mol Genet, 5: 265-273, 1996 |
| 0203 | PAIS | Substitute | 6 LBD | | | 798 2754 | Gln⇒Glu CAA⇒GAA | | | normal | normal | | | | | | | Quigley et al; Endocrine Reviews 16: 271, 1995 |
| 0204 | PAIS | Substitute | 6 LBD | | | 798 2754 | Gln⇒Glu CAA⇒GAA | | | | | | | | Female | Ambiguous | | Hiort et al; Am J Med Genet. 63: 218-222, 1996 |
| 0205 | Prostate cancer | Substitute | 6 LBD | | | 798 2754 | Gln⇒Glu CAA⇒GAA | | | | | | | Also present in genomic DNA | Male | Normal | | Evans et al; Prostate 28: 162-171, 1996 |
| 0399 | Prostate cancer | Substitute | 6 LBD | | | 798 2754 | Gln⇒Glu CAA⇒GAA | | | | | | | Somatic mutation Stage 4 tumor | Male | Normal | | Castagnaro et al; Verh. Dtsch. Ges. Path. 77; 119-123, 1993 |
| 0340 | MAIS | Substitute | 6 LBD | * | | 798 2754 | Gln⇒Glu CAA⇒GAA | | | normal | | | | Azospermia | Male | Normal | | Hiort et al; J Clin Endorinol & Metab 85: 2810-2815, 2000 |
| 0381 | MAIS | Substitute | 6 LBD | * | | 798 2754 | Gln⇒Glu CAA⇒GAA | | | normal | | | | Azospermia - defective transactivation | Male | Normal | | Wang et al; J Clin Endocrinol & Metab 83: 4303-4309, 1998 |
| 0542 | CAIS | Deletion | 6 LBD | | | 800 2762 | Thr⇒Thr ACAC⇒ACC | | | | | | | Single nt. deletion causing frameshift & stop in codon 807 | Female | Normal | | Boehmer et al; J Clin Endocrinol & Metab 86: 4151-4160, 2001 |

TABLE 5-continued

| Ac-ces-sion # | Phenotype | Mutation type | Pathogenicity Exon Domain | prov-en | CpG | hot spot | Amino acid Base | Position Change Amino acid | Base | Exon 1 tracts Poly Gln # | Poly Gly # | Androgen Binding Bmax | Kd | k | Ther-mo-labile | Comments | Sex of rearing | External Genitalia | Family history | Reference |
|---|---|---|---|---|---|---|---|---|---|---|---|---|---|---|---|---|---|---|---|---|
| 0521 | PAIS | Substitute | 6 LBD | | | | 802 2767 | Gln⇒Arg | CGG⇒CGG | | | | | | | | | | | Chavez et al; Clin Genet 59::185-188, 2001 |
| 0498 | CAIS | Substitute | 6 LBD | | | | 803 2769 | Glu⇒Lys | GAA⇒AAA | | | zero | zero | | | | Female | Normal | pos | Sawai et al. J Hum Genet 45: 342-345, 2000 |
| 0206 | PAIS | Substitute | 6 LBD | | | | 806 2779 | Cys⇒Tyr | TGC⇒TAC | | | | | | | | | | | Brown et al; Eur J Pediatr 152: (Suppl 2) S62, 1993 |
| 0207 | CAIS | Substitute | 6 LBD | * | | | 807 2781 | Met⇒Val | ATG⇒GTG | | | low | | | | | Female | Normal | | Morono et al; Human Mutation 6: 152-162, 1995 |
| 0208 | CAIS | Substitute | 6 LBD | | | | 807 2782 | Met⇒Arg | ATG⇒AGG | | | zero | | | | | Female | Normal | | Adeyemo et al; Hum Mol Genet, 2: 1809, 1993 |
| 0428 | PAIS | Substitute | 6 LBD | * | | | 807 2782 | Met⇒Thr | ATG⇒ACG | | | low | | | | Treatment with topical DHT restored male genital development | Female | Ambiguous | | Ong et al; Lancet 354: 1444-1445, 1999 |
| 0403 | PAIS | Substitute | 6 LBD | | | | 812 2796 | Leu⇒Phe | CTC⇒TTC | | | | | | | | Female | Normal | | Yaegashi et al; Tohoku J of Exp Med 187: 263-272, 1999 |
| 0209 | PAIS | Substitute | 6 LBD | | | | 814 2803 | Ser⇒Asn | AGC⇒AAC | 20 | | normal | | | | Hormone binding specificity altered. | Female | Ambiguous | | Pinsky et al; Clin Inv Med, 15: 456, 1992 |
| 0210 | MAIS | Substitute | 6 LBD | | | | 814 2803 | Ser⇒Asn | AGC⇒AAC | 20 | | normal | | | | Hormone binding specificity altered | Male | Normal | pos | Pinsky et al; Clin Inv Med, 15: 456, 1992 |
| 0501 | CAIS | Substitute | 7 LBD | | | | 819 2818 | Asp⇒Gln | GAT⇒GGT | | | | | | | | Female | Normal | | Choi et al; Arch Gynecol Obstet 263: 201-205, 200 |
| 0211 | CAIS | Substitute | 7 LBD | * | | | 820 2821 | Gly⇒Ala | GGG⇒GCG | | | normal | high | | * | Also Leu 257 Pro, enhances thermolability | Female | Ambiguous | neg | Tanaka et al; Gynecological Endo. 12: 75-82, 1998 |
| 0212 | PAIS | Substitute | 7 LBD | | | | 821 2823 | Leu⇒Val | CTG⇒GTG | 24 | 23 | normal | normal | | | | Female | Normal | | Pinsky et al; Clin Inv Med, 15: 456, 1992 |
| 0513 | MAIS | Substitute | 7 LBD | * | | | 824 2832 | Gln⇒Lys | CAA⇒AAA | | | | | | | Gynocomastia-normal fertility -related to 514 abnormal Bmax DHT | Male | Normal | pos | Giwereman et al; J Clin Endocrinol & Metab 85: 2253-2259, 2000 |
| 0514 | MAIS | Substitute | 7 LBD | * | | | 824 2832 | Gln⇒Lys | CAA⇒AAA | | | | | | | Gynocomastia-normal fertility -related to 513 abnormal Bmax DHT | Male | Normal | pos | Giwereman et al; J Clin Endocrinol & Metab 85: 2253-2259, 2000 |
| 0537 | CAIS | Substitute | 7 LBD | | | | 827 2841 | Phe⇒Val | TTT⇒GTT | | | | | | | | Female | Normal | | Chavez et al; J Hum Genet. 46: 560-565, 2001 |
| 0522 | CAIS | Substitute | 7 LBD | | | | 830 2850 | Leu⇒Val | CTT⇒GTT | | | | | | | | Female | Normal | | Chavez et al; Clin Genet 59::185-188, 2001 |
| 0213 | CAIS | Substitute | 7 LBD | | | * | 831 2853 | Arg⇒Stop | CGA⇒TGA | | | zero | | | | | Female | Normal | pos | DeBellis et al; Mol Endocrinol, 6: 1909-20, 1992 |

TABLE 5-continued

| Ac-ces-sion # | Phenotype | Mutation type | Exon Domain | Pathogenicity prov-en | CpG hot spot | Amino acid Base | Position Change Amino acid Base | Exon 1 tracts Poly Gln # | Poly Gly # | Androgen Binding Bmax | Kd | k | Ther-mo-labile | Comments | Sex of rearing | External Genitalia | Family history | Reference |
|---|---|---|---|---|---|---|---|---|---|---|---|---|---|---|---|---|---|---|
| 0214 | CAIS | Substitute | 7 LBD | | * | 831 2853 | Arg⇒Stop CGA⇒TGA | | | zero | | | | | Female | Normal | | Tincello et al; J Endocrinol, 132 Suppl, Abstr 87, 1992 |
| 0215 | CAIS | Substitute | 7 LBD | | * | 831 2853 | Arg⇒Stop CGA⇒TGA | | | zero | | | | | Female | Normal | | Ris-Stalpers et al; 74th Endo Soc Meeting, 1992 |
| 0384 | CAIS | Substitute | 7 LBD | | * | 831 2853 | Arg⇒Stop CGA⇒TGA | | | | | | | | Female | Normal | | Giwercman et al; Human Genetics 103: 529-531, 1998 |
| 0465 | CAIS | Substitute | 7 LBD | | * | 831 2853 | Arg⇒Stop CGA⇒TGA | | | | | | | | Female | Normal | | Ahmed et al; J Clin Endocrinol & Metab 85: 658-665, 2000 |
| 0500 | CAIS | Substitute | 7 LBD | | * | 831 2853 | Arg⇒Stop CGA⇒TGA | | | | | | | | Female | Normal | | Choi et al; Arch Gynecol Obstet 263: 201-205, 2000 |
| 0515 | CAIS | Substitute | 7 LBD | | * | 831 2853 | Arg⇒Stop CGA⇒TGA | | | | | | | Hamatoma found in pubertal patient | Female | Normal | | Chen et al; Fertilty & Sterility 74: 182-183, 2000 |
| 0466 | CAIS | Substitute | 7 LBD | | * | 831 2854 | Arg⇒Gln CGA⇒CAA | | | | | | | | Female | Normal | | Ahmed et al; J Clin Endocrinol & Metab 85: 658-665, 2000 |
| 0499 | CAIS | Substitute | 7 LBD | | * | 831 2854 | Arg⇒Gln CGA⇒CAA | | | | | | | | Female | Normal | | Choi et al; Arch Gynecol Obstet 263: 201-205, 2000 |
| 0216 | CAIS | Substitute | 7 LBD | * | * | 831 2854 | Arg⇒Gln CGA⇒CAA | | | v low | | | | | Female | Normal | pos | Brown et al; Mol Endocrinol, 4: 1759-72, 1990 |
| 0217 | CAIS | Substitute | 7 LBD | | * | 831 2854 | Arg⇒Gln CGA⇒CAA | 21 | 19 | zero | | | | Found in two unrelated families | Female | Normal | | McPhaul et al; J Clin Inv, 90: 2097, 1992 |
| 0404 | CAIS | Substitute | 7 LBD | | * | 831 2854 | Arg⇒Gln CGA⇒CAA | | | zero | | | | | Female | Normal | | Yaegashi et al; Tohoku J of Exp Med 187: 263-272, 1999 |
| 0524 | CAIS | Substitute | 7 LBD | | * | 831 2854 | Arg⇒Gln CGA⇒CAA | 26 | 16 | zero | | | | Sertoli cell carcinoma | Female | Normal | | Ko et al. Int. J. Gynocol. Pathol. 20: 196-199, 2001 |
| 0218 | CAIS | Substitute | 7 LBD | * | | 831 2854 | Arg⇒Leu CGA⇒CTA | | | | | | | | Female | Normal | | Shkolny et al; Human Mol Genetics 4: 515-521, 1995 |
| 0307 | CAIS | Substitute | 7 LBD | * | | 831 2854 | Arg⇒Leu CGA⇒CTA | | | zero | | | | | Female | Normal | | Shkolny et al; Human Mol Genetics 4: 515-521, 1995 |
| 0219 | CAIS | Substitute | 7 LBD | | | 834 2863 | Tyr⇒Cys TAC⇒TGC | | | | | | | | Female | Normal | | Wilson et al; J Clin Endocrinol Metab, 75: 1474-8, 1992 |
| 0392 | PAIS | Substitute | 7 LBD | | | 838 2876 | Leu⇒Leu CTC⇒CTT | | | | | | | Hypospadia and cryptorchidism - | Male | Ambiguous | | Nordenskjold et al Urological Res, 27: |

TABLE 5-continued

| Accession # | Phenotype | Mutation type | Exon Domain | Pathogenicity prov-en | CpG | hot spot | Amino acid Base | Position Change Amino acid Base | Exon 1 tracts Poly Gln # | Poly Gly # | Androgen Binding Bmax | Kd | k | Ther-mo-labile | Comments | Sex of rearing | External Genitalia | Family history | Reference |
|---|---|---|---|---|---|---|---|---|---|---|---|---|---|---|---|---|---|---|---|
| 0415 PAIS | Substitute | 7 LBD | | | | | 840 2880 | Arg⇒Ser CGT⇒AGT | | | | | | | silent mutation | Male | Ambiguous | pos | Melo et al; Hum Mutat. 14: 353, 1999 49-55, 1999 |
| 0220 PAIS | Substitute | 7 LBD | * | * | | 840 2880 | Arg⇒Cys CGT⇒TGT | 20 | 16 | normal | high | norm | | | Male | Ambiguous | pos | Beitel et al; J Clin Inv, 94: 546-554 1994 |
| 0221 PAIS | Substitute | 7 LBD | * | * | | 840 2880 | Arg⇒Cys CGT⇒TGT | | | low | high | | * | | Female | | | McPhaul et al; J Clin Inv, 90: 2097, 1992 |
| 0222 PAIS | Substitute | 7 LBD | * | * | | 840 2880 | Arg⇒Cys CGT⇒TGT | | | normal | high | | * | Found in two unrelated individuals. Sibling of 0308 | Female | Ambiguous | pos | Bevan et al; Hum Mol Genet, 5: 265-273, 1996 |
| 0308 PAIS | Substitute | 7 LBD | * | * | | 840 2880 | Arg⇒Cys CGT⇒TGT | | | normal | high | | | Sibling of 0222 | Male | Ambiguous | pos | Bevan et al; Hum Mol Genet, 5: 265-273, 1996 |
| 0387 PAIS | Substitute | 7 LBD | * | * | | 840 2880 | Arg⇒Cys CGT⇒TGT | | | | | | | Transcriptional activity only at high conc of androgen | | | | Georget et al; J Clin Endocrinol & Metab 83: 3597-3603, 1998 |
| 0385 PAIS | Substitute | 7 LBD | * | | | 840 2880 | Arg⇒Gly CGT⇒GGT | | | low | | | | Reduced transactivation | | | | Giwercman et al; Human Genetics 103: 529-531, 1998 |
| 0337 PAIS | Substitute | 7 LBD | * | * | | 840 2881 | Arg⇒His CGT⇒CAT | 19 | | normal | high | high | * | | Female | Ambiguous | pos | Beitel et al; J Clin Inv, 94: 546-554 1994 |
| 0024 PAIS | Substitute | 7 LBD | * | * | | 840 2881 | Arg⇒His CGT⇒CAT | 18 | 24 | normal | high | high | * | | Female | Ambiguous | pos | Beitel et al; J Clin Inv, 94: 546-554 1994 |
| 0025 PAIS | Substitute | 7 LBD | * | * | | 840 2881 | Arg⇒His CGT⇒CAT | | | | high | | | Found in two unrelated families | Female | Ambiguous | pos in 1 fam | Hiort et al; J Clin Endocrinol Metab, 77: 262-266, 1993 |
| 0226 PAIS | Substitute | 7 LBD | * | * | | 840 2881 | Arg⇒His CGT⇒CAT | | | zero | | | | | | | | McPhaul et al; J Clin Inv, 90: 2097, 1992 |
| 0227 PAIS | Substitute | 7 LBD | * | * | | 840 2881 | Arg⇒His CGT⇒CAT | | | normal | normal | | * | In same fam. persons raised as males with ambiguous genitalia | Female | Ambiguous | pos | Imasaki et al; Eur J Endorinol, 130: 569-574, 1994 |
| 0228 PAIS | Substitute | 7 LBD | * | * | | 840 2881 | Arg⇒His CGT⇒CAT | | | low | | | | | Female | | | Lumbroso et al; Eur J Endorinol 130: 327, 1994 |
| 0229 PAIS | Substitute | 7 LBD | * | * | | 840 2881 | Arg⇒His CGT⇒CAT | | | low | | | | | | | | Imai et al; Annals of Clinical Biochem, 32: 482-486, 1995 |
| 0230 PAIS | Substitute | 7 LBD | * | * | | 840 2881 | Arg⇒His CGT⇒CAT | | | | | | | | | | | Ghirri & Brown; Pediatr Res 33: Abstr.95, 1993 |
| 0231 PAIS | Substitute | 7 LBD | * | * | | 840 2881 | Arg⇒His CGT⇒CAT | | | low | high | high | | | | | | Marcelli et al; J Clin Invest 94: 1642-1650, 1994 |
| 0232 PAIS | Substitute | 7 LBD | * | * | | 840 2881 | Arg⇒His CGT⇒CAT | | | normal | high | | * | | Female | Ambiguous | pos | Weidemann et al; Clin Endocrinology 45: 733-739, 1996 |
| 0223 PAIS | Substitute | 7 LBD | * | * | | 840 2881 | Arg⇒His CGT⇒CAT | | | low | high | | | | Female | Ambiguous | | De Bellis et al; J Clin Endcrinol Metab, |

TABLE 5-continued

| Ac-ces-sion # | Phenotype | Mutation type | Exon Domain | Pathogenicity prov-en | CpG hot spot | Position Change Amino acid # Base | Position Change Amino acid Base | Exon 1 tracts Poly Gln # | Exon 1 tracts Poly Gly # | Androgen Binding Bmax | Androgen Binding Kd | Androgen Binding k | Ther-mo-labile | Comments | Sex of rearing | External Genitalia | Family history | Reference |
|---|---|---|---|---|---|---|---|---|---|---|---|---|---|---|---|---|---|---|
| 0233 | PAIS | Substitute | 7 LBD | | | 841 2884 | Ile⇒Ser A_TC⇒_AGC | | | | | | | | Female | Ambiguous | | Hiort et al; Am J Med Genet. 63: 218-222, 1996 |
| 0234 | CAIS | Substitute | 7 LBD | | | 842 2887 | Ile⇒Thr A_TT⇒_ACT | | | | | | | | Female | Normal | pos | Hiort et al; J Clin Endocrinol Metab, 77: 262-266, 1993 |
| 0235 | PAIS | Substitute | 7 LBD | * | | 842 2887 | Ile⇒Thr A_TT⇒_ACT | | | low | high | | * | | Male | Ambiguous | pos | Weidemann et al Clin Endocrinology 45: 733-739, 1996 |
| 0494 | Prostate cancer | Substitute | 7 LBD | | | 846 2898 | Arg⇒Gly A_GA⇒_GGA | | | | | | | Somatic mutation | Male | Normal | | Marcelli et al; Cancer Research 60: 944-949, 2000 |
| 0236 | CAIS | Insertion | 7 LBD | | | 848 2906 | Asn⇒Lys AAT⇒AAAT | | | zero | | | | nt insert causes frame-shift, stop in Codon 879 & loss of AA's | Female | Normal | | Brinkmann et al; J Steroid Biochem Mol Biol 53: 443, 1995 |
| 0467 | CAIS | Insertion | 7 LBD | | | 848 2906 | Asn⇒Lys AAT⇒AAAT | | | zero | | | | nt insert causes frame-shift. | Female | Normal | | Ahmed et al; Clin Endocrinol & Metab 85: 658-665, 2000 |
| 0237 | CAIS | Substitute | 7 LBD | | | 853 2920 | Ser⇒Stop T_CA⇒_TGA | | | zero | | | | | Female | Normal | | Wilson et al; J Clin Endocrinol Metab, 75: 1474-8, 1992 |
| 0238 | CAIS | Substitute | 7 LBD | | | 853 2920 | Ser⇒Stop T_CA⇒_TGA | | | zero | | | | | Female | Normal | | Jakubiczka et al; Human Mutation 9: 57-61, 1997 |
| 0239 | PAIS | Substitute | 7 LBD | | | 854 2923 | Arg⇒Lys A_GA⇒_AAA | | | low | | | * | | Female | Normal | | McPhaul et al; J Clin Inv, 90: 2097, 1992 |
| 0240 | CAIS | Substitute | 7 LBD | | * | 855 2925 | Arg⇒Cys C_GC⇒_TGC | | | zero | | | | | Female | Normal | | DeBellis et al; Mol Endocrinol 6: 1909-20, 1992 |
| 0241 | CAIS | Substitute | 7 LBD | | * | 855 2925 | Arg⇒Cys C_GC⇒_TGC | | | | | | | | Female | Normal | | Tincello et al; J Endocrinol 132 Suppl, Abstr 87, 1992 |
| 0242 | CAIS | Substitute | 7 LBD | | * | 855 2925 | Arg⇒Cys C_GC⇒_TGC | | | zero | | | | | Female | Normal | | McPhaul et al; J Clin Inv, 90: 2097, 1992 |
| 0243 | CAIS | Substitute | 7 LBD | | * | 855 2925 | Arg⇒Cys C_GC⇒_TGC | | | | | | | | Female | Normal | | Loboccaro et al; Pediat Res 33: Abstr 115, 1993 |
| 0244 | CAIS | Substitute | 7 LBD | * | * | 855 2925 | Arg⇒Cys C_GC⇒_TGC | | | low | | | | | Female | Normal | pos | Morono et al; Human Mutation 6: 152-162. 1995 |
| 0245 | CAIS | Substitute | 7 LBD | | * | 855 2925 | Arg⇒Cys C_GC⇒_TGC | | | zero | | | | | Female | Normal | | Sultan et al; J Steroid Biochem & Mol Biol: 40 519, 1993 |
| 0246 | CAIS | Substitute | 7 LBD | | * | 855 2925 | Arg⇒Cys C_GC⇒_TGC | | | | | | | | Female | Normal | | Brinkmann et al; J Steroid Biochem & Mol Biol 53: 443, 1995 |
| 0247 | CAIS | Substitute | 7 | | * | 855 | Arg⇒Cys | | | | | | | | Female | Normal | | Hiort et al; Am J Med 78: 513, 1994 |

TABLE 5-continued

| Ac-ces-sion # | Phenotype | Mutation type | Pathogenicity | | | | Position Change | | | Exon 1 tracts | | Androgen Binding | | | Ther-mo-labile | Comments | Sex of rearing | External Genitalia | Family history | Reference |
|---|---|---|---|---|---|---|---|---|---|---|---|---|---|---|---|---|---|---|---|---|
| | | | Exon Domain | prov-en | CpG hot spot | Amino acid Base | Amino acid | Base | Position Change | Poly Gln # | Poly Gly # | Bmax | Kd | k | | | | | | |
| 0248 | CAIS | Substitute | 7 LBD | | | 855 2925 | | CGC⇒TGC | | | | | | | | | | | | Genet. 63: 218-222, 1996 |
| 0320 | CAIS | Substitute | 7 LBD | | * | 855 2925 | Arg⇒Cys | CGC⇒TGC | | | | v low | high | | | | Female | Normal | pos | Malmgren et al; Clin Genet. 50: 202-205, 1996 |
| 0468 | CAIS | Substitute | 7 LBD | | * | 855 2925 | Arg⇒Cys | CGC⇒TGC | | | | | | | | | Female | Normal | | Komori et al; J Obstetrics & Gynocol. Res. 23: 277-81, 1997 |
| 0469 | CAIS | Substitute | 7 LBD | | * | 855 2925 | Arg⇒Cys | CGC⇒TGC | | | | zero | | | | | Female | Normal | | Ahmed et al; J Clin Endocrinol & Metab 85: 658-665, 2000 |
| 0527 | CAIS | Substitute | 7 LBD | * | * | 855 2925 | Arg⇒Cys | CGC⇒TGC | | | | normal | high | | | | Female | Normal | | Ahmed et al; J Clin Endocrinol & Metab 85: 658-665, 2000 |
| 0528 | PAIS | Substitute | 7 LBD | | * | 855 2925 | Arg⇒Cys | CGC⇒TGC | | | | v low | high | | * | | Male | Ambiguous | | Elhaji et al. 83rd US Endo Soc Meeting, Abstr P2-37, 2001 |
| 0251 | PAIS | Substitute | 7 LBD | | * | 855 2926 | Arg⇒His | CGC⇒CAC | | | | normal | high | | | | | | | Elhaji et al. 83rd US Endo Soc Meeting, Abstr P2-37, 2001 |
| 0252 | PAIS | Substitute | 7 LBD | * | * | 855 2926 | Arg⇒His | CGC⇒CAC | | | | normal | high | | * | Servere hypospadia | Male | Ambiguous | pos | Chang et al; 73rd Endo Soc Meeting, Abstr 28, 1991 |
| 0253 | PAIS | Substitute | 7 LBD | | * | 855 2926 | Arg⇒His | CGC⇒CAC | | | | | | | | | Male | Ambiguous | | Batch et al; Hum Mol Genet, 1: 497, 1992 |
| 0254 | PAIS | Substitute | 7 LBD | * | * | 855 2926 | Arg⇒His | CGC⇒CAC | | | | zero | | | | | Female | Ambiguous | pos | Hiort et al; Am J Med Genet. 63: 218-222, 1996 |
| 0255 | PAIS | Substitute | 7 LBD | | * | 855 2926 | Arg⇒His | CGC⇒CAC | | | | low | high | norm | | | Female | Ambiguous | | Weidemann et al; Clin Endocrinology 45: 733-739, 1996 |
| 0301 | PAIS | Substitute | 7 LBD | | * | 855 2926 | Arg⇒His | CGC⇒CAC | | 14 | | | | | | Brother of 0302 somatic & germ-line muts. in mother | Male | Ambiguous | pos | Marcelli et al; J Clin Invest, 94: 1642-1650, 1994 |
| 0250 | PAIS | Substitute | 7 LBD | | * | 855 2926 | Arg⇒His | CGC⇒CAC | | | | zero | | | | | Female | Ambiguous | | Boehmer et al; Am J Hum Genetics 60: 1003-6, 1997 |
| 0302 | PAIS | Substitute | 7 LBD | * | * | 855 2926 | Arg⇒His | CGC⇒CAC | | 14 | | | | | | Sister of 0301. somatic & germ-line muts. in mother | Female | Ambiguous | pos | Weidemann et al; Clin Endorinology 45: 733-739, 1996 |
| 0249 | PAIS | Substitute | 7 LBD | | * | 855 2926 | Arg⇒His | CGC⇒CAC | | | | low | | | | | Female | Ambiguous | pos | Boehmer et al; Am J Hum Genetics 60: 1003-6, 1997 |
| 0344 | PAIS | Substitute | 7 | | * | 855 | Arg⇒His | | | | | | | | | | Female | Normal | | McPhaul et al; J Clin Invest. 90: 2097, 1992 Melo et al; 80th US |

TABLE 5-continued

| Ac-ces-sion # | Phenotype | Mutation type | Pathogenicity Exon Domain | Pathogenicity prov-en | CpG | hot spot | Position Change Amino acid Base | Position Change Amino acid Base | Exon 1 tracts Poly Gln # | Exon 1 tracts Poly Gly # | Androgen Binding Bmax | Androgen Binding Kd | Androgen Binding k | Ther-mo-labile | Comments | Sex of rearing | External Genitalia | Family history | Reference |
|---|---|---|---|---|---|---|---|---|---|---|---|---|---|---|---|---|---|---|---|
| 0470 | CAIS | Substitute | 7 LBD | | | | 2926 | CGC⇒CAC | | | | | | | | Female | Normal | | Endo Soc Meetings Abstr P2-44, 1998 |
| 0356 | CAIS | Substitute | 7 LBD | | | | 856 2930 | Phe⇒Leu TTC⇒TTG | | | | | | | | Female | Normal | | Ahmed et al; J Clin Endocrinol & Metab 85: 658-665, 2000 |
| 0256 | CAIS | Substitute | 7 LBD | | | | 857 | Tyr⇒Stop TAC⇒ | | | | | | | de novo mutation | Female | Normal | neg | Hiort et al; J Pediatrics 132: 939-943, 1998 |
| 0257 | CAIS | Substitute | 7 LBD | * | | | 863 2950 | Leu⇒Arg CTG⇒CGG | | | | | | | | Female | Normal | | Brown et al; Eur J Pediatr 152: (Suppl 2) S62, 1993 |
| 0471 | CAIS | Substitute | 7 LBD | | | | 864 2952 | Asp⇒Asn GAC⇒AAC | | | low | | | | Transactivation activity increases with horm. concentration | Female | Normal | | Bevan et al; J Steroid Biochem Molec. Biol 61: 19-26, 1997 |
| 0258 | CAIS | Substitute | 7 LBD | * | | | 864 2952 | Asp⇒Asn GAC⇒AAC | | | | | | | | Female | Normal | | Ahmed et al; J Clin Endocrinol & Metab 85: 658-665, 2000 |
| 0472 | CAIS | Substitute | 7 LBD | | | | 864 2953 | Asp⇒Gly GAC⇒GGC | | | zero | | | | | Female | Normal | | DeBellis et al; Mol Endocrinol, 6: 1909-20, 1992 |
| 0486 | CAIS | Substitute | 7 LBD | | | | 864 2953 | Asp⇒Gly GAC⇒GGC | | | zero | | | | | Female | Normal | | Ahmed et al; J Clin Endocrinol & Metab 85: 658-665, 2000 |
| 0560 | CAIS | Substitute | 7 LBD | | | | 865 2955 | Ser⇒Pro TCC⇒CCC | | | | | | | | Female | Normal | | Ahmed et al; J Clin Endocrinol & Metab 85: 658-665, 2000 |
| 0259 | PAIS | Substitute | 7 LBD | | | | 865 2955 | Ser⇒Pro TCC⇒CCC | 21 | | normal | high | | | de novo mut. also Phe68Leu mut-no effect horm binding | Female | Normal | pos | Mongan et al; J Clin endocrinol Metab 87: 1057-1061, 2002 |
| 0345 | PAIS | Substitute | 7 LBD | | | | 866 2958 | Val⇒Leu GTG⇒TTG | 25 | | normal | high | | | | Male | Ambiguous | pos | Saunders et al; Clin Endocrinol 37: 214, 1992 |
| 0260 | PAIS | Substitute | 7 LBD | * | | | 866 2958 | Val⇒Leu GTG⇒TTG | | | normal | high | | | | Male | Ambiguous | pos | Saunders et al; Clin Endocrinol, 37: 214, 1992 |
| 0261 | PAIS | Substitute | 7 LBD | | | | 866 2958 | Val⇒Leu GTG⇒TTG | | | | high | | | | Male | Ambiguous | pos | Kazemi-Esfarjani et al; Mol Endocrinol, 7: 37-46, 1993 |
| 0262 | PAIS | Substitute | 7 LBD | * | | | 866 2958 | Val⇒Leu GTG⇒ | | | zero | | | | | Male | Ambiguous | pos | Hiort et al; J Clin Endocrinol Metab, 77: 262-266, 1993 |
| 0263 | CAIS | Substitute | 7 LBD | * | | * | 866 2958 | Val⇒Met GTG⇒ATG | 20 | 16 | normal | high | | | | Female | Normal | | Merkabi et al; 75th US Endo Soc Meeting Abstr 602, 1993 |
| | | | | | | | | | | | | | | | | | | | Kazemi-Esfarjani et al; Mol Endocrinol, 7: 37-46, 1993 |

TABLE 5-continued

| Ac-ces-sion # | Phenotype | Mutation type | Exon Domain | Pathogenicity proven | CpG hot spot | Amino acid Base | Position Change Amino acid Base | Exon 1 tracts Poly Gln # | Poly Gly # | Androgen Binding Bmax | Kd | k | Ther-mo-labile | Comments | Sex of rearing | External Genitalia | Family history | Reference |
|---|---|---|---|---|---|---|---|---|---|---|---|---|---|---|---|---|---|---|
| 0264 | CAIS | Substitute | 7 LBD | * | | 866 2958 | Val⇒Met GTG⇒ATG | | | normal | high | | | | Female | Normal | | Weidemann et al; J Clin Endocrinology 45: 733-739, 1996 |
| 0265 | CAIS | Substitute | 7 LBD | | * | 866 2958 | Val⇒Met GTG⇒ATG | | | normal | high | | * | | Female | Normal | | Lubahn et al; Proc Natl Acad Sci. 86: 9534, 1989 |
| 0266 | PAIS | Substitute | 7 LBD | | * | 866 2958 | Val⇒Met GTG⇒ATG | | | | | | * | | | | | McPhaul et al; J Clin Inv, 90: 2097, 1992 |
| 0267 | PAIS | Substitute | 7 LBD | | * | 866 2958 | Val⇒Met GTG⇒ATG | | | | high | | * | de novo mutation-mosaic 2 functionally diff AR's | Female | Ambiguous | neg | Hiort et al; J Pediatrics 132: 939-943, 1998 |
| 0373 | Prostate cancer | Substitute | 7 LBD | | * | 866 2958 | Val⇒Met GTG⇒ATG | | | | | | | Somatic mutation | Male | Normal | | Takahashi et al; Cancer Research 55: 1621-1624, 1995 |
| 0473 | CAIS | Substitute | 7 LBD | | * | 866 2958 | Val⇒Met GTG⇒ATG | | | | | | | | Female | Normal | | Ahmed et al; J Clin Endocrinol & Metab 85: 658-665, 2000 |
| 0474 | CAIS | Substitute | 7 LBD | | * | 866 2958 | Val⇒Met GTG⇒ATG | | | zero | | | | | Female | Normal | | Ahmed et al; J Clin Endocrinol & Metab 85: 658-665, 2000 |
| 0475 | CAIS | Substitute | 7 LBD | | * | 866 2958 | Val⇒Met GTG⇒ATG | | | zero | | | | | Female | Normal | | Ahmed et al; J Clin Endocrinol & Metab 85: 658-665, 2000 |
| 0268 | CAIS | Substitute | 7 LBD | | | 866 2959 | Val⇒Glu GTG⇒GAG | | | | | | | | Female | Normal | | McPhaul et al; J Clin Inv, 90: 2097, 1992 |
| 0269 | PAIS | Substitute | 8 LBD | | * | 869 2969 | Ile⇒Met ATT⇒ATG | 26 | | normal | high | | * | Hypospadia | Male | Ambiguous | pos | Bevan et al; Hum mol Genet, 5: 265-273, 1996 |
| 0270 | PAIS | Substitute | 8 LBD | | * | 870 2971 | Ala⇒Val GCG⇒GTG | | | | | | | Found in two unrelated families | Male | Ambiguous | | Hiort et al; Eur J Pediatr, 153: 317, 1994 |
| 0315 | PAIS | Substitute | 8 LBD | | | 870 2971 | Ala⇒Gly GCG⇒GGG | | | | | | | Severe hypospadias | Male | Ambiguous | | Albers et al; J of Pediatrics 131: 388-392, 1997 |
| 0271 | PAIS | Substitute | 8 LBD | | * | 870 2971 | Ala⇒Gly GCG⇒GGG | | | | | | | de novo mutation | Female | Ambiguous | neg | Hiort et al; J Pediatrics 132: 939-943, 1998 |
| 0562 | MAIS | Substitute | 8 LBD | | * | 870 2971 | Ala⇒Gly GCG⇒GGG | | | | | | | bilateral gynecomastia | Male | Normal | | Zenteno et al; Horm Res 57: 90-93, 2002 |
| 0272 | MAIS | Substitute | 8 LBD | | * | 871 2973 | Arg⇒Gly AGA⇒GGA | | 24 | normal | normal | norm | | | Male | Normal | | Shkolny et al; J Clin Endocrinol & Metab 84: 805-810, 1999 |
| 0273 | Prostate cancer | Substitute | 8 LBD | | | 874 2982 | His⇒Tyr CAT⇒TAT | | | | | | | Som mut-stimulated by progesterone & oestrogen | Male | Normal | | Taplin et al; New England J Med 332: 1393-1398, 1995 |
| 0274 | Prostate cancer | Substitute | 8 LBD | | * | 874 2982 | His⇒Tyr CAT⇒TAT | | | | | | | Somatic mutation | Male | Normal | | Tan et al; J of Urology 155: 340A, 1996 |
| 0538 | CAIS | Substitute | 8 LBD | | | 874 2983 | His⇒Arg CAT⇒CGT | | | zero | | | | | Female | Normal | | Chavez et al; J Hum Genet. 46: 560-565, |

TABLE 5-continued

| Acces-sion # | Phenotype | Mutation type | Exon Domain | Pathogenicity proven | CpG hot spot | Amino acid Base | Position Change Amino acid Base | Exon 1 tracts Poly Gln # | Exon 1 tracts Poly Gly # | Androgen Binding Bmax | Androgen Binding Kd | Androgen Binding k | Ther-mo-labile | Comments | Sex of rearing | External Genitalia | Family history | Reference |
|---|---|---|---|---|---|---|---|---|---|---|---|---|---|---|---|---|---|---|
| 0275 | LNCaP mutation | Substitute | 8 LBD | | | 877 2991 | Thr⇒Ala ACT⇒GCT | | | | | | | Altered binding specificity-somatic mutation | Male | Normal | | Veldscholte et al; Biochem Biophys Res Comm, 172: 534, 1990 |
| 0276 | Prostate cancer | Substitute | 8 LBD | | | 877 2991 | Thr⇒Ala ACT⇒GCT | | | | | | | Somatic mutation ⅛ endocrine resistant therapy cases | Male | Normal | | Suzuki et al; J Steroid Biochem Molec Biol 46: 759, 1993 |
| 0277 | Prostate cancer | Substitute | 8 LBD | | | 877 2991 | Thr⇒Ala ACT⇒GCT | | | | | | | 6 out of 24 patients screened-somatic mutation | Male | Normal | | Gaddipati et al; Cancer Res, 54: 2861-2864, 1994 |
| 0278 | Prostate cancer | Substitute | 8 LBD | | | 877 2991 | Thr⇒Ala ACT⇒GCT | | | | | | | 3 out of 22 cases in metastatic tissue-somatic mutation | Male | Normal | | Suzuki et al; Prostate 29: 153-158, 1996 |
| 0279 | Prostate cancer | Substitute | 8 LBD | | | 877 2991 | Thr⇒Ala ACT⇒GCT | | | | | | | Somatic mutation in bone metastesees of Prostate cancer | Male | Normal | | Kleinerman et al; J of Urology 155: 624A, 1996 |
| 0432 | Prostate cancer | Substitute | 8 LBD | | | 877 2991 | Thr⇒Ala ACT⇒GCT | | | | | | | Som mut found in 5 of 16 patients treated with flutamide | Male | Normal | | Taplin et al; Cancer Research 59: 2511-2515 1999 |
| 0280 | Prostate cancer | Substitute | 8 LBD | * | | 877 2992 | Thr⇒Ser ACT⇒AGT | | | | | | | Som mut. in 86% of isolates.Stimulated by estrogen & progest | Male | Normal | | Taplin et al; New England J Med 332: 1393-1398, 1995 |
| 0539 | PAIS | Substitute | 8 LBD | | | 879 2997 | Asp⇒Tyr GAC⇒TAC | | | normal | | | | | Male | Ambiguous | | Chavez et al; J Hum Genet. 46: 560-565, 2001 |
| 0553 | Prostate cancer | Substitute | 8 LBD | | | 879 2998 | Asp⇒Gly GAC⇒GCC | | | | | | | Treated with bicalumatide-somatic mutatation | Male | Normal | | Taplin et al; 37th meeting ASCO 20: Abstr 1738, 2001 |
| 0281 | CAIS | Substitute | 8 LBD | | | 881 3003 | Leu⇒Val CTA⇒GTA | | | | | | | Somatic instability in polyglutamine tract | Female | Normal | pos | Davies et al; Clinical Endocrinology 43: 69-77, 1995 |
| 0282 | CAIS | Substitute | 8 LBD | | | 883 3009 | Lys⇒Stop AAG⇒TAG | | | zero | | | | | Female | Normal | pos | Trifiro et al; Am J Med Genet, 40: 493, 1991 |
| 0283 | MAIS | Substitute | 8 LBD | * | | 886 3018 | Met⇒Val ATG⇒GTG | 23 | 23 | normal | normal | norm | | Oligospermia-50% red. in transactivation | Male | Normal | | Yong et al; 46th Am Soc Hum Genetics meetings Abstr 217, A43, 1996 |
| 0309 | MAIS | Substitute | 8 LBD | * | | 886 3018 | Met⇒Val ATG⇒GTG | 21 | 24 | normal | normal | norm | | Oligospermia-50% red. in transactivation | Male | Normal | | Yong et al; 46th Am Soc Hum Genetics meetings Abstr 217, A43, 1996 |
| 0533 | PAIS | Substitute/Splice | 8 LBD | | * | 888 3026 | Ser⇒Ser AGC⇒AGT | 21 | 24 | v low | normal | | | silent mut-part exon 8 + part of 3' untransl also small amt. wt AR | Male | Ambiguous | | Hellwinkel et al; J Clin Endocrinol & Metab 86: 2569-2575, 2001 |
| 0540 | PAIS | Substitute/Splice | 8 LBD | | * | 888 3026 | Ser⇒Ser AGC⇒AGT | | | normal | | | | | Male | Ambiguous | | Chavez et al; J Hum Genet. 46: 560-565, 2001 |
| 0476 | CAIS | Substitute | 8 | | * | 889 | Val⇒Met | | | low | normal | | | | Female | Normal | | Ahmed et al; J Clin 2001 |

TABLE 5-continued

| Ac-ces-sion # | Phenotype | Mutation type | Pathogenicity | | | | Position Change | | Exon 1 tracts | | Androgen Binding | | | Ther-mo-labile | Comments | Sex of rearing | External Genitalia | Family history | Reference |
|---|---|---|---|---|---|---|---|---|---|---|---|---|---|---|---|---|---|---|---|
| | | | Exon Domain | prov-en | CpG | hot spot | Amino acid Base | Amino acid Position Change Base | Poly Gln # | Poly Gly # | Bmax | Kd | k | | | | | | |
| 0284 CAIS | | Substitute | 8 LBD | | | | 3027 | GTG⇒ATG | | | zero | | | | | Female | Normal | | Endocrinol & Metab 85: 658-665, 2000 |
| 0285 PAIS | | Substitute | 8 LBD | | * | | 889 3027 | Val⇒Met GTG⇒ATG | | | | normal | | | | Female | Normal | | Pinsky et al; Clin Inv Med, 15: 456, 1992 |
| | PAIS | Substitute | 8 LBD | | * | | 889 3027 | Val⇒Met GTG⇒ATG | | | low | | | | | Female | Normal | | De Bellis et al; J Clin Endocrinol Metab, 78: 513, 1994 |
| 0321 PAIS | | Substitute | 8 LBD | | * | | 889 3027 | Val⇒Met GTG⇒ATG | | | | | | | | Female | Normal | | Essawi et al; Disease Markers 13: 99-105, 1997 |
| 0433 Prostate cancer | | Substitute | 8 LBD | | * | | 890 3030 | Asp⇒Asn GAC⇒AAC | | | | | | | Mutation also found in peripheral blood | Male | Normal | | Taplin et al; Cancer Research 59: 2511-2515, 1999 |
| 0389 CAIS | | Substitute | 8 LBD | * | | | 892 3036 | Pro⇒Leu CCG⇒TCG | 26 | | low | high | | | Reduced transactivation | Female | Normal | neg | Peters et al; Mol & Cellular Endocrinol. 148: 47-53, 1999 |
| 0375 CAIS | | Substitute | 8 LBD | | | | 892 3037 | Pro⇒Leu CCG⇒CTG | | | | | | | Mutation found in two siblings | Female | Normal | pos | Knoke et al; Human Mutation 12: 220, 1998 |
| 0413 CAIS | | Substitute | 8 LBD | | | | 892 3037 | Pro⇒Leu CCG⇒CTG | | | | | | | | Female | Normal | | Kanayama et al; Int J Urology 6: 327-330, 1999 |
| 0386 CAIS | | Substitute | 8 LBD | * | | | 895 3046 | Met⇒Thr ATG⇒ACG | | | low | | | | Reduced transactivation | Female | Normal | | Giwercman et al; Human Genetics 103: 529-531, 1998 |
| 0286 CAIS | | Substitute | 8 LBD | | | | 898 3055 | Ile⇒Thr ATC⇒ACC | | | | | | | de novo mutation | Female | Normal | neg | Hiort et al; J Pediatrics 132: 939-943, 1998 |
| 0287 Prostate cancer | | Substitute | 8 LBD | | | | 902 3066 | Gln⇒Arg CAA⇒CGA | | | | | | | Somatic mutation in 37% of isolates in initial cloning | Male | Normal | | Taplin et al; New England J Med 332: 1393-1398, 1995 |
| 0288 PAIS | | Substitute | 8 LBD | | | | 903 3069 | Val⇒Met GTG⇒ATG | 27 | | low | | | | Qualitative binding abnormality | Female | Normal | | McPhaul et al; J Clin Inv, 90: 2097, 1992 |
| 0289 CAIS | | Substitute | 8 LBD | | | | 904 3072 | Pro⇒Ser CCC⇒TCC | | 23 | normal | high | | | | Female | Normal | | Pinsky et al; Clin Inv Med, 15: 456, 1992 |
| 0290 CAIS | | Substitute | 8 LBD | | | | 904 3073 | Pro⇒His CCC⇒CAC | | | zero | | | | | Female | Normal | | McPhaul et al; J Clin Inv, 90: 2097, 1992 |
| 0291 CAIS | | Substitute | 8 LBD | * | | | 907 3081 | Leu⇒Phe CTT⇒TTT | | | low | normal | | | Decreased transactivation activity compared to normal | Female | Normal | | Bevan et al; J Steroid Biochem Molec. Biol 61: 19-26, 1997 |
| 0292 PAIS | | Substitute | 8 LBD | * | | | 909 3087 | Gly⇒Arg GGG⇒AGG | | | | low | | | Also silent G to A mutation in codon 211 | Female | Ambiguous | pos | Choong et al; J Clin Endocrinol Metab, 81: 236-243, 1996 |
| 0374 Prostate cancer | | Substitute | 8 LBD | | | | 909 3088 | Gly⇒Glu GGG⇒GAG | | | | | | | Somatic mutation | Male | Normal | | Takahashi et al; Cancer Research 55: 1621-1624, 1995 |
| 0327 Prostate cancer | | Substitute | 8 LBD | | | | 910 3091 | Lys⇒Arg AAA⇒AGA | | | | | | | Somatic mutation | Male | Normal | | Watanabe et al; Jpn J Clin Oncol 27: 389-393, |

TABLE 5-continued

| Acces-sion # | Phenotype | Mutation type | Pathogenicity Exon Domain | Pathogenicity prov-en | CpG hot spot | Position Change Amino acid Base | Position Change Amino Base | Position Change Amino acid Change | Exon 1 tracts Poly Gln # | Exon 1 tracts Poly Gly # | Androgen Binding Bmax | Androgen Binding Kd | Androgen Binding k | Ther-mo-labile | Comments | Sex of rearing | External Genitalia | Family history | Reference |
|---|---|---|---|---|---|---|---|---|---|---|---|---|---|---|---|---|---|---|---|
| 0430 | PAIS | Substitute | 8 LBD | | | 911 3093 | | Val⇒Leu GTC⇒CTC | 19 | | | | | | Servere oligozoospermia | Male | Ambiguous | | Knoke et al; Andrologia 31: 199-201, 1999 |
| 0293 | PAIS | Substitute | 8 LBD | | | 913 3099 | | Pro⇒Ser CCC⇒TCC | | | | | | | | | | | Ghirri and Brown; Paed Res, 33(5) Suppl, Abstr 95, 1993 |
| 0318 | CAIS | Substitute | 8 LBD | * | | 916 3110 | | Phe⇒Leu TTC⇒TTG | | | low | high | | * | | Female | Normal | | Radnayr et al; J of Urology 158: 1553-1556, 1997 |
| 0477 | CAIS | Substitute | 8 LBD | | | 917 3112 | | His⇒Arg CAC⇒CGC | | | | | | | | Female | Normal | | Ahmed et al; J Clin Endocrinol & Metab 85: 658-665, 2000 |
| 0303 | Prostate cancer | Substitute | 8 LBD | * | | 919 3118 | | Gln⇒Arg CAG⇒CGG | | | | | | | Somatic mutation | Male | Normal | | Nazareth et al; 79th US Endo Soc Meetings Abstr. P2-489, 1997 |
| 0294 | CAIS | Splice | exon1 intron1 | | | | | ⇒ gta⇒gtta | 24 | 23 | | | | | Insertion at +3 position of donor splice site | Female | Normal | | Trifiro et al; Eur J Hum Genetics 5: 50-58, 1997 |
| 0304 | CAIS | Splice | exon2 intron2 | | | | | ⇒ ctg⇒cta | | | | | | | Substitution at +1 pos of donor splice site-lacks exon 2 | Female | Normal | neg | Hellwinkel et al; J Steroid Biochem & Mol Biol 68: 1-9, 1999 |
| 0479 | CAIS | Splice | exon2 intron2 | | | | | ⇒ ggt⇒gt | | | zero | | | | | Female | Normal | | Ahmed et al; J Clin Endocrinol & Metab 85: 658-665, 2000 |
| 0480 | CAIS | Splice | exon2 intron2 | | | | | ⇒ ggt⇒gtt | | | | | | | | Female | Normal | | Ahmed et al; J Clin Endocrinol & Metab 85: 658-665, 2000 |
| 0295 | CAIS | Splice | exon3 intron3 | | | | | ⇒ ggt⇒g_t | | | normal | normal | | | Substitution at +1 position of donor splice site | Female | Normal | | Evans et al; J Endocrinol 129 Suppl, Abstr 65, 1991 |
| 0478 | CAIS | Splice | exon3 intron3 | | | | | ⇒ ggt⇒gat | | | zero | | | | Substitution at +1 position of donor splice site | Female | Normal | | Ahmed et al; J Clin Endocrinol & Metab 85: 658-665, 2000 |
| 0296 | CAIS | Splice | exon4 intron4 | | | | | ⇒ ggt⇒gtt | | | zero | | | | +1 pos of donor site. Splice site activated & del of aa's 683-723 | Female | Normal | | Ris-Stalpers et al; Proc Natl AcadSci 87: 7866-70, 1990 |
| 0297 | CAIS | Splice | exon6 intron6 | | | | | ⇒ gta⇒tta | 21 | | | normal | | | Substitution at +3 position of donor splice site | Female | Normal | pos | Pinsky et al; Eur J Hum Genetics 5: 50-58, 1997 |
| 0503 | PAIS | Splice | exon6 intron6 | | | | | ⇒ taa⇒tat | | | low | | | | Subst. at +5 position of donor splice site, stop at +79 bases | Female | Ambiguous | | Sammarco et al; J Clin Endocrinol & Metab 85: 3256-3261, 2000 |
| 0541 | CAIS | Splice | exon6 intron6 | | | | | aag⇒aac ⇒ | | | zero | | | | Sust. at +6 position of donor splice site. | Female | Normal | | Chavez et al; J Hum Genet 46: 560-565, 2001 |
| 0298 | CAIS | Splice | exon7 | | | | | ⇒ | | | zero | | | | Subst. at +1 pos of | Female | Normal | pos | Lim et al; Mol & Cell |

TABLE 5-continued

| Accession # | Phenotype | Mutation type | Exon Domain | Pathogenicity prov-en | CpG hot spot | Position Change Amino acid Base | Amino acid Base | Exon 1 tracts Poly Gln # | Exon 1 tracts Poly Gly # | Androgen Binding Bmax | Androgen Binding Kd | Androgen Binding k | Ther-mo-labile | Comments | Sex of rearing | External Genitalia | Family history | Reference |
|---|---|---|---|---|---|---|---|---|---|---|---|---|---|---|---|---|---|---|
| 0502 | CAIS | Splice | intron7 | | | | tgt⇒tat | | | | | | | donor splice, -exon7, stop +10 aa exon 8 | | | | Endocrinology 131: 205-210, 1997 |
| | CAIS | Splice | exon7 intron7 | | | | ⇑ tgt⇒tat | | | | | | | Sustitution at +1 position of donor splice site | Female | Normal | | Choi et al; Arch Gynecol Obstet 263: 201-205, 200 |
| 0299 | PAIS | Splice | intron2/ exon3 | | | | ⇑ gtt⇒gat | | | | | | | Subst. at −11 pos of acceptor site. 2 transc; 1, -exon3, 1, +69 nt. | Male | Normal | | Bruggenwirth et al; Am J Hum Genet 61: 1067-1077, 1997 |
| 0317 | Breast Cancer | Splice | | | | | ⇑ ⇑ | | | | | | | -exon 3: higher express. of mut. var in 7/31breast cancer | Female | Normal | | Zhu et al; Intl J of Cancer 72: 574-580, 1997 |
| 0351 | CAIS | Substitute | intron2 | | | | gt⇒at ⇑ ⇑ | | | | | | | | Female | Normal | | Hiort et al: J Pediatrics 132: 939-943, 1998 |
| 0088 | PAIS | Deletion | intron2 | | | | | | | | normal | normal | | | 6 kb del at −18 pos of acceptor site 2 transcr: 1 wt, 1 minus exon 3 | Male | Ambiguous | pos | Ris-Stalpers et al; Am J Hum Genet 54: 609, 1994 |
| 0312 | Prostate Cancer | Substitute | 5' UTR | | | | ⇑ agc⇒atc | | | | | | | +2 pos from transcription initiation site AR-TIS II | Male | Normal | | Crociotto et al; J of Urology 158: 1599-1601, 1997 |
| 0313 | Prostate Cancer | Substitute | 5' UTR | | | | ⇑ gcc⇒gac | | | | | | | +214 pos from transcription initiation site AR-TIS II | Male | Normal | pos | Crociotto et al; J of Urology 158: 1599-1601, 1997 |
| 0323 | Prostate Cancer | | 3' UTR | | | | ⇑ ⇑ | | | | | | | Som mut. polymorph seq 2820-36 dwnstrm to transl. init. site | Male | Normal | | Paz et al; European Urology 31: 209-215, 1997 |

Other advantages and characteristics will become apparent from the examples below pertaining to:

Example 1: Inhibition of the protein PML-RARα associated with acute promyelocytic leukemia (APL).
Example 2: Inhibition of the tumoral angiogenesis induced by VEGF.
Example 3: Inhibition of the hypoxic response induced by HIF1α.
Example 4: Inhibition of the wild or mutant forms of the androgen receptors in prostate carcinoma cells.
Example 5: Inhibition of the wild or mutant forms of the protein p53.
Example 6: Inhibition of the viral protein E6.
Example 7: Use of DNA/RNA hybrids to inhibit the expression of various proteins.
Example 8: In vivo administration of siRNA via different routes.

EXAMPLE 1

Inhibition of the Protein PML-RARα Associated with Acute Promyelocytic Leukemia (APL)

I—Introduction

Acute promyelocytic leukemia (APL) is due to the translocation t(15;17) on chromosome 15. In patients afflicted with APL, the receptor of retinoic acid (RARα) is fused to the protein PML (promyelocytic leukemia protein) thereby generating the fusion protein PML-RARα. Five fusion proteins bringing RARα into play have been identified to date. All of these leukemia types implicate the RARα receptor and are clinically similar, which suggests that the rupture of the transduction pathway of retinoic acid is crucial in the pathogenesis of APL leukemia.

The fusion protein PML-RARα retained the binding domains of the DNA and retinoic acid of the RARα. It has been shown that the fusion protein PML-RARα represses the expression of the target genes of retinoic acid and thereby also blocks the differentiation of the promyelocytic cells. Only the administration of pharmacological doses of retinoic acid remove transcriptional repression exerted by PML-RARα and restore cellular differentiation. Moreover, the protein portion PML of the fusion protein could also intervene in the mechanism of the blocking of the transduction pathway by retinoic acid. To the extent that PML functions as a growth inhibitor and an apoptotic agent and that it is required for the expression of certain genes induced by retinoic acid, the dominant negative effect of PML-RARα on PML could allow cells to acquire a growth capacity, a resistance to apoptosis and a termination of differentiation.

Cellular biology studies of PML have shown that this protein possesses a particular localization in the nucleus, in structures called nuclear bodies. It appears that these structures are in direct relation with the anti-oncogene role of PML. In malignant APL cells, the protein PML-RARα induces, by heterodimerization with PML, the delocalization of PML from the nuclear bodies to the micropunctuated structures that could correspond to PML-RARα anchorage sites on the chromatin. This delocalization could block the pro-apoptotic function of PML and its role in myeloid differentiation. Multiple research teams have shown that combined treatment with retinoic acid and $AS_2O_3$ on cell lines that express the fusion protein PML-RARα enable the degradation of the fusion proteins at the same time as a relocalization of PML on the nuclear bodies. This reorganization of the nuclear bodies restores the functions of PML and contributes to the restoration of differentiation.

Finally, the chimera protein PML-RARα would thus have a double dominant negative effect on RARα and on PML enabling the cells to escape from apoptosis and blocking the differentiation of the thereby transformed promyelocytes.

More than 98% of the patients suffering from APL leukemia present the translocation t(15;17) (q22;q21) which leads to the formation of fused genes PML-RARAα and RARα-PML. There exist two subtypes of fusion proteins PML-RARα: the S (short) fusions and the L (long) fusions). The long form of the fusion protein PML-RARα corresponding to a protein of 955 amino acids representing the predominantly expressed form, and thus was taken as model in this study (Tables 2, 3 and 5). This protein comprises amino acids 1 to 552 of the protein PML fused with amino acids 59 to 462 of the α receptor of retinoic acid (RARα).

II—Preparation and Administration of the Oligonucleotides

Complementary RNA oligonucleotides corresponding to the sequence of the junction of the gene of the fusion protein, i.e., 10 nucleotides of the PML gene and 10 nucleotides of the RARα gene, were synthesized with addition of two deoxythymidines at 3' (FIG. 1). These oligonucleotides were hybridized and the production of the double-strand oligonucleotide was verified on acrylamide gel.

The sequences of the PML-RAR and control siRNAs used (5'-3') are presented below:
Control:

```
FW:
[CAUGUCAUGUGUCACAUCUC]RNA[TT]DNA      (SEQ ID NO.3)

REV:
[GAGAUGUGACACAUGACAUG]RNA[TT]DNA      (SEQ ID NO.4)

PR:
Sense:
[GGGGAGGCAGCCAUUGAGAC]RNA[TT]DNA      (SEQ ID NO.5)

Antisense:
[GUCUCAAUGGCUGCCUCCCC]RNA[TT]DNA      (SEQ ID NO.6)
```

III—Results

NIH3T3 fibroblasts were cotransfected with lipofectamine by an expression vector of the protein PML-RARα (100 ng) and by 500 ng of control siRNA (C) or siRNA directed against PML-RARα (PR). 48 h after transfection, a Western blot (FIG. 1B) was performed on the total cell extracts using an antibody which recognized the protein RARα, whole or in fusion protein form.

FIG. 1B shows that the transfection of siRNA PR very strongly inhibits the expression of fusion protein PML-RARα compared to the cells transfected with the control siRNA (C) without modifying the expression of the protein RARα.

EXAMPLE 2

Inhibition of Tumoral Angiogenesis by VEGF

I—Introduction

VEGF (vascular endothelial growth factor) is one of the most powerful angiogenic factors identified. These factors are overexpressed in numerous situations of pathological hypervascularization and notably in tumoral development. The inhibition of this angiogenesis enables blocking of tumor growth. The method has the goal of inhibiting tumoral angiogenesis by blocking the expression of one of these angiogenic factors, and as seen in this example, that of VEGF by the tumor cells.

II—Preparation and Administration of the Oligonucleotides

Two RNA oligonucleotides, complementary of a region of the coding sequence of human VEGF, conserved in the rat and the mice, were synthesized. Two deoxynucleotides (TT) were added at 3':

```
Sequence of the RNAi VEGF:
5'[AUGUGAAUGCAGACCAAAGAA]RNA-TT[DNA]    (SEQ ID NO.7)

5'[UUCUUUGGUCUGCAUUCACAU]RNA-TT[DNA]    (SEQ ID NO.8)

Sequence of the control RNAi:
5'[CAUGUCAUGUGUCACAUCUC]RNA-TT[DNA]     (SEQ ID NO.9)

5'[GAGAUGUGACACAUGACAUg]RNA-TT[DNA]     (SEQ ID NO.10)
```

These oligonucleotides or the control oligonucleotides, whose sequence presents no homology with the sequences stored in the data banks, were hybridized and transfected using the Polyfect kit (Qiagen) in the cells of a rat fibrosarcoma (cJ4) and in human cells of the prostate carcinoma LNCaP.

Figure 2:
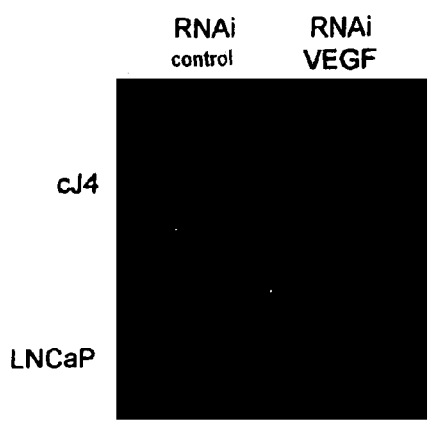
FIG. 2A to FIG. 2E pertain to the inhibition of the expression of VEGF by siRNA directed against this protein and the consequences of this inhibition.
Figure 2:
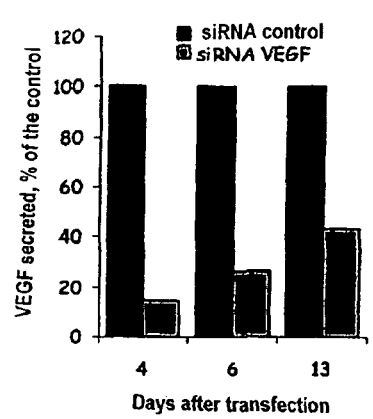
Figure 2:
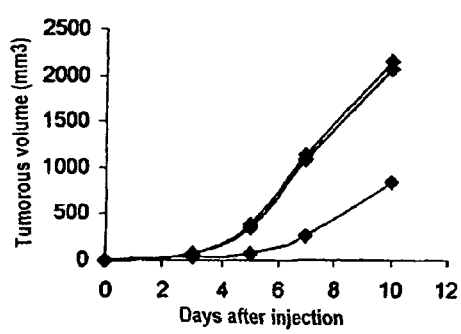
Figure 2:
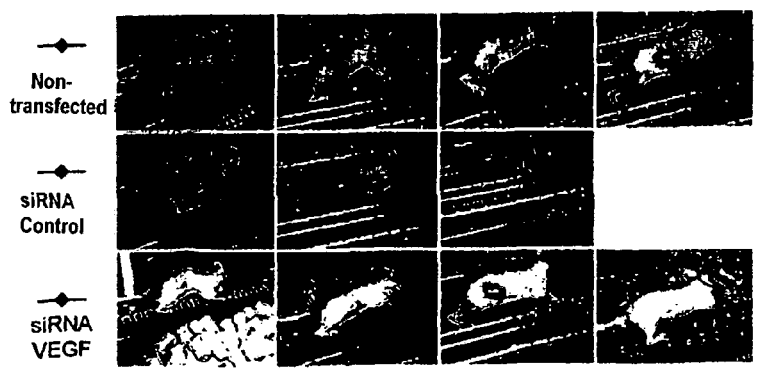
Figure 2:
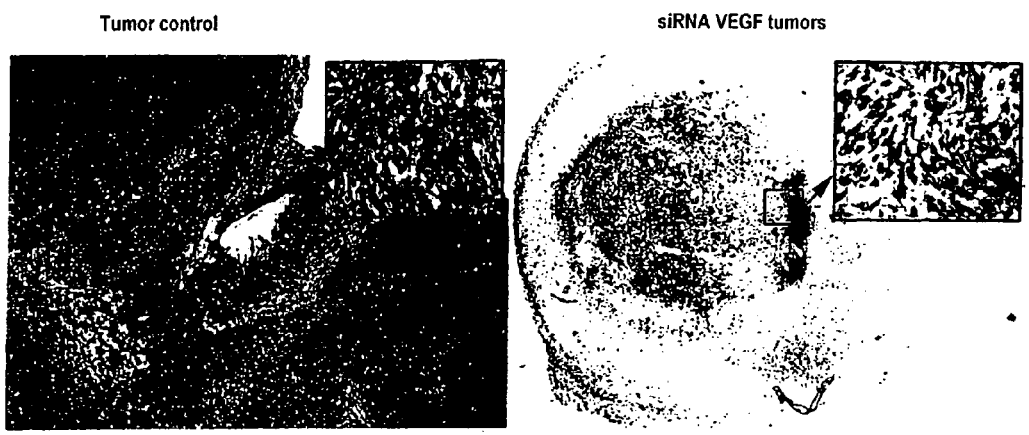

III—Results 48 h after transfection, an indirect immunofluorescence was performed to detect the expression of the protein in the cells. FIG. 2A shows a massive inhibition of the expression of VEGF.

In order to quantify this effect, quantitative determination of the VEGF in the transfected CJ4 cells in parallel with the control RNAi or with the RNAi VEGF was performed with ELISA (quantikine, R&D). The cells were incubated for 48 h prior to the quantitative determination in a medium containing 1% serum. The determination was performed 4 days and 6 days after transfection. Under these conditions, FIG. 2B shows an inhibition of the secretion of VEGF of 85% at 4 days and of 75% at 6 days and of 60% at 13 days in the cells transfected with the RNAi VEGF compared to the cells transfected with the control RNAi (FIG. 2B).

The effect of the inhibition of VEGF on the tumor cells was tested in vivo: 3 days after transfection, three groups of 4 female nude mice aged 4 weeks were injected subcutaneously at the rate of one million cells per mouse: the first group was injected with nontransfected cells, the second group was injected with cells transfected by the control RNAi, the third group was injected with cells transfected with RNAi VEGF. No selection of the transfected cells was performed before the injection.

Tumor growth was monitored by measuring the volume of the tumors at regular intervals (FIG. 2C).

FIGS. 2C and 2D do not show any significant difference between the sizes of the tumors in groups A and B. A very large reduction in the tumor volume was seen in group C. The appearance of the tumors, much whiter in group C (FIG. 2D), manifested a pronounced decrease in the tumoral vascularization. After sacrifice of the animals on day 12 after the injection, the tumors were dissected, fixed and immunodetection of VEGF was performed on sections of these tumors. There was seen a very strong reduction in the expression of VEGF in the tumors of group C compared to that of group B (FIG. 2E).

Figure 4:
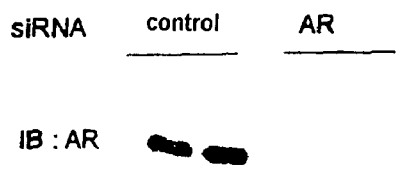
FIG. 4A to FIG. 4F show the inhibition by siRNA specific of the expression of the androgen receptor in the cells and functional consequences of these inhibitions.
Figure 4:
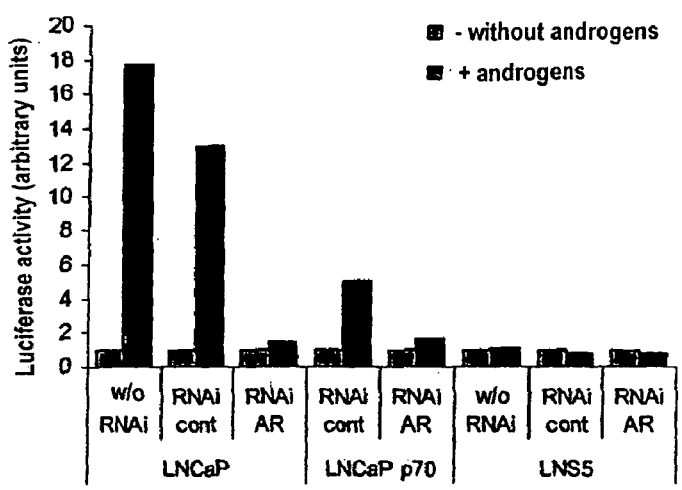
Figure 4:
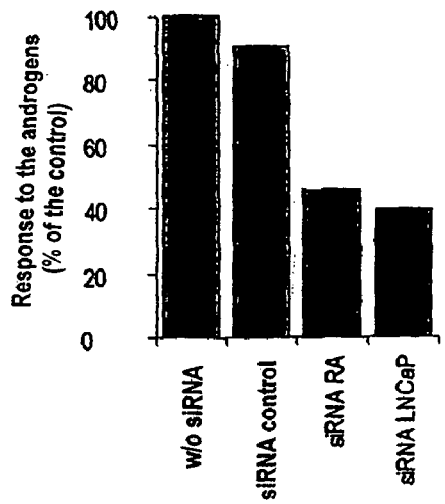
Figure 4:
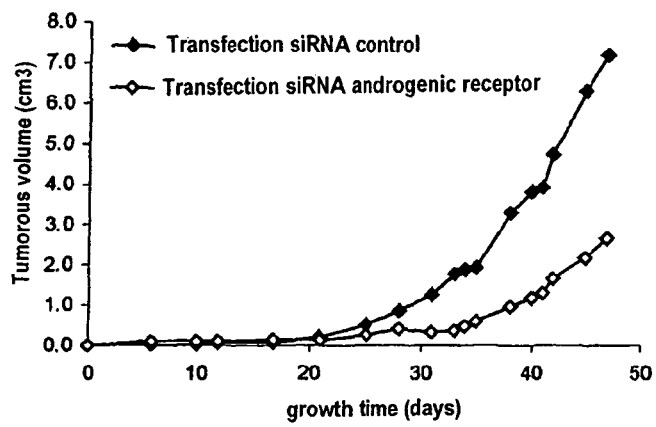
Figure 4:
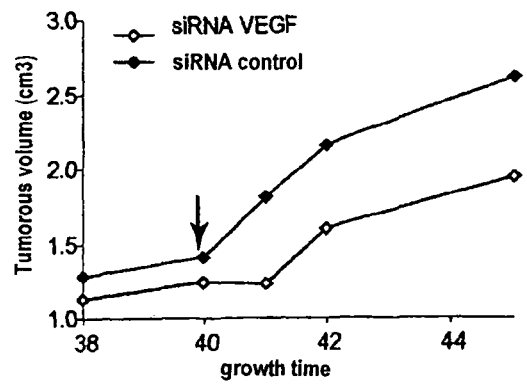
Figure 4:
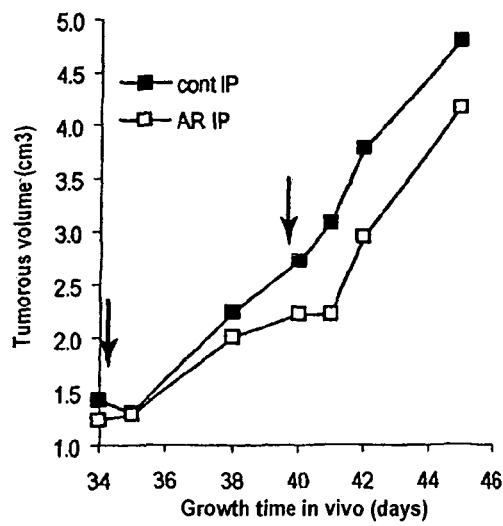

In another experiment, tumors were induced in male nude mice by injection of prostate carcinoma cells LNCaP. 40 days after injection, the volume of the tumors having reached 1 to 1.5 cm$^3$, the mice were divided into two groups. The first group (4 mice) received an intravenous injection in the tail vein of 2 micrograms of control siRNA in 100 µl of PBS. The second group received an equivalent dose of siRNA VEGF under the same conditions. It was observed that the siRNA VEGF but not the control siRNA induced a transitory suspension in tumor growth (FIG. 4D).

EXAMPLE 3

Inhibition of the Hypoxic Reaction

I—Introduction

Certain tumors are capable of developing under strongly anoxic conditions. This is seen very frequently in tumors of regions that are very poorly vascularized. This weak sensitivity to hypoxia has two consequences: on the one hand, an antiangiogenic treatment has little chance of being effective on these tumors or these tumor subpopulations. On the other end, this weak vascularization makes it difficult to deliver the therapeutic molecules. The transcription factor Hif1α regulates the activity of more than 100 genes enabling the hypoxic response. The inhibition of this transcription factor in hypoxic tumors has the goal of blocking their growth.

II—Preparation of the oligonucleotides

```
RNAi Hif1α
5'[CAUGUGACCAUGAGGAAAUGA]RNA-TT[DNA]    (SEQ ID NO.11)

5'[UCAUUUCCUCAUGGUCACAUG]RNA-TT[DNA]    (SEQ ID NO.12)

Control RNAi
5'[GAUAGCAAUGACGAAUGCGUA]RNA-TT[DNA]    (SEQ ID NO.13)

5'[UACGCAUUCGUCAUUGCUAUC]RNA-TT[DNA]    (SEQ ID NO.14)
```

III—Results

The VEGF promoter contains a response element to the transcription factor Hif1α. In order to test in vitro the effect of an RNAi directed against Hif1α, we transfected cJ4 cells with a reporter vector VEGF-luciferase, alone or in combination with an RNAi Hif1α or control.

24 h after transfection, the cells were incubated for 18 h in medium without serum, with the addition in some cases of cobalt chloride 100 µM in order to produce hypoxic conditions; the luciferase activity was then measured.

Figure 3:
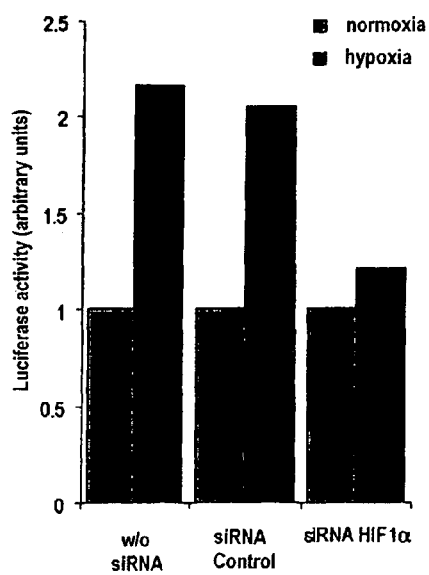
FIG. 3 shows the effect of inhibition by a siRNA specific of the expression of a transcription factor, HIF1α, on the transcriptional response to hypoxia. It also shows the measurement of the activity of a reporter VEGF luciferase in response to hypoxia in CJ4 cells that are not transfected, by the control siRNA or by the siRNA directed against HIF1α.

FIG. 3 shows that a complete inhibition of the induction of the response of the promoter VEGF to hypoxia was observed when the cells were transfected with RNAi Hif1α but not with the control RNAi.

EXAMPLE 4

Inhibition of the Wild or Mutant Forms of the Androgen Receptors in Prostate Carcinomas I—introduction The prostate carcinomas are the second cause of cancer mortality for men in the industrialized countries. They are the cause of more than 9500 deaths per year in France. The prostatic epithelial cells are dependent on androgens for their growth. Prostatic carcinomas are initially androgen dependent. Chemical castration thus initially can block the growth of the carcinoma. However, in all cases, these carcinomas become androgen independent and their prognosis becomes very negative. This androgen independence—depending on the individuals—is often due to a mutation of the receptor (conferring on it, for example, a response to estrogens or to glucocorticoids) or to an amplification of the receptor.

II—Preparation of the Oligonucleotides

Two RNA oligonucleotides complementary to a region of the coding sequence of the nonmutated human androgen receptor (AR) were synthesized. Two deoxynucleotides (TT)

were added at 3'. In other experiments, siRNAs named LNCaP and specifically recognizing the mutation of the androgen receptor (T877A) in the cells of human prostate carcinoma LNCaP, were used.

```
AR:
5'[GACUCAGCUGCCCCAUCCACG]RNA-TT[DNA]    (SEQ ID NO.15)

5'[CGUGGAUGGGGCAGCUGAGUC]RNA-TT[DNA]    (SEQ ID NO.16)

Control:
5'[GAUAGCAAUGACGAAUGCGUA]RNA-TT[DNA]    (SEQ ID NO.17)

5'[UACGCAUUCGUCAUUGCUAUC]RNA-TT[DNA]    (SEQ ID NO.18)

LNCap:
5'[GCAUCAGUUCGCUUUUGAC]RNA-TT[DNA]      (SEQ ID NO.19)

5'[GUCAAAAGCGAACUGAUGC]RNA-TT[DNA]      (SEQ ID NO.20)
```

Multiple subclones of the human prostate carcinoma line LNCaP were used in this study. The original line, LNCaP, is androgen dependent. The cells LN70, obtained by repeated passages of the line LNCaP in vitro have a diminution in their response to androgens. The clone LNS5, obtained after passage of the animals in an animal, is androgen resistant.

III—Results

The LNCaP cells were transfected in vitro with siRNA AR or control siRNAs using the transfection agent Polyfect (Qiagen). 48 h after transfection, the cells were detached from their support. Half of the cells were used for performing a Western blot detection of the androgen receptor; the other half were put back in culture. The androgen receptor (band at 110 kDa) was no longer detectable by Western blot in the cells transfected by siRNA AR (FIG. 4A). The cells transfected by siRNA and put back in culture were found to be incapable of continuing their growth, to the opposite of the cells transfected by the control siRNA.

The level of response to the androgens was measured by transfecting different cellular clones of the lone LNCaP with a reporter vector placing the coding sequence of luciferase downstream of a minimal promoter flanked by 4 repetitions of the androgen response element (4×ARE). After transfection, the cells were incubated for 18 h in the absence of serum and in the presence or absence of a metabolically stable analogue of dihydrotesterone, R1881 (NEN). The ratio of the luciferase activities under these two conditions makes it possible to measure the level of response to the androgens of the reporter vector.

We measured the effect of the cotransfection in the control RNAi or RNAi AR cells on the response to the androgens of the different clones of the line LNCaP.

FIG. 4B shows a complete inhibition of the response to the androgens in the two androgen-sensitive clones: LNCaP and LNCaP p70. This method does not permit measurement of the response of the androgen-resistant clone LNS5 to the treatment by RNAi AR.

The androgen receptor present in the line LNCAP carries a mutation. We used two different siRNAs to inhibit its synthesis, the previously used siRNA AR and siRNA LNCaP specifically recognizing the mutation LNCaP. The response to the androgens was measured as in experiment 4B (FIG. 4C).

In order to study the effect of the inhibition of the expression of the androgen receptor on tumor growth in vivo of the prostate carcinoma cells, carcinoma cells LNCaP, transfected by a control siRNA (group A) or siRNA AR (group B) were injected subcutaneously in male nude mice. Tumor growth was monitored at regular intervals. It was seen that the tumors of the group B animals started growing later than those of group A and that the volume of the tumors of group B on the 48th day was markedly smaller than that of the tumors of group A (FIG. 4D).

In another experiment, LNCaP cells were injected in male nude mice. When, on the 34$^{th}$ day, the tumors had reached a volume comprised between 1.2 and 1.5 cm$^3$, the mice received via the intraperitoneal route an injection of 2 µg of control siRNA or siRNA AR in 100 µl of PBS. This injection was repeated on the 40 day. It was seen that the administration of siRNA AR leads to a slowing down of the tumor growth (FIG. 4E).

EXAMPLE 5

Inhibition of the Wild or Mutant Forms of the Protein p53

I—Preparation of the Oligonucleotides

The three siRNAs whose sequences are presented below were prepared, one directed against the wild form of p3 and the other directed against the mutated form expressed in a patient which resulted in the establishment of a line.

This mutation corresponds to one of the three observed most frequently in human tumors:

```
wild p53:
Sense:
[GCAUGAACCGGAGGCCCAU]RNA[TT]DNA         (SEQ ID NO.21)

Anti:
[AUGGGCCUCCGGUUCAUGC]RNA[TT]DNA         (SEQ ID NO.22)

p53 MT1 (r248w):
Sense:
[GCAUGAACUGGAGGCCCAU]RNA[TT]DNA         (SEQ ID NO.23)

Anti:
[AUGGGCCUCCAGUUCAUGC]RNA[TT]DNA         (SEQ ID NO.24)

p53 MT2 (r248w):
Sense:
[UCAUGAACUGGAGGCCCAU]RNA[TT]DNA         (SEQ ID NO.25)

Anti:
[AUGGGCCUCCAGUUUCAUGA]RNA[TT]DNA        (SEQ ID NO.26)
```

The underlined nucleotides in the wild p53 are those that mutated in the mutant form and which are in italics in the sequences of the mutated form of mutated p53 (p53 MT1 and MT2). The bases in bold above are mutations which were introduced in order to augment the specificity.

II—Results

As shown in FIG. 5B, the H1299-NCI cells, which do not express p53, were transfected (using lipofectamine) by expression vectors (400 ng) of wild p53 (WT) or mutated p53 (MT). siRNAs (in increasing doses: 0, 125 ng, 250 ng, 500 ng and 1000 ng) directed against the wild form (WT), the mutated form (MT1 and MT2) or an irrelevant siRNA (C) were transfected at the same time. The cells were collected 24 hours later and analyzed by Western blot with an antibody directed against p53.

As shown in FIG. 5C, the H1299-NCI cells, which did not express p53, were transfected (using lipofectamine) by expression vectors (400 ng) of wild p53 (WT), mutated p53 (MT) or a mixture of the two (WT+MT) as indicated. siRNAs (400 ng) directed against the wild form (WT), the mutated form (MT1) or an irrelevant siRNA (C) were transfected at the same time. The cells were collected 24 hours later and analyzed by Western blot (ib: immunoblot) with cellular actin (Sigma) to monitor the amount of proteins used in the test.

As shown in FIG. 5D, U2OS cells (human osteosarcoma expressing a wild form of p53) were transfected in a stable manner either by a vector expressing a mutant form of p53 (R248W) or by the corresponding empty vector (pCDNA3). These lines were transfected by the indicated siRNAs and the expression of the indicated proteins was detected by Western blot.

In all cases, the siRNA directed against the mutated form of the protein inhibited the mutated form and the siRNA directed against the wild form inhibited the wild form. Furthermore, there was no crossed reaction because the siRNA directed against the wild form had no effect on the mutated form and vice versa. It should be noted that the expression of the mutant stabilizes the wild protein when it is co-expressed. Consequently, the inhibition of the mutant through its indirect effect brings the wild form to its base level without there being any inhibition of the expression of the protein.

As shown in FIG. 5E, the cells used in FIG. 5D were transfected by the indicated siRNAs. The cells were then subjected to a genotoxic stress by treatment with doxorubicin (200 ng/ml) for 24 h. FIG. 5E shows the analysis of the cell cycle of these cells by incorporation of propidium iodine and FACS analysis. The cells not transfected with the mutant form and thus only expressing the wild form (PCDNA cells) exhibited a high percentage of stopping at G1 in the presence of doxorubicin. The treatment of these cells with wild siRNA, diminishing the wild p53, reduced this stopping at G1. The cells expressing the mutated and wild form (R248W) stopped very little at G1 in the presence of doxorubicin, showing that the mutated form inhibits the activity of the wild form. When these cells were treated with siRNA MT1, they recovered a normal capacity (to compare with the untreated PCDNA controls) of stopping at G1, showing the restoration of the wild p53 activity in these cells.

Figure 5:
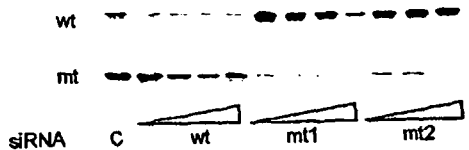
FIGS. 5 F, G, H and I represent the inhibition of the expression of a mutant form of p53 in the cells of a patient with Li-Fraumeni cancer syndrome at the level of the mRNA (5G) and the expression of the protein by immunoblot (GF) or in indirect immunofluorescence (5H) and the consequences on the resistance of these cells to genotoxic stress.
Figure 5:
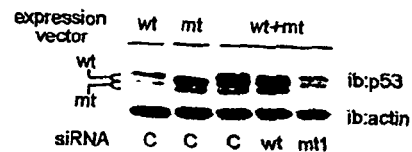
Figure 5:
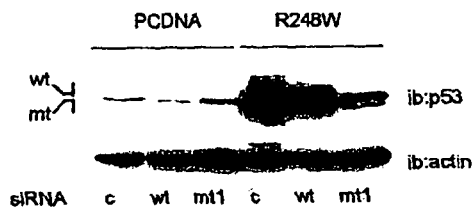
Figure 5:
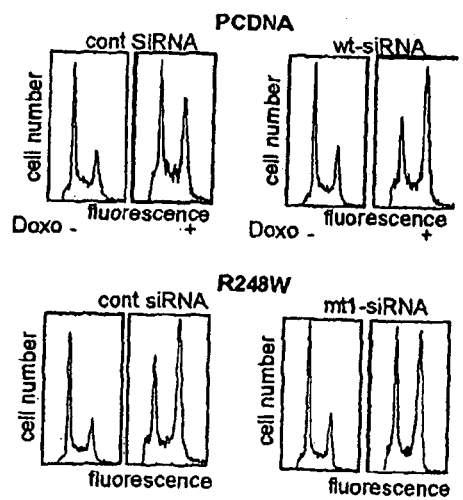
Figure 5:
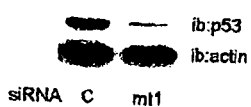
Figure 5:
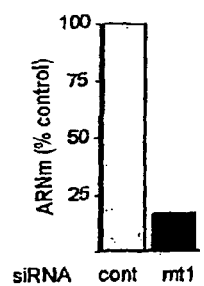
Figure 5:
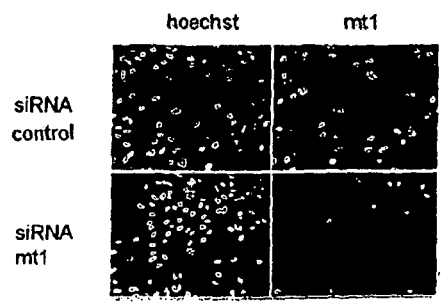
Figure 5:
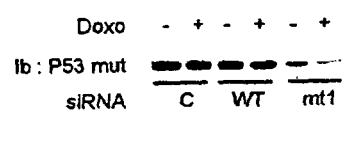
Figure 5:
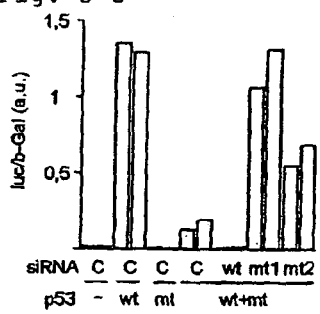
Figure 5:
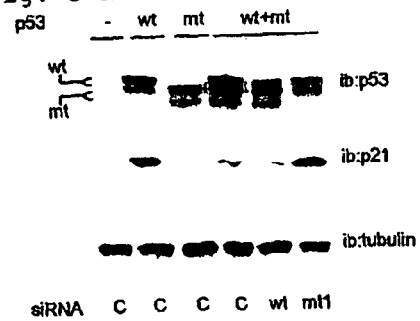

As shown in FIGS. 5 F, G and H, the MDA 087 cells (stemming from a patient suffering from a Li-Fraumeni cancer syndrome and expressing the mutant R248W) were transfected with a siRNA directed against the mutant form (MT1) of p53, or with an irrelevant siRNA (C) (1.6 µg). Expression of p53 was detected in these cells by Western blot (FIG. 5F); the messenger RNAs were measured by quantitative CR (Light Cycler, Roche) (FIG. 5G) or immunofluorescence (FIG. 5H).

The MDA 087 cells were transfected with a siRNA recognizing the wild form (WT) or the mutated form (MT1) of p53 or by a control siRNA then subjected to a genotoxic stress by treatment with doxorubicin (200 ng/ml) for 24 h. The expression of the mutant form of p53 was detected by Western blot in the cells. It can be seen that the cells having received siRNA MT1 were not capable of stabilizing p53 in response to doxorubicin (FIG. 5I).

FIG. 5J shows the effect of the siRNAs MT1 and MT2 in cells that express the wild and mutated forms of p53. H1299-NCI cells, which do not express p53, were transfected (using lipofectamine) by a reporter vector carrying the gene of luciferase under control of a p53 response element and vectors of expression (400 ng) of the wild p53 (WT), mutated p53 (MT) or a mixture of the two (WT+MT), as indicated. siRNAs (400 ng) directed against the wild form (WT), the mutated form (MT1, MT2) or an irrelevant siRNA (C) were transfected at the same time. The cells were collected 24 hours later and analyzed for the expression of luciferase. Only the wild p53 activated the report vector and the co-expression of the mutant form inhibited this activity. The cotransfection of wild siRNA inhibited the expression of the wild protein and thus the residual activation of the reporter gene. The cotransfection of the siRNA MT1 and MT2, in contrast, restored this activation by blocking selectively the expression of the mutated form and preventing the negative transdominant effect that it exerts on the wild form of p53.

FIG. 5K shows a similar result on the expression of one of the targets of p53, the inhibitory protein of cell proliferation p21, in cells treated as in FIG. 5F. The expression of p21, detected by Western blot, was activated by wild p53 and inhibited when the mutant was co-expressed. This inhibition was lifted in the presence of siRNA MT 1.

EXAMPLE 6

Inhibition of the Viral Protein E6

I—Preparation of the Oligonucleotides

A siRNA directed against the HPV protein E6 was also prepared. It responds to the following sequence:

```
HPV-16-S2
Sense:
5'[CCACAGUUAUGCACAUAUC]RNA[TT]DNA    (SEQ ID NO.27)

Anti:
5'[GCUCUGUGCAUAACUUGG]RNA[TT]DNA     (SEQ ID NO.28)
```

II—Results

Figure 6:
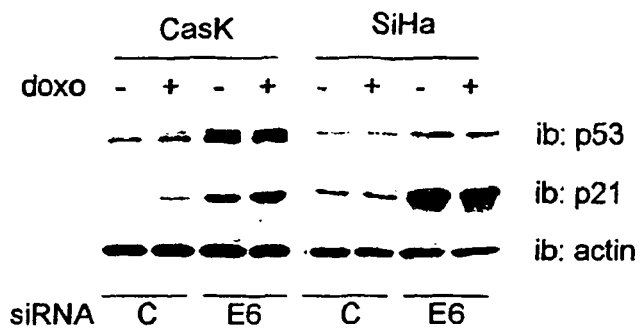
FIG. 6A to FIG. 6D show the inhibition of the expression of the protein E6 of the human papilloma virus HPV by specific siRNAs and the consequences of this inhibition.
Figure 6:
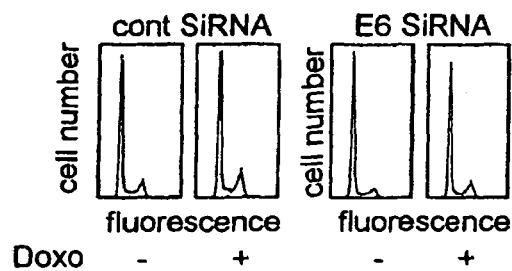
Figure 6:
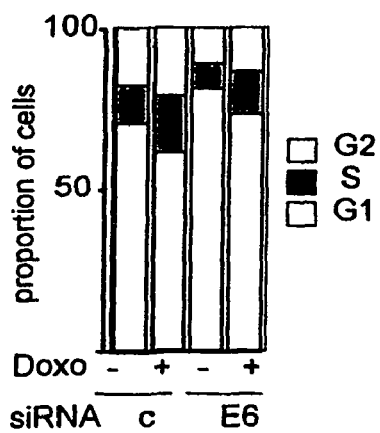

As shown in FIG. 6B, CasKi and SiHA cells, both expressing HPV protein E6, were transfected with the indicated siRNAs, treated or not treated as indicated with doxorubicin and analyzed by Western blot using the indicated antibodies. Treatment of the cells with siRNA E6 induced an augmentation in the expression of P53. This expression of p53 was manifested by an augmentation of the expression of the protein p21.

As shown in FIG. 6C, the cell cycle of the treated siHA cells as in FIG. 6B was analyzed by FACS. The figure represents a characteristic experiment. There was seen an augmentation of cells in phase G1 (FIG. 6D) in the cells treated with siRNA E6, an augmentation which was also seen in the cells when they were treated with doxorubicin.

EXAMPLE 7

Effect of the RNA/RNA Oligonucleotides and the DNA/RNA Hybrids

I—Introduction

The invention envisages the use of DNA/RNA hybrid oligonucleotides as alternative to the RNA/RNA oligonucleotides for inhibiting specifically the expression of a gene. In the case of the DNA/RNA hybrids, the sense strand is preferentially of a DNA nature and the antisense strand of a RNA nature. The other aspects related notably to the size of the oligonucleotides, the nature of the 3' ends and the mode of synthesis are the same as for the RNA/RNA oligonucleotides. The applications of these DNA/RNA hybrids are identical to those previously described for the RNA/RNA siRNA especially with regard to the therapeutic and diagnostic applications and the validation of genes. However, the doses of oligonucleotides employed in order to obtain the same effects with the DNA/RNA hybrids and RNA/RNA can be different.

II—Preparation of the Oligonucleotides

The sense strand is the one whose sequence is identical to that of the messenger RNA. The antisense strand is the strand complementary to the sense strand. By convention, in a duplex the nature of the strands is indicated in the order sense/antisense. Thus, for example, a DNA/RNA hybrid, noted as D/R, is a oligonucleotide the sense strand of which is of a DNA nature and the antisense strand of which is of a RNA nature and of a sequence complementary to the messenger RNA.

In the experiments described, the oligonucleotides whose sequence is indicated below were used.

For the GFP:

```
GFP:
Sense:
[GCAAGCTGACCCTGAAGTTCAT]DNA          (SEQ ID NO.29)

Anti:
[GAACUUCAGGGUCAGCUUGCCG]RNA          (SEQ ID NO.30)

Control GFP:
Sense:
[CAUGUCAUGUGUCACAUCUC]RNA[TT]DNA     (SEQ ID NO.31)

Antisense:
[GAGAUGUGACACAUGACAUG]RNA[TT]DNA     (SEQ ID NO.32)
```

FOR THE LNCaP: The underlined bases below correspond to the mutation of the androgen receptor expressed in the cells of human prostate carcinoma (LNCaP).

```
LNCaP:
Sense:
[GCATCAGTTCGCTTTTGACTT]DNA           (SEQ ID NO.33)

[GCAUCAGUUCGCUUUUGAC]RNA-TT[DNA]     (SEQ ID NO.34)

Antisense:
[GTCAAAAGCGAACTGATGCTT]DNA           (SEQ ID NO.35)

[GUCAAAAGCGAACUGAUGC]RNA = TT[DNA]   (SEQ ID NO.36)

Control LNCaP:
Sense:
[GUUCGGUCUGCUUACACUA]RNA-TT[DNA]     (SEQ ID NO.37)

Antisense:
[UAGUGUAAGCAGACCGAAC]RNA-TT[DNA]     (SEQ ID NO.38)
```

For p53:
The DNA of the hybrids noted H1 comprise RNA bases (U, underlined).
The mutation present in the MT1 oligonucleotides is indicated in italics.

```
WT:
Sense:
5'[GCAUGAACCGGAGGCCCAU]RNA[TT]DNA    (SEQ ID NO.39)

Anti:
5'[AUGGGCCUCCGGUUCAUGC]RNA[TT]DNA    (SEQ ID NO.40)

WT H1 D/R:
Sense:
5'[GCAUGAACCGGAGGCCCAUTT]DNA         (SEQ ID NO.41)

Anti:
5'[AUGGGCCUCCGGUUCAUGC]RNA[TT]DNA    (SEQ ID NO.42)

WT H1 R/D:
Sense:
5'[GCAUGAACCGGAGGCCCAU]RNA[TT]DNA    (SEQ ID NO.43)

Anti:
5'[AUGGGCCUCCGGUUCAUGCTT]DNA         (SEQ ID NO.44)

WT H2 R/D:
Sense:
5'[GCATGAACCGGAGGCCCATTT]DNA         (SEQ ID NO.45)

Anti:
5'[AUGGGCCYCCGGUUCAYGC]RNA[TT]DNA    (SEQ ID NO.46)

WT H2 R/D:
Sense:
5'[GCAUGAACCGGAGGCCCAU]RNA[TT]DNA    (SEQ ID NO.47)

Anti:
5'[ATGGGCCUTCCGGTTCATGCTT]DNA        (SEQ ID NO.48)

MT1 (R248W)**:
Sense:
5'[GCAUGAACUGGAGGCCCAU]RNA[TT]DNA    (SEQ ID NO.49)

Anti:
5'[AUGGGCCUCCAGUUCAUGC]RNA[TT]DNA    (SEQ ID NO.50)

MT1 H1 D/R:
Sense:
5'[GCAUGAACUGGAGGCCCAUTT]DNA         (SEQ ID NO.51)

Anti:
5'[AUGGGCCUCCAGUUCAUGC]RNA[TT]DNA    (SEQ ID NO.52)

MT1 H1 R/D:
Sense:
5'[GCAUGAACUGGAGGCCCAU]RNA[TT]DNA    (SEQ ID NO.53)

Anti:
5'[AUGGGCCUCCAGUUCAUGCTT]DNA         (SEQ ID NO.54)

MT1 H2 D/R:
Sense:
5'[GCATGAACTGGAGGCCCATTT]DNA         (SEQ ID NO.55)

Anti:
5'[AUGGGCCUCCAGUUCAUGC]RNA[TT]DNA    (SEQ ID NO.56)

MT1 H2 R/D:
Sense:
5'[GCATGAACTGGAGGCCCAT]RNA[TT]DNA    (SEQ ID NO.57)

Anti:
5'[AUGGGCCUCCAGUUCAUGCTT]DNA         (SEQ ID NO.58)
```

II—Results

1) Inhibition of the GFP (Green Fluorescent Protein) by the DNA/RNA Hybrids

Figure 7:
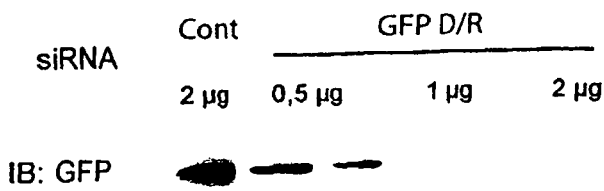
FIG. 7A to FIG. 7E the use of hybrid siRNAs comprising DNA bases and RNA bases.
Figure 7:
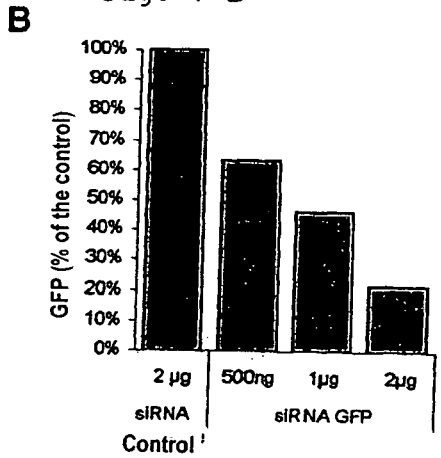
Figure 7:
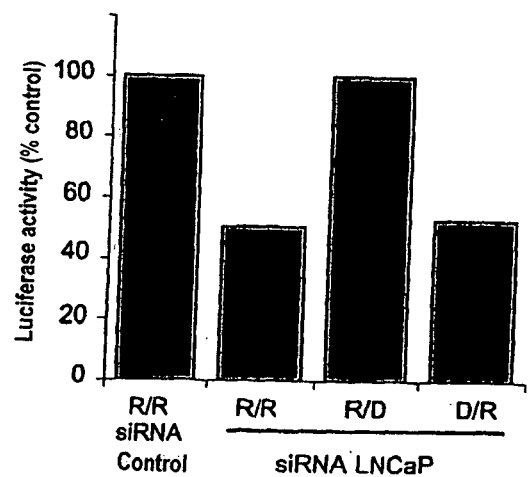
Figure 7:
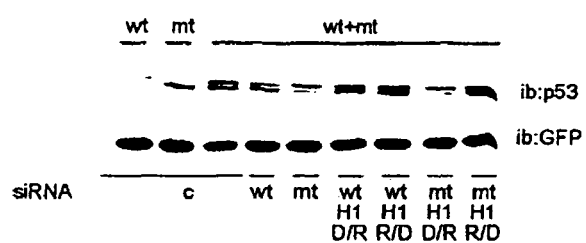
Figure 7:
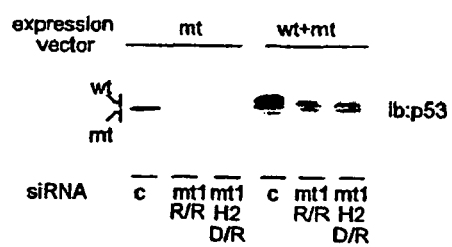

The control siRNAs (R/R) or GFP (D/R) in increasing doses were introduced by transfection using the Polyfect kit in C2C12 mouse myoblasts at the same time as a GFP expression vector. The GFP level was monitored by Western blot (FIG. 7A) and by direct measurement of the fluorescence emitted by the GFP by means of a fluorometer (FIG. 7B). There was seen a strong inhibition (up to 80%) of the expression of GFP by the DNA/RNA hybrid siRNAs.

2) Inhibition of the Androgen Receptor by the DNA/RNA Hybrids

FIG. 7D shows that the H1 D/R hybrids are as effective as the R/R for inhibiting the expression of genes. H1299-NCI cells, which do not express p53, were transfected (using lipofectamine) by vectors of expression (400 ng) of wild p53 (WT), mutated p53 (MT) or a mixture of the two (WT+MT), as indicated. A CMV-GFP vector was also transfected as internal control. The siRNAs (400 ng) directed against the wild form (WT), the mutated form (MT) or an irrelevant siRNA (CTRL) were transfected at the same time. The cells were collected 24 hours later and analyzed by Western blot with an antibody directed against p53 (D01, Santa Cruz) or GFP (Santa-Cruz) to monitor the transfection efficacy. Note: the expression of the mutated form of the protein stabilizes the wild form.

FIG. 7E shows that the H2 D/R hybrids were as effective as the R/R for inhibiting the expression of the genes. The H1299-NCI cells, which do not express p53, were transfected (using lipofectamine) by expression vectors (400 ng) of wild p53 (WT), mutated p53 (MT) and a mixture of the two (WT+MT) as indicated. The siRNAs (400 ng) directed against the wild form (WT), the mutated form (MT) or an irrelevant siRNA (C) were transfected at the same time. The cells were collected 24 hours later and analyzed by Western blot with an antibody directed against p53 (D01, Santa Cruz).

EXAMPLE 8

Administration In Vivo of siRNA Via Different Routes

Tumor cells expressing luciferase in a stable manner were injected subcutaneously to nude mice (1 million cells in the right flank). On the 8th day of tumor growth, the tumors having an average volume of 200 mm³ were injected either with control siRNAs (mixed sequence of HIF1α, see example 3) or with a siRNA directed against luciferase. The control siRNAs (3 μg/mouse) were injected in a volume of 50 μl in PBS via the subcutaneous route in the animal's flank.

The luciferase siRNAs were injected at the rate of 3 μg/mouse (3 animals in each group) in 50 μl of PBS via the subcutaneous route (sc), the intraperitoneal route (ip), the intravenous route (iv) (tail vein) or the intratumoral route (it). In this latter case, the luciferase siRNAs (3 μg/mouse) were diluted in only 20 μl of PBS.

Three days after injection of the siRNAs, the animals were sacrificed, the tumors were collected and homogenized with a Polytron grinder. Quantitative determination of the proteins and measurement of the luciferase activity in a luminometer were performed on the homogenates.

Figure 8:
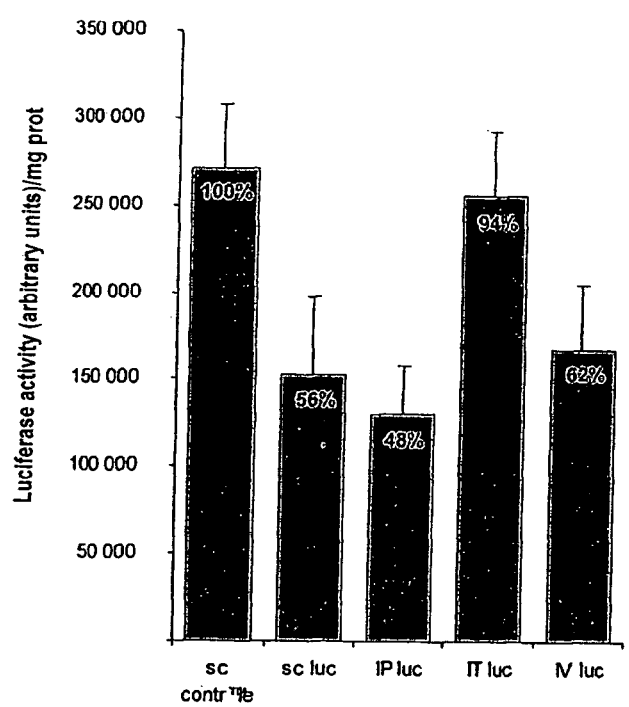
FIG. 8 shows the inhibition of luciferase in tumors expressing this enzyme by injection of siRNA via the subcutaneous, intratumoral, intraperitoneal or intravenous route.

The results shown in FIG. 8 show the luciferase activity in relation to the quantity of protein.

The invention claimed is:

1. A method for reducing tumor volume of prostate cancer and fibrosarcoma in a subject, comprising administering to said subject a pharmaceutical composition comprising a double-strand oligonucleotide consisting of SEQ ID NO: 7 and SEQ ID NO: 8.

2. A method for treating a pathological hypervascularization in tumoral development wherein VEGF is overexpressed, comprising directly contacting a VEGF overexpressing tumor cell with a pharmaceutical composition comprising a double-strand oligonucleotide consisting of SEQ ID NO: 7 and SEQ ID NO: 8.

3. A method for inhibiting VEGF expression in a subject, comprising administering to said subject a pharmaceutical composition comprising a double-strand oligonucleotide consisting of SEQ ID NO: 7 and SEQ ID NO: 8.

* * * * *

SEQUENCE LISTING

<160> NUMBER OF SEQ ID NOS: 77

<210> SEQ ID NO 1
<211> LENGTH: 1182
<212> TYPE: DNA
<213> ORGANISM: Homo sapiens
<220> FEATURE:
<221> NAME/KEY: misc_feature
<222> LOCATION: (1)..(1182)
<223> OTHER INFORMATION: sequence of the gene p53

<400> SEQUENCE: 1

```
atggaggagc cgcagtcaga tcctagcgtc gagccccctc tgagtcagga aacattttca       60
gacctatgga aactacttcc tgaaaacaac gttctgtccc ccttgccgtc ccaagcaatg      120
gatgatttga tgctgtcccc ggacgatatt gaacaatggt tcactgaaga cccaggtcca      180
gatgaagctc ccagaatgcc agaggctgct ccccccgtgg ccctgcacc agcagctcct      240 acaccggcgg cccctgcacc agccccctcc tggcccctgt catcttctgt cccttcccag      300
aaaacctacc agggcagcta cggtttccgt ctgggcttct tgcattctgg gacagccaag      360
tctgtgactt gcacgtactc ccctgccctc aacaagatgt tttgccaact ggccaagacc      420
tgccctgtgc agctgtgggt tgattccaca ccccgcccg gcacccgcgt ccgcgccatg      480
gccatctaca agcagtcaca gcacatgacg gaggttgtga ggcgctgccc ccaccatgag      540
cgctgctcag atagcgatgg tctggcccct cctcagcatc ttatccgagt ggaaggaaat      600
ttgcgtgtgg agtatttgga tgacagaaac acttttcgac atagtgtggt ggtgccctat      660
gagccgcctg aggttggctc tgactgtacc accatccact acaactacat gtgtaacagt      720
tcctgcatgg gcggcatgaa ccggaggccc atcctcacca tcatcacact ggaagactcc      780
agtggtaatc tactgggacg gaacagcttt gaggtgcgtg tttgtgcctg tcctgggaga      840
gaccggcgca cagaggaaga gaatctccgc aagaaagggg agcctcacca cgagctgccc      900
ccagggagca ctaagcgagc actgcccaac aacaccagct cctctcccca gccaaagaag      960
aaaccactgg atggagaata tttcaccctt cagatccgtg ggcgtgagcg cttcgagatg     1020
ttccgagagc tgaatgaggc cttggaactc aaggatgccc aggctgggaa ggagccaggg     1080
gggagcaggg ctcactccag ccacctgaag tccaaaaagg gtcagtctac ctcccgccat     1140
aaaaaactca tgttcaagac agaagggcct gactcagact ga                        1182
```

```
<210> SEQ ID NO 2
<211> LENGTH: 7904
<212> TYPE: DNA
<213> ORGANISM: Homo sapiens
<220> FEATURE:
<221> NAME/KEY: misc_feature
<222> LOCATION: (1)..(7904)
<223> OTHER INFORMATION: variant HPV16

<400> SEQUENCE: 2
actacaataa ttcatgtata aaactaaggg cgtaaccgaa atcggttgaa ccgaaaccgg      60
ttagtataaa agcagacatt ttatgcacca aaagagaact gcaatgtttc aggacccaca    120
ggagcgaccc agaaagttac cacagttatg cacagagctg caaacaacta tacatgatat    180
aatattagaa tgtgtgtact gcaagcaaca gttactgcga cgtgaggtat atgactttgc    240
ttttcgggat ttatgcatag tatatagaga tgggaatcca tatgctgtat gtgataaatg    300
tttaaagttt tattctaaaa ttagtgagta tagacattat tgttatagtt tgtatggaac    360
aacattagaa cagcaataca acaaaccgtt gtgtgatttg ttaattaggt gtattaactg    420
tcaaaagcca ctgtgtcctg aagaaaagca aagacatctg gacaaaaagc aaagattcca    480
taatataagg ggtcggtgga ccggtcgatg tatgtcttgt tgcagatcat caagaacacg    540
tagagaaacc cagctgtaat catgcatgga gatacaccta cattgcatga atatatgtta    600
gatttgcaac cagagacaac tgatctctac tgttatgagc aattaaatga cagctcagag    660
gaggaggatg aaatagatgg tccagctgga caagcagaac cggacagagc ccattacaat    720
attgtaacct tttgttgcaa gtgtgactct acgcttcggt tgtgcgtaca aagcacacac    780
gtagacattc gtactttgga agacctgtta atgggcacac taggaattgt gtgccccatc    840
tgttctcaga aaccataatc taccatggct gatcctgcag gtaccaatgg ggaagagggt    900
acgggatgta atggatggtt ttatgtagag gctgtagtgg aaaaaaaaac agggatgct     960 atatcagatg acgagaacga aaatgacagt gatacaggtg aagatttggt agattttata   1020
gtaaatgata atgattattt aacacaggca gaaacagaga cagcacatgc gttgtttact   1080
gcacaggaag caaacaaca tagagatgca gtacaggttc taaaacgaaa gtatttggta   1140
gtccacttag tgatattagt ggatgtgtag acaataatat tagtcctaga ttaaaagcta   1200
tatgtataga aaaacaaagt agagctgcaa aaggagatt atttgaaagc gaagacagcg   1260
ggtatggcaa tactgaagtg gaaactcagc agatgttaca ggtagaaggg cgccatgaga   1320
ctgaaacacc atgtagtcag tatagtggtg gaagtgggg tggttgcagt cagtacagta   1380
gtggaagtgg gggagagggt gttagtgaaa gacacactat atgccaaaca ccacttacaa   1440
atattttaaa tgtactaaaa actagtaatg caaaggcagc aatgttagca aaatttaaag   1500
agttatacgg ggtgagtttt tcagaattag taagaccatt taaaagtaat aaatcaacgt   1560
gttgcgattg tgtattgct gcatttggac ttacacccag tatagctgac agtataaaaa   1620
cactattaca acaatattgt ttatatttac acattcaaag tttagcatgt tcatgggaa    1680 tggttgtgtt actattagta agatataaat gtgaaaaaa tagagaaaca attgaaaaat   1740
tgctgtctaa actattatgt gtgtctccaa tgtgtatgat gatagagcct ccaaaattgc   1800
gtagtacagc agcagcatta tattggtata aacaggtat atcaaatatt agtgaagtgt   1860
atggagacac gccagaatgg atacaaagac aaacagtatt acaacatagt tttaatgatt   1920
gtacatttga attatcacag atggtacaat gggcctacga taatgacata gtagacgata   1980
gtgaaattgc atataaatat gcacaattgg cagacactaa tagtaatgca agtgccttc    2040 taaaaagtaa ttcacaggca aaaattgtaa aggattgtgc aacaatgtgt agacattata   2100
```

```
aacgagcaga aaaaaaacaa atgagtatga gtcaatggat aaaatataga gtgataggg      2160 tagatgatgg aggtgattgg aagcaaattg ttatgttttt aaggtatcaa ggtgtagagt      2220
ttatgtcatt tttaactgca ttaaaaagat ttttgcaagg catacctaaa aaaaattgca      2280
tattactata tggtgcagct aacacaggta aatcattatt tggtatgagt ttaatgaaat      2340
ttctgcaagg gtctgtaata tgttttgtaa attctaaaag ccattttggg ttacaaccat      2400
tagcagatgc caaaataggt atgttagatg atgctacagt gccctgttgg aactacatag      2460
atgacaattt aagaaatgca ttggatggaa atttagtttc tatggatgta aagcatagac      2520
cattggtaca actaaaatgc cctccattat taattacatc taacattaat gctggtacag      2580
attctaggtg gccttattta cataatagat tggtggtgtt tacatttcct aatgagtttc      2640
catttgacga aaacggaaat ccagtgtatg agcttaatga taagaactgg aaatcctttt      2700
tctcaaggac gtggtccaga ttaagtttgc acgaggacga ggacaaggaa acgatggag       2760 actctttgcc aacgtttaaa tgtgtgtcag gacaaaatac taacacatta tgaaaatgat      2820
agtacagacc tacgtgacca tatagactat tggaaacaca tgcgcctaga atgtgctatt      2880
tattacaagg ccagagaaat gggatttaaa catattaacc accaagtggt gccaacactg      2940
gctgtatcaa agaataaagc attacaagca attgaactgc aactaacgtt agaaacaata      3000
tataactcac aatatagtaa tgaaaagtgg acattcaaag acgttagcct tgaagtgtat      3060
ttaactgcac caacaggatg tataaaaaaa catggatata cagtggaagt gcagtttgat      3120
ggagacatat gcaatacaat gcattataca aactggacac atatatata ttgtgaagaa      3180 gcatcagtaa ctgtggtaga gggtcaagtt gactattatg gtttatatta tgttcatgaa      3240
ggaatacgaa catattttgt gcagtttaaa gatgatgcag aaaaatatag taaaaataaa      3300
gtatgggaag ttcatgcggg tggtcaggta atattatgtc ctacatctgt gtttagcagc      3360
aacgaagtat cctctcctga aattattagg cagcacttgg ccaaccaccc cgccgcgacc      3420
cataccaaag ccgtcgcctt gggcaccgaa gaaacacaga cgactatcca gcgaccaaga      3480
tcagagccag acaccggaaa cccctgccac accactaagt tgttgcacag agactcagtg      3540
gacagtgctc caatcctcac tgcatttaac agctcacaca aaggacggat taactgtaat      3600
agtaacacta cacccatagt acatttaaaa ggtgatgcta atactttaaa atgtttaaga      3660
tatagattta aaaagcattg tacattgtat actgcagtgt cgtctacatg gcattggaca      3720
ggacataatg taaaacataa aagtgcaatt gttacactta catatgatag tgaatggcaa      3780
cgtgaccaat ttttgtctca agttaaaata ccaaaaacta ttacagtgtc tactggattt      3840
atgtctatat gacaaatctt gatactgcat ccacaacatt actggcgtgc tttttgcttt      3900
gctttgtgtg cttttgtgtg tctgcctatt aatacgtccg ctgcttttgt ctgtgtctac      3960
atacacatca ttaataatat tggtattact attgtggata acagcagcct ctgcgtttag      4020
gtgttttatt gtatatatta tatttgttta tataccatta ttttttaatac atacacatgc      4080 acgcttttta attacataat gtatatgtac ataatgtaat tgttacatat aattgttgta      4140
taccataact tactattttt tcttttttat tttcatatat aatttttttt tttgtttgtt      4200
tgtttgtttt ttaataaact gttattactt aacaatgcga cacaaacgtt ctgcaaaacg      4260
cacaaaacgt gcatcggcta cccaacttta taaaacatgc aaacaggcag gtacatgtcc      4320
acctgacatt ataccttaagg ttgaaggcaa aactattgct gaacaaatat tacaatatgg      4380 aagtatggg gtatttttg gtgggttagg aattggaaca gggtcgggta caggcggacg      4440
cactgggtat attccattgg gaacaaggcc tcccacagct acagatacac ttgctcctgt      4500
```

-continued

```
aagacccect ttaacagtag atcctgtggg cccttctgat ccttctatag tttctttagt    4560
ggaagaaact agttttattg atgctggtgc accaacatct gtaccttcca ttcccccaga    4620
tgtatcagga tttagtatta ctacttcaac tgataccaca cctgctatat tagatattaa    4680
taatactgtt actactgtta ctacacataa taatcccact ttcactgacc catctgtatt    4740
gcagcctcca acacctgcag aaactggagg gcattttaca ctttcatcat ccactattag    4800
tacacataat tatgaagaaa ttcctatgga tacatttatt gttagcacaa accctaacac    4860
agtaactagt agcacaccca taccagggtc tcgcccagtg gcacgcctag gattatatag    4920
tcgcacaaca caacaggtta aagttgtaga ccctgctttt gtaaccactc ccactaaact    4980
tattacatat gataatcctg catatgaagg tatagatgtg gataatacat tatattttc    5040 tagtaatgat aatagtatta atatagctcc agatcctgac tttttggata tagttgcttt    5100
acataggcca gcattaacct ctaggcgtac tggcattagg tacagtagaa ttggtaataa    5160
acaaacacta cgtactcgta gtggaaaatc tataggtgct aaggtacatt attattatga    5220
tttaagtact attgatcctg cagaagaaat agaattacaa actataacac cttctacata    5280
tactaccact tcacatgcag cctcacctac ttctattaat aatggattat atgatattta    5340
tgcagatgac tttattacag atacttctac aaccccggta ccatctgtac cctctacatc    5400
tttatcaggt tatattcctg caaatacaac aattccttt ggtggtgcat acaatattcc    5460
tttagtatca ggtcctgata tacccattaa tataactgac caagctcctt cattaattcc    5520
tatagttcca gggtctccac aatatacaat tattgctgat gcaggtgact ttatttaca    5580 tcctagttat tacatgttac gaaaacgacg taaacgttta ccatattttt tttcagatgt    5640
ctctttggct gcctagtgag gccactgtct acttgcctcc tgtcccagta tctaaggttg    5700
taagcacgga tgaatatgtt gcacgcacaa acatatatta tcatgcagga acatccagac    5760
tacttgcagt tggacatccc tattttccta ttaaaaaacc taacaataac aaaatattag    5820
ttcctaaagt atcaggatta caatacaggg tatttagaat acatttacct gaccccaata    5880
agtttggttt tcctgacacc tcattttata atccagatac acagcggctg gtttgggcct    5940
gtgtaggtgt tgaggtaggt cgtggtcagc cattaggtgt gggcattagt ggccatcctt    6000
tattaaataa attggatgac acagaaaatg ctagtgctta tgcagcaaat gcaggtgtgg    6060
ataatagaga atgtatatct atggattaca aacaaacaca attgtgttta attggttgca    6120
aaccacctat aggggaacac tggggcaaag gatccccatg taccaatgtt gcagtaaatc    6180
caggtgattg tccaccatta gagttaataa acacagttat tcaggatggt gatatggttc    6240
atactggctt tggtgctatg gactttacta cattacaggc taacaaaagt gaagttccac    6300
tggatatttg tacatctatt tgcaaatatc cagattatat taaaatggtg tcagaaccat    6360
atggcgacag cttatttttt tatttacgaa gggaacaaat gtttgttaga catttattta    6420
atagggctgg tactgttggt gaaaatgtac cagacgattt atacattaaa ggctctgggt    6480
ctactgcaaa tttagccagt tcaaattatt ttcctacacc tagtggttct atggttacct    6540
ctgatgccca aatattcaat aaaccttatt ggttacaacg agcacagggc cacaataatg    6600
gcatttgttg gggtaaccaa ctatttgtta ctgttgttga tactcacgc agtacaaata    6660 tgtcattatg tgctgccata tctacttcag aaactacata taaaaatact aactttaagg    6720
agtacctacg acatggggag gaatatgatt tacagtttat ttttcaactg tgcaaaataa    6780
ccttaactgc agacgttatg acatacatac attctatgaa ttccactatt ttggaggact    6840
ggaattttgg tctacaacct cccccaggag gcacactaga agatacttat aggtttgtaa    6900
```

```
cccaggcaat tgcttgtcaa aaacatacac ctccagcacc taaagaagat gatcccctta    6960
aaaaatacac tttttgggaa gtaaatttaa aggaaaagtt ttctgcagac ctagatcagt    7020
ttcctttagg acgcaaattt ttactacaag caggattgaa ggccaaacca aaatttacat    7080
taggaaaacg aaaagctaca cccaccacct catctacctc tacaactgct aaacgcaaaa    7140
aacgtaagct gtaagtattg tatgtatgtt gaattagtgt tgtttgttgt gtatatgttt    7200
gtatgtgctt gtatgtgctt gtaaatatta agttgtatgt gtgtttgtat gtatggtata    7260
ataaacacgt gtgtatgtgt ttttaaatgc ttgtgtaact attgtgtcat gcaacataaa    7320
taaacttatt gtttcaacac ctactaattg tgttgtggtt attcattgta tataaactat    7380
atttgctaca tcctgttttt gttttatata tactatattt tgtagcgcca ggcccatttt    7440
gtagcttcaa ccgaattcgg ttgcatgctt tttggcacaa aatgtgtttt tttaaatagt    7500
tctatgtcag caactatggt ttaaacttgt acgtttcctg cttgccatgc gtgccaaatc    7560
cctgttttcc tgacctgcac tgcttgccaa ccattccatt gttttttaca ctgcactatg    7620
tgcaactact gaatcactat gtacattgtg tcatataaaa taaatcacta tgcgccaacg    7680
ccttacatac cgctgttagg cacatatttt tggcttgttt taactaacct aattgcatat    7740
ttggcataag gtttaaactt ctaaggccaa ctaaatgtca ccctagttca tacatgaact    7800
gtgtaaaggt tagtcataca ttgttcattt gtaaaactgc acatgggtgt gtgcaaaccg    7860
attttgggtt acacatttac aagcaactta tataataata ctaa                    7904

<210> SEQ ID NO 3
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: sense strand of PML-rare
<220> FEATURE:
<221> NAME/KEY: misc_feature
<222> LOCATION: (21)..(22)
<223> OTHER INFORMATION: added thymine residues

<400> SEQUENCE: 3
caugucaugu gucacaucuc tt                                              22

<210> SEQ ID NO 4
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: antisense strand of PML-rare
<220> FEATURE:
<221> NAME/KEY: misc_feature
<222> LOCATION: (21)..(22)
<223> OTHER INFORMATION: added thymine residues

<400> SEQUENCE: 4
```

-continued gagaugugac acaugacaug tt                                                22

<210> SEQ ID NO 5
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: sense strand of PML-rare
<220> FEATURE:
<221> NAME/KEY: misc_feature
<222> LOCATION: (21)..(22)
<223> OTHER INFORMATION: added thymine residues

<400> SEQUENCE: 5
ggggaggcag ccauugagac tt                                                22

<210> SEQ ID NO 6
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: antisense strand of PML-rare
<220> FEATURE:
<221> NAME/KEY: misc_feature
<222> LOCATION: (21)..(22)
<223> OTHER INFORMATION: added thymine residues

<400> SEQUENCE: 6
gucucaaugg cugccucccc tt                                                22

<210> SEQ ID NO 7
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(21)
<223> OTHER INFORMATION: sequence stemming from human VEGF
<220> FEATURE:
<221> NAME/KEY: misc_feature
<222> LOCATION: (22)..(23)
<223> OTHER INFORMATION: added thymine residues

<400> SEQUENCE: 7
augugaaugc agaccaaaga att                                               23

<210> SEQ ID NO 8
<211> LENGTH: 23
<212> TYPE: DNA
<213> ORGANISM: Artificial Sequence

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(21)
<223> OTHER INFORMATION: sequence stemming from human VEGF
<220> FEATURE:
<221> NAME/KEY: misc_feature
<222> LOCATION: (22)..(23)
<223> OTHER INFORMATION: added thymine residues

<400> SEQUENCE: 8
uucuuugguc ugcauucaca utt                                            23

<210> SEQ ID NO 9
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: sequence stemming from human VEGF
<220> FEATURE:
<221> NAME/KEY: misc_feature
<222> LOCATION: (21)..(22)
<223> OTHER INFORMATION: added thymine residues

<400> SEQUENCE: 9
caugucaugu gucacaucuc tt                                             22

<210> SEQ ID NO 10
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: sequence stemming from human VEGF
<220> FEATURE:
<221> NAME/KEY: misc_feature
<222> LOCATION: (21)..(22)
<223> OTHER INFORMATION: added thymine residues

<400> SEQUENCE: 10
gagaugugac acaugacaug tt                                             22

<210> SEQ ID NO 11
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
```

```
<222> LOCATION: (1)..(21)
<223> OTHER INFORMATION: sequence stemming from human HIF1-alpha
<220> FEATURE:
<221> NAME/KEY: misc_feature
<222> LOCATION: (22)..(23)
<223> OTHER INFORMATION: added thymine residues

<400> SEQUENCE: 11
caugugacca ugaggaaaug att                                              23

<210> SEQ ID NO 12
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(21)
<223> OTHER INFORMATION: sequence stemming from human HIF1-alpha
<220> FEATURE:
<221> NAME/KEY: misc_feature
<222> LOCATION: (22)..(23)
<223> OTHER INFORMATION: added thymine residues

<400> SEQUENCE: 12 ucauuccuc auggucacau gtt                                               23

<210> SEQ ID NO 13
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(21)
<223> OTHER INFORMATION: sequence stemming from human HIF1-alpha
<220> FEATURE:
<221> NAME/KEY: misc_feature
<222> LOCATION: (22)..(23)
<223> OTHER INFORMATION: added thymine residues

<400> SEQUENCE: 13
gauagcaaug acgaaugcgu att                                              23

<210> SEQ ID NO 14
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(21)
<223> OTHER INFORMATION: sequence stemming from human HIF1-alpha
<220> FEATURE:
<221> NAME/KEY: misc_feature
<222> LOCATION: (22)..(23)
<223> OTHER INFORMATION: added thymine residues

<400> SEQUENCE: 14
```
uacgcauucg ucauugcuau ctt                                             23

<210> SEQ ID NO 15
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(21)
<223> OTHER INFORMATION: sequence stemming from human androgen receptor
<220> FEATURE:
<221> NAME/KEY: misc_feature
<222> LOCATION: (22)..(23)
<223> OTHER INFORMATION: added thymine residues

<400> SEQUENCE: 15
gacucagcug ccccauccac gtt                                             23

<210> SEQ ID NO 16
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(21)
<223> OTHER INFORMATION: sequence stemming from human HIF1-alpha
<220> FEATURE:
<221> NAME/KEY: misc_feature
<222> LOCATION: (22)..(23)
<223> OTHER INFORMATION: added thymine residues

<400> SEQUENCE: 16
cguggauggg gcagcugagu ctt                                             23

<210> SEQ ID NO 17
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(21)
<223> OTHER INFORMATION: sequence stemming from human HIF1-alpha
<220> FEATURE:
<221> NAME/KEY: misc_feature
<222> LOCATION: (22)..(23)
<223> OTHER INFORMATION: added thymine residues

<400> SEQUENCE: 17
gauagcaaug acgaaugcgu att                                             23

<210> SEQ ID NO 18
<211> LENGTH: 23
<212> TYPE: DNA
<213> ORGANISM: Artificial Sequence

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(21)
<223> OTHER INFORMATION: sequence stemming from human HIF1-alpha
<220> FEATURE:
<221> NAME/KEY: misc_feature
<222> LOCATION: (22)..(23)
<223> OTHER INFORMATION: added thymine residues

<400> SEQUENCE: 18
uacgcauucg ucauugcuau ctt                                          23

<210> SEQ ID NO 19
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from human androgen receptor
      bearing mutation T8 77A
<220> FEATURE:
<221> NAME/KEY: misc_feature
<222> LOCATION: (20)..(21)
<223> OTHER INFORMATION: added thymine residues

<400> SEQUENCE: 19
gcaucaguuc gcuuuugact t                                            21

<210> SEQ ID NO 20
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from human androgen receptor
      bearing mutation T8 77A
<220> FEATURE:
<221> NAME/KEY: misc_feature
<222> LOCATION: (20)..(21)
<223> OTHER INFORMATION: added thymine residues

<400> SEQUENCE: 20
gucaaaagcg aacugaugct t                                            21

<210> SEQ ID NO 21
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
```

```
<220> FEATURE:
<221> NAME/KEY: misc_feature
<222> LOCATION: (1)..(19)
<223> OTHER INFORMATION: sequence stemming from wild human p53 (sense)
<220> FEATURE:
<221> NAME/KEY: misc_feature
<222> LOCATION: (20)..(21)
<223> OTHER INFORMATION: added thymine residues

<400> SEQUENCE: 21
gcaugaaccg gaggcccaut t                                                  21

<210> SEQ ID NO 22
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from wild human p53
      (antisense)
<220> FEATURE:
<221> NAME/KEY: misc_feature
<222> LOCATION: (20)..(21)
<223> OTHER INFORMATION: added thymine residues

<400> SEQUENCE: 22
augggccucc gguucaugct t                                                  21

<210> SEQ ID NO 23
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from muatated human p53
      bearing the mutation MT1 (r248w)(sense)
<220> FEATURE:
<221> NAME/KEY: misc_feature
<222> LOCATION: (20)..(21)
<223> OTHER INFORMATION: added thymine residues

<400> SEQUENCE: 23
gcaugaacug gaggcccaut t                                                  21

<210> SEQ ID NO 24
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from muatated human p53
      bearing the mutation MT1 (r248w)(antisense)
<220> FEATURE:
```

```
<221> NAME/KEY: misc_feature
<222> LOCATION: (20)..(21)
<223> OTHER INFORMATION: added thymine residues

<400> SEQUENCE: 24
augggccucc aguucaugct t                                              21

<210> SEQ ID NO 25
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from muatated human p53
      bearing the mutation MT2 (r248w)(sense)
<220> FEATURE:
<221> NAME/KEY: misc_feature
<222> LOCATION: (20)..(21)
<223> OTHER INFORMATION: added thymine residues

<400> SEQUENCE: 25
ucaugaacug gaggcccaut t                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from muatated human p53
      bearing the mutation MT2 (r248w)(antisense)
<220> FEATURE:
<221> NAME/KEY: misc_feature
<222> LOCATION: (20)..(21)
<223> OTHER INFORMATION: added thymine residues

<400> SEQUENCE: 26
augggccucc aguucaugat t                                              21

<210> SEQ ID NO 27
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from E6 of HPV (sense)
<220> FEATURE:
<221> NAME/KEY: misc_feature
<222> LOCATION: (20)..(21)
<223> OTHER INFORMATION: added thymine residues

<400> SEQUENCE: 27
```
ccacaguuau gcacagagct t							21

<210> SEQ ID NO 28
<211> LENGTH: 20
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: sequence stemming from E6 of HPV (antisense)
<220> FEATURE:
<221> NAME/KEY: misc_feature
<222> LOCATION: (19)..(20)
<223> OTHER INFORMATION: added thymine residues

<400> SEQUENCE: 28
gcucugugca uaacuuggtt							20

<210> SEQ ID NO 29
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(22)
<223> OTHER INFORMATION: sequence stemming from the gene coding GFP
      (sense strand)

<400> SEQUENCE: 29
gcaagctgac cctgaagttc at						22

<210> SEQ ID NO 30
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(22)
<223> OTHER INFORMATION: sequence stemming from the gene coding GFP
      (antisense strand)

<400> SEQUENCE: 30
gaacuucagg gucagcuugc cg						22

<210> SEQ ID NO 31
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:

```
<221> NAME/KEY: misc_feature
<222> LOCATION: (1)..(20)
<223> OTHER INFORMATION: sequence stemming from the gene coding GFP
      (sense strand)
<220> FEATURE:
<221> NAME/KEY: misc_feature
<222> LOCATION: (21)..(22)
<223> OTHER INFORMATION: added thymine residues

<400> SEQUENCE: 31
caugucaugu gucacaucuc tt                                              22

<210> SEQ ID NO 32
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: sequence stemming from the gene coding GFP
      (antisense strand)
<220> FEATURE:
<221> NAME/KEY: misc_feature
<222> LOCATION: (21)..(22)
<223> OTHER INFORMATION: added thymine residues

<400> SEQUENCE: 32
gagaugugac acaugacaug tt                                              22

<210> SEQ ID NO 33
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(21)
<223> OTHER INFORMATION: sequence stemming from the mutated human
      androgen receptor (sense strand)

<400> SEQUENCE: 33
gcatcagttc gcttttgact t                                               21

<210> SEQ ID NO 34
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human
      androgen receptor (sense strand)
<220> FEATURE:
<221> NAME/KEY: misc_feature
<222> LOCATION: (20)..(21)
<223> OTHER INFORMATION: added thymine residues
```

-continued

```
<400> SEQUENCE: 34
gcaucaguuc gcuuuugact t                                              21

<210> SEQ ID NO 35
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(21)
<223> OTHER INFORMATION: sequence stemming from the mutated human
      androgen receptor (sense strand)

<400> SEQUENCE: 35
gtcaaaagcg aactgatgct t                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human
      androgen receptor (sense strand)
<220> FEATURE:
<221> NAME/KEY: misc_feature
<222> LOCATION: (20)..(21)
<223> OTHER INFORMATION: added thymine residues

<400> SEQUENCE: 36
gucaaaagcg aacugaugct t                                              21

<210> SEQ ID NO 37
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human
      androgen receptor (sense strand)
<220> FEATURE:
<221> NAME/KEY: misc_feature
<222> LOCATION: (20)..(21)
<223> OTHER INFORMATION: added thymine residues

<400> SEQUENCE: 37
guucggucug cuuacacuat t                                              21

<210> SEQ ID NO 38
<211> LENGTH: 21
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human
      androgen receptor (antisense strand)
<220> FEATURE:
<221> NAME/KEY: misc_feature
<222> LOCATION: (20)..(21)
<223> OTHER INFORMATION: added thymine residues

<400> SEQUENCE: 38
uaguguaagc agaccgaact t                                             21

<210> SEQ ID NO 39
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the wild human p53 gene
      (sense strand)
<220> FEATURE:
<221> NAME/KEY: misc_feature
<222> LOCATION: (20)..(21)
<223> OTHER INFORMATION: added thymine residues

<400> SEQUENCE: 39
gcaugaaccg gaggcccaut t                                             21

<210> SEQ ID NO 40
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the wild human p53 gene
      (antisense strand)
<220> FEATURE:
<221> NAME/KEY: misc_feature
<222> LOCATION: (20)..(21)
<223> OTHER INFORMATION: added thymine residues

<400> SEQUENCE: 40
augggccucc gguucaugct t                                             21

<210> SEQ ID NO 41
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
```

```
        oligonucleotide
<220> FEATURE:
<221> NAME/KEY: misc_feature
<222> LOCATION: (1)..(19)
<223> OTHER INFORMATION: sequence stemming from the mutated human p53
      gene (antisense strand)
<220> FEATURE:
<221> NAME/KEY: misc_feature
<222> LOCATION: (20)..(21)
<223> OTHER INFORMATION: added thymine residues

<400> SEQUENCE: 41
gcaugaaccg gaggcccaut t                                                21

<210> SEQ ID NO 42
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human p53
      gene (sense strand)
<220> FEATURE:
<221> NAME/KEY: misc_feature
<222> LOCATION: (20)..(21)
<223> OTHER INFORMATION: added thymine residues

<400> SEQUENCE: 42
augggccucc gguucaugct t                                                21

<210> SEQ ID NO 43
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human p53
      gene (antisense strand)
<220> FEATURE:
<221> NAME/KEY: misc_feature
<222> LOCATION: (20)..(21)
<223> OTHER INFORMATION: added thymine residues

<400> SEQUENCE: 43
gcaugaaccg gaggcccaut t                                                21

<210> SEQ ID NO 44
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human p53
```

-continued

```
      gene (antisense strand)
<220> FEATURE:
<221> NAME/KEY: misc_feature
<222> LOCATION: (20)..(21)
<223> OTHER INFORMATION: added thymine residues

<400> SEQUENCE: 44
augggccucc gguucaugct t                                              21

<210> SEQ ID NO 45
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human p53
      gene (antisense strand)
<220> FEATURE:
<221> NAME/KEY: misc_feature
<222> LOCATION: (20)..(21)
<223> OTHER INFORMATION: added thymine residues

<400> SEQUENCE: 45
gcatgaaccg gaggcccatt t                                              21

<210> SEQ ID NO 46
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human p53
      gene (antisense strand)
<220> FEATURE:
<221> NAME/KEY: misc_feature
<222> LOCATION: (20)..(21)
<223> OTHER INFORMATION: added thymine residues

<400> SEQUENCE: 46
augggccucc gguucaugct t                                              21

<210> SEQ ID NO 47
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human p53
      gene (sense strand)
<220> FEATURE:
<221> NAME/KEY: misc_feature
<222> LOCATION: (20)..(21)
<223> OTHER INFORMATION: added thymine residues
```

<400> SEQUENCE: 47
gcaugaaccg gaggcccaut t                                              21

<210> SEQ ID NO 48
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: sequence stemming from the mutated human p53
      gene (antisense strand)
<220> FEATURE:
<221> NAME/KEY: misc_feature
<222> LOCATION: (21)..(22)
<223> OTHER INFORMATION: added thymine residues

<400> SEQUENCE: 48
atgggccutc cggttcatgc tt                                             22

<210> SEQ ID NO 49
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human p53
      gene (sense strand)
<220> FEATURE:
<221> NAME/KEY: misc_feature
<222> LOCATION: (20)..(21)
<223> OTHER INFORMATION: added thymine residues

<400> SEQUENCE: 49
gcaugaacug gaggcccaut t                                              21

<210> SEQ ID NO 50
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human p53
      gene (antisense strand)
<220> FEATURE:
<221> NAME/KEY: misc_feature
<222> LOCATION: (20)..(21)
<223> OTHER INFORMATION: added thymine residues

<400> SEQUENCE: 50
augggccucc aguucaugct t                                              21

```
<210> SEQ ID NO 51
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human p53
      gene (sense strand)
<220> FEATURE:
<221> NAME/KEY: misc_feature
<222> LOCATION: (20)..(21)
<223> OTHER INFORMATION: added thymine residues

<400> SEQUENCE: 51
gcaugaacug gaggcccaut t                                              21

<210> SEQ ID NO 52
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human p53
      gene (antisense strand)
<220> FEATURE:
<221> NAME/KEY: misc_feature
<222> LOCATION: (20)..(21)
<223> OTHER INFORMATION: added thymine residues

<400> SEQUENCE: 52
augggccucc aguucaugct t                                              21

<210> SEQ ID NO 53
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human p53
      gene (sense strand)
<220> FEATURE:
<221> NAME/KEY: misc_feature
<222> LOCATION: (20)..(21)
<223> OTHER INFORMATION: added thymine residues

<400> SEQUENCE: 53
gcaugaacug gaggcccaut t                                              21

<210> SEQ ID NO 54
<211> LENGTH: 21
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human p53
      gene (antisense strand)
<220> FEATURE:
<221> NAME/KEY: misc_feature
<222> LOCATION: (20)..(21)
<223> OTHER INFORMATION: added thymine residues

<400> SEQUENCE: 54
augggccucc aguucaugct t                                              21

<210> SEQ ID NO 55
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human p53
      gene (antisense strand)
<220> FEATURE:
<221> NAME/KEY: misc_feature
<222> LOCATION: (20)..(21)
<223> OTHER INFORMATION: added thymine residues

<400> SEQUENCE: 55
gcatgaactg gaggcccatt t                                              21

<210> SEQ ID NO 56
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human p53
      gene (antisense strand)
<220> FEATURE:
<221> NAME/KEY: misc_feature
<222> LOCATION: (20)..(21)
<223> OTHER INFORMATION: added thymine residues

<400> SEQUENCE: 56
augggccucc aguucaugct t                                              21

<210> SEQ ID NO 57
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
```

```
        oligonucleotide
<220> FEATURE:
<221> NAME/KEY: misc_feature
<222> LOCATION: (1)..(19)
<223> OTHER INFORMATION: sequence stemming from the mutated human p53
      gene (sense strand)
<220> FEATURE:
<221> NAME/KEY: misc_feature
<222> LOCATION: (20)..(21)
<223> OTHER INFORMATION: added thymine residues

<400> SEQUENCE: 57
gcatgaactg gaggcccatt t                                              21

<210> SEQ ID NO 58
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: sequence stemming from the mutated human p53
      gene (antisense strand)
<220> FEATURE:
<221> NAME/KEY: misc_feature
<222> LOCATION: (20)..(21)
<223> OTHER INFORMATION: added thymine residues

<400> SEQUENCE: 58
augggccucc aguucaugct t                                              21

<210> SEQ ID NO 59
<211> LENGTH: 3933
<212> TYPE: DNA
<213> ORGANISM: Homo sapiens
<220> FEATURE:
<221> NAME/KEY: misc_feature
<222> LOCATION: (1)..(3933)
<223> OTHER INFORMATION: hypoxia-inducible factor 1 subunit alpha
      (HIF1-alpha)

<400> SEQUENCE: 59
cacgaggcag cactctcttc gtcgcttcgg ccagtgtgtc gggctgggcc ctgacaagcc      60
acctgaggag aggctcggag ccgggcccgg accccggcga ttgccgcccg cttctctcta     120
gtctcacgag gggtttcccg cctcgcaccc ccacctctgg acttgccttt ccttctcttc     180
tccgcgtgtg gagggagcca gcgcttaggc cggagcgagc ctggggggccg ccgccgtga     240 agacatcgcg gggaccgatt caccatggag ggcgccggcg gcgcgaacga caagaaaaag     300
ataagttctg aacgtcgaaa agaaaagtct cgagatgcag ccagatctcg gcgaagtaaa     360
gaatctgaag ttttttatga gcttgctcat cagttgccac ttccacataa tgtgagttcg     420
catcttgata aggcctctgt gatgaggctt accatcagct atttgcgtgt gaggaaactt     480
ctggatgctg gtgatttgga tattgaagat gacatgaaag cacagatgaa ttgcttttat     540
ttgaaagcct tggatggttt tgttatggtt ctcacagatg atggtgacat gatttacatt     600
tctgataatg tgaacaaata catgggatta actcagtttg aactaactgg acacagtgtg     660
tttgatttta ctcatccatg tgaccatgag gaaatgagag aaatgcttac acacagaaat     720
ggccttgtga aaaagggtaa agaacaaaac acacagcgaa gcttttttct cagaatgaag     780
tgtaccctaa ctagccgagg aagaactatg aacataaagt ctgcaacatg gaaggtattg     840
```

```
cactgcacag gccacattca cgtatatgat accaacagta accaacctca gtgtgggtat    900
aagaaaccac ctatgacctg cttggtgctg atttgtgaac ccattcctca cccatcaaat    960
attgaaattc ctttagatag caagactttc ctcagtcgac acagcctgga tatgaaattt   1020
tcttattgtg atgaaagaat taccgaattg atgggatatg agccagaaga acttttaggc   1080
cgctcaattt atgaatatta tcatgctttg gactctgatc atctgaccaa aactcatcat   1140
gatatgttta ctaaaggaca agtcaccaca ggacagtaca ggatgcttgc caaaagaggt   1200
ggatatgtct gggttgaaac tcaagcaact gtcatatata acaccaagaa ttctcaacca   1260
cagtgcattg tatgtgtgaa ttacgttgtg agtggtatta ttcagcacga cttgattttc   1320
tcccttcaac aaacagaatg tgtccttaaa ccggttgaat cttcagatat gaaaatgact   1380
cagctattca ccaaagttga atcagaagat acaagtagcc tctttgacaa acttaagaag   1440
gaacctgatg ctttaacttt gctggcccca gccgctggag acacaatcat atctttagat   1500
tttggcagca acgacacaga aactgatgac cagcaacttg aggaagtacc attatataat   1560
gatgtaatgc tcccctcacc aacgaaaaa ttacagaata taaatttggc aatgtctcca   1620
ttacccaccg ctgaaacgcc aaagccactt cgaagtagtc ctgaccctgc actcaatcaa   1680
gaagttgcat taaaattaga accaaatcca gagtcactgg aactttcttt taccatgccc   1740
cagattcagg atcagacacc tagtccttcc gatggaagca ctagacaaag ttcacctgag   1800
cctaatagtc ccagtgaata ttgttttttat gtggatagtg atatggtcaa tgaattcaag   1860
ttggaattgg tagaaaaact ttttgctgaa gacacagaag caaagaaccc attttctact   1920
caggacacag atttagactt ggagatgtta gctccctata tcccaatgga tgatgacttc   1980
cagttacgtt ccttcgatca gttgtcacca ttagaaagca gttccgcaag ccctgaaagc   2040
gcaagtcctc aaagcacagt tacagtattc cagcagactc aaatacaaga acctactgct   2100
aatgccacca ctaccactgc caccactgat gaattaaaaa cagtgacaaa agaccgtatg   2160
gaagacatta aatattgat tgcatctcca tctcctaccc acatacataa agaaactact    2220
agtgccacat catcaccata tagagatact caaagtcgga cagcctcacc aaacagagca   2280
ggaaaaggag tcatagaaca gacagaaaaa tctcatccaa gaagccctaa cgtgttatct   2340
gtcgctttga gtcaaagaac tacagttcct gaggaagaac taaatccaaa gatactagct   2400
ttgcagaatg ctcagagaaa gcgaaaaatg gaacatgatg gttcactttt tcaagcagta   2460
ggaattggaa cattattaca gcagccagac gatcatgcag ctactacatc actttcttgg   2520
aaacgtgtaa aaggatgcaa atctagtgaa cagaatggaa tggagcaaaa gacaattatt   2580
ttaataccct ctgatttagc atgtagaactg ctggggcaat caatggatga agtggatta   2640
ccacagctga ccagttatga ttgtgaagtt aatgctccta tacaaggcag cagaaaccta   2700
ctgcagggtg aagaattact cagagctttg gatcaagtta actgagcttt ttcttaattt   2760
cattcctttt tttggacact ggtggctcac tacctaaagc agtctattta tattttctac   2820
atctaatttt agaagcctgg ctacaatact gcacaaactt ggttagttca attttgatc   2880
cccttctac ttaatttaca ttaatgctct tttttagtat gttctttaat gctggatcac   2940
agacagctca ttttctcagt ttttggtat ttaaaccatt gcattgcagt agcatcattt   3000
taaaaaatgc accttttat ttatttattt ttggctaggg agtttatccc ttttttcgaat   3060
tattttaag aagatgccaa tataatttt gtaagaaggc agtaacctttt catcatgatc   3120
ataggcagtt gaaaatttt tacacctttt tttcacatt ttacataaat aataatgctt   3180
tgccagcagt acgtggtagc cacaattgca caatatattt tcttaaaaaa taccagcagt   3240
```

```
tactcatgga atatattctg cgtttataaa actagttttt aagaagaaat ttttttggc      3300 ctatgaaatt gttaaacctg aacatgaca ttgttaatca tataataatg attcttaaat      3360
gctgtatggt ttattattta aatgggtaaa gccatttaca taatatagaa agatatgcat      3420
atatctagaa ggtatgtggc atttatttgg ataaaattct caattcagag aaatcatctg      3480
atgtttctat agtcactttg ccagctcaaa agaaaacaat accctatgta gttgtggaag      3540
tttatgctaa tattgtgtaa ctgatattaa acctaaatgt tctgcctacc ctgttggtat      3600
aaagatattt tgagcagact gtaaacaaga aaaaaaaat catgcattct tagcaaaatt       3660
gcctagtatg ttaatttgct caaaatacaa tgtttgattt tatgcacttt gtcgctatta      3720
acatcctttt tttcatgtag atttcaataa ttgagtaatt ttagaagcat tattttagga      3780
atatatagtt gtcacagtaa atatcttgtt ttttctatgt acattgtaca aattttcat       3840 tccttttgct ctttgtggtt ggatctaaca ctaactgtat tgttttgtta catcaaataa      3900
acatcttctg tggaaaaaaa aaaaaaaaaa aaa                                   3933

<210> SEQ ID NO 60
<211> LENGTH: 3166
<212> TYPE: DNA
<213> ORGANISM: Homo sapiens
<220> FEATURE:
<221> NAME/KEY: misc_feature
<222> LOCATION: (1)..(3166)
<223> OTHER INFORMATION: VEGF A

<400> SEQUENCE: 60
aagagctcca gagagaagtc gaggaagaga gagacggggt cagagagagc gcgcgggcgt        60
gcgagcagcg aaagcgacag ggcaaagtg agtgacctgc ttttgggggt gaccgccgga       120
gcgcggcgtg agccctcccc cttgggatcc cgcagctgac cagtcgcgct gacggacaga       180
cagacagaca ccgcccccag ccccagttac cacctcctcc ccggccggcg gcggacagtg       240
gacgcggcgg cgagccgcgg gcaggggccg gagcccgccc ccggaggcgg ggtggagggg       300
gtcggagctc gcgcgtcgc actgaaactt ttcgtccaac ttctgggctg ttctcgcttc       360
ggaggagccg tggtccgcgc ggggggaagcc gagccgagcg gagccgcgag aagtgctagc      420
tcgggccggg aggagccgca gccggaggag ggggaggagg aagaagagaa ggaagaggag       480
agggggccgc agtggcgact cggcgctcgg aagccgggct catggacggg tgaggcggcg       540
gtgtgcgcag acagtgctcc agcgcgcgcg ctccccagcc ctggcccggc ctcgggccgg       600
gaggaagagt agctcgccga ggcgccgagg agagcgggcc gccccacagc ccgagccgga       660
gagggacgcg agccgcgcgc cccggtcggg cctccgaaac catgaacttt ctgctgtctt       720
gggtgcattg gagccttgcc ttgctgctct acctccacca tgccaagtgg tcccaggctg       780
cacccatggc agaaggagga gggcagaatc atcacgaagt ggtgaagttc atggatgtct       840
atcagcgcag ctactgccat ccaatcgaga ccctggtgga catcttccag gagtaccctg       900
atgagatcga gtacatcttc aagccatcct gtgtgccccct gatgcgatgc gggggctgct       960
ccaatgacga gggcctggag tgtgtgccca ctgaggagtc caacatcacc atgcagatta      1020
tgcggatcaa acctcaccaa ggccagcaca taggagagat gagcttccta cagcacaaca      1080
aatgtgaatg cagaccaaag aaagatagag caagacaaga aaatccctgt gggccttgct      1140
cagagcggag aaagcatttg tttgtacaag atccgcagac gtgtaaatgt tcctgcaaaa      1200
acacacactc gcgttgcaag gcgaggcagc ttgagttaaa cgaacgtact tgcagatgtg      1260
acaagccgag gcggtgagcc gggcaggagg aaggagcctc cctcagggtt tcgggaacca      1320
```

```
gatctctctc caggaaagac tgatacagaa cgatcgatac agaaaccacg ctgccgccac    1380
cacaccatca ccatcgacag aacagtcctt aatccagaaa cctgaaatga aggaagagga    1440
gactctgcgc agagcacttt gggtccgag ggcgagactc cggcggaagc attcccgggc    1500
gggtgaccca gcacggtccc tcttggaatt ggattcgcca tttattttt cttgctgcta    1560 aatcaccgag cccggaagat tagagagttt tatttctggg attcctgtag acacacccac    1620
ccacatacat acatttatat atatatatat tatatatata taaaaataaa tatctctatt    1680
ttatatatat aaaatatata tattctttt ttaaattaac agtgctaatg ttattggtgt    1740
cttcactgga tgtatttgac tgctgtggac ttgagttggg aggggaatgt tcccactcag    1800
atcctgacag ggaagaggag gagatgagag actctggcat gatctttttt ttgtcccact    1860
tggtggggcc agggtcctct cccctgccca agaatgtgca aggccagggc atggggcaa    1920 atatgaccca gttttgggaa caccgacaaa cccagccctg gcgctgagcc tctctacccc    1980
aggtcagacg gacagaaaga caaatcacag gttccgggat gaggacaccg gctctgacca    2040
ggagtttggg gagcttcagg acattgctgt gctttgggga ttccctccac atgctgcacg    2100
cgcatctcgc ccccaggggc actgcctgga agattcagga gctgggcgg ccttcgctta    2160 ctctcacctg cttctgagtt gcccaggagg ccactggcag atgtcccggc gaagagaaga    2220
gacacattgt tggaagaagc agcccatgac agcgcccctt cctgggactc gccctcatcc    2280
tcttcctgct ccccttcctg gggtgcagcc taaaaggacc tatgtcctca ccattgaa     2340 accactagtt ctgtcccccc aggaaacctg gttgtgtgtg tgtgagtggt tgaccttcct    2400
ccatcccctg gtccttccct tcccttcccg aggcacagag agacagggca ggatccacgt    2460
gcccattgtg gaggcagaga aaagagaaag tgttttatat acggtactta tttaatatcc    2520 cttttaatt agaaattaga acagttaatt taattaaaga gtagggtttt ttttcagtat    2580
tcttggttaa tatttaattt caactattta tgagatgtat cttttgctct ctcttgctct    2640
cttatttgta ccggttttg tatataaaat tcatgtttcc aatctctctc tccctgatcg    2700
gtgacagtca ctagcttatc ttgaacagat atttaatttt gctaacactc agctctgccc    2760
tccccgatcc cctggctccc cagcacacat tcctttgaaa gagggtttca atatacatct    2820
acatactata tatatattgg gcaacttgta tttgtgtgta tatatatata tatatgttta    2880
tgtatatatg tgatcctgaa aaaataaaca tcgctattct gtttttttata tgttcaaacc    2940 aaacaagaaa aaatagagaa ttctacatac taaatctctc tccttttta attttaatat    3000 ttgttatcat ttatttattg gtgctactgt ttatccgtaa taattgtggg gaaaagatat    3060
taacatcacg tctttgtctc tagtgcagtt tttcgagata ttccgtagta catattatt    3120 tttaaacaac gacaaagaaa tacagatata tcttaaaaaa aaaaaa                  3166
```

<210> SEQ ID NO 61
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: sequence stemming from wild human p53

<400> SEQUENCE: 61
gaggtgcgtg tttgtgc                                                    17

<210> SEQ ID NO 62

```
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: sequence stemming from wild human p53

<400> SEQUENCE: 62
gcatgaaccg gaggcccat                                                  19

<210> SEQ ID NO 63
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: sequence stemming from wild human p53

<400> SEQUENCE: 63
gcatgaaccg gaggcccat                                                  19

<210> SEQ ID NO 64
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: sequence stemming from wild human p53

<400> SEQUENCE: 64
gcatgaaccg gaggcccat                                                  19

<210> SEQ ID NO 65
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: sequence stemming from wild human p53

<400> SEQUENCE: 65
ctgcatgggc ggcatgaac                                                  19

<210> SEQ ID NO 66
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: sequence stemming from wild human p53

<400> SEQUENCE: 66
tgggagagac cggcgcaca                                                  19

<210> SEQ ID NO 67
<211> LENGTH: 19
<212> TYPE: DNA
<213> ORGANISM: Artificial Sequence
<220> FEATURE:
<223> OTHER INFORMATION: Description of Artificial Sequence: Synthetic
```

```
      oligonucleotide
<220> FEATURE:
<223> OTHER INFORMATION: sequence stemming from wild human p53

<400> SEQUENCE: 67
tgtgaggcac tgcccccac                                              19

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: sequence stemming from wild human p53

<400> SEQUENCE: 68
taacagttcc tgcatgggcg                                             20

<210> SEQ ID NO 69
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: sequence stemming from the human mutated gene
      p53 bearing the mutation r273h

<400> SEQUENCE: 69
gaggtgcatg tttgtgc                                                17

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: sequence stemming from the human mutated gene
      p53 bearing the mutation r248q

<400> SEQUENCE: 70
gcatgaacca gaggcccat                                              19

<210> SEQ ID NO 71
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: sequence stemming from the human mutated gene
      p53 bearing the mutation r248w

<400> SEQUENCE: 71
gcatgaactg gaggccat                                               18

<210> SEQ ID NO 72
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: sequence stemming from the human mutated gene
      p53 bearing the mutation r249s

<400> SEQUENCE: 72
gcatgaaccg gagtcccat                                                        19

<210> SEQ ID NO 73
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: sequence stemming from the human mutated gene
      p53 bearing the mutation g245s

<400> SEQUENCE: 73
ctgcatgggc agcatgaac                                                        19

<210> SEQ ID NO 74
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: sequence stemming from the human mutated gene
      p53 bearing the mutation r282w

<400> SEQUENCE: 74
tgggagagac tggcgcaca                                                        19

<210> SEQ ID NO 75
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: sequence stemming from the human mutated gene
      p53 bearing the mutation r175h

<400> SEQUENCE: 75
tgtgaggcgc tgcccccac                                                        19

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: sequence stemming from the human mutated gene
      p53 bearing the mutation c242s

<400> SEQUENCE: 76
taacagttcc tccatgggcg                                                       20

<210> SEQ ID NO 77
<211> LENGTH: 3231
<212> TYPE: DNA
<213> ORGANISM: Homo sapiens
<220> FEATURE:
<223> OTHER INFORMATION: androgen receptor

<400> SEQUENCE: 77

```
agctagctgc agcgactacc gcatcatcac agcctgttga actcttctga gcaagagaag      60
gggaggcggg gtaagggaag taggtggaag attcagccaa gctcaaggat ggaagtgcag     120
ttagggctgg gaagggtcta ccctcggccg ccgtccaaga cctaccgagg agctttccag     180
aatctgttcc agagcgtccg cgaagtgatc cagaacccgg gccccaggca cccagaggcc     240
gcgagcgcag cacctcccgg cgccagtttg ctgctgctgc agcagcagca gcagcagcag     300
cagcagcagc agcagcagca gcagcaagag actagcccca ggcagcagca gcagcagcag     360
ggtgaggatg gttctcccca agcccatcgt agaggcccca caggctacct ggtcctggat     420
gaggaacagc aaccttcaca gccgcagtcg gccctggagt gccaccccga gagaggttgc     480
gtcccagagc ctggagccgc cgtggccgcc agcaaggggc tgccgcagca gctgccagca     540
cctccggacg aggatgactc agctgcccca tccacgttgt ccctgctggc ccccactttc     600
cccggcttaa gcagctgctc cgctgacctt aaagacatcc tgagcgaggc cagcaccatg     660
caactccttc agcaacagca gcaggaagca gtatccgaag gcagcagcag cgggagagcg     720
agggaggcct cgggggctcc cacttcctcc aaggacaatt acttaggggg cacttcgacc     780
atttctgaca cgccaaggaa gttgtgtaag gcagtgtcgg tgtccatggg cctgggtgtg     840
gaggcgttgg agcatctgag tccagggggaa cagcttcggg gggattgcat gtacgcccca     900
cttttgggag ttccacccgc tgtgcgtccc actccttgtg ccccattggc cgaatgcaaa     960
ggttctctgc tagacgacag cgcaggcaag agcactgaag atactgctga gtattcccct    1020
ttcaagggag gttacaccaa agggctagaa ggcgagagcc taggctgctc tggcagcgct    1080
gcagcaggga gctccgggac acttgaactg ccgtctaccc tgtctctcta caagtccgga    1140
gcactggacg aggcagctgc gtaccagagt cgcgactact acaactttcc actggctctg    1200
gccggaccgc cgcccctcc gccgcctccc catccccacg ctcgcatcaa gctggagaac    1260
ccgctggact acggcagcgc ctgggcggct cggcggcgc agtgccgcta tggggacctg    1320
gcgagcctgc atggcgcggg tgcagcggga cccggttctg ggtcaccctc agccgccgct    1380
tcctcatcct ggcacactct cttcacagcc gaagaaggcc agttgtatgg accgtgtggt    1440
ggtggtgggg gtggtggcgg cggcggcggc ggcggcggcg gcggcgaggc gggagctgta    1500
gcccctacg gctacactcg gcccctcag gggctggcgg gccaggaaag cgacttcacc    1560
gcacctgatg tgtggtaccc tggcggcatg gtgagcagag tgccctatcc cagtcccact    1620
tgtgtcaaaa gcgaaatggg ccctggatg gatagctact ccggacctta cggggacatg    1680
cgtttggaga ctgccaggga ccatgttttg cccattgact attactttcc accccagaag    1740
acctgcctga tctgtggaga tgaagcttct gggtgtcact atggagctct cacatgtgga    1800
agctgcaagg tcttcttcaa aagagccgct gaagggaaac agaagtacct gtgcgccagc    1860
agaaatgatt gcactattga taaattccga aggaaaaatt gtccatcttg tcgtcttcgg    1920
aaatgttatg aagcagggat gactctggga gcccggaagc tgaagaaact tggtaatctg    1980
aaactacagg aggaaggaga ggcttccagc accaccagcc ccactgagga gacaacccag    2040
aagctgacag tgtcacacat tgaaggctat gaatgtcagc ccatctttct gaatgtcctg    2100
gaagccattg agccaggtgt agtgtgtgct ggacacgaca acaaccagcc cgactccttt    2160
gcagccttgc tctctagcct caatgaactg ggagagagac agcttgtaca cgtggtcaag    2220
tgggccaagg ccttgcctgg cctccgcaac ttacacgtgg acgaccagat ggctgtcatt    2280
cagtactcct ggatggggct catggtgttt gccatgggct ggcgatcctt caccaatgtc    2340
aactccagga tgctctactt cgcccctgat ctggttttca atgagtaccg catgcacaag    2400
```

```
tcccggatgt acagccagtg tgtccgaatg aggcacctct ctcaagagtt tggatggctc    2460
caaatcaccc cccaggaatt cctgtgcatg aaagccatgc tactcttcag cattattcca    2520
gtggatgggc tgaaaaatca aaaattcttt gatgaacttc gaatgaacta catcaaggaa    2580
ctcgatcgta tcattgcatg caaaagaaaa aatcccacat cctgctcaag acgcttctac    2640
cagctcacca agctcctgga ctccgtgcag cctattgcga gagagctgca tcagttcact    2700
tttgacctgc taatcaagtc acacatggtg agcgtggact ttccggaaat gatggcagag    2760
atcatctctg tgcaagtgcc caagatcctt tctgggaaag tcaagcccat ctatttccac    2820
acccagtgaa gcattggaaa ccctatttcc ccaccccagc tcatgccccc tttcagatgt    2880
cttctgcctg ttataactct gcactactcc tctgcagtgc cttggggaat ttcctctatt    2940
gatgtacagt ctgtcatgaa catgttcctg aattctatct gctgggcttt ttttttctct    3000
ttctctcctt tcttttctt cttccctccc tatctaaccc tcccatggca ccttcagact    3060
ttgcttccca ttgtggctcc tatctgtgtt ttgaatggtg ttgtatgcct taaatctgtg    3120
atgatcctca tatggcccag tgtcaagttg tgcttgttta cacgcatctc tgtgccagcc    3180
acacaaaccg tttacttact taccgcaagg gaacttagag agctagaatt c            3231
```